United States Patent
Rogan et al.

(10) Patent No.: US 9,624,549 B2
(45) Date of Patent: Apr. 18, 2017

(54) STABLE GENE TARGETS IN BREAST CANCER AND USE THEREOF FOR OPTIMIZING THERAPY

(71) Applicants: Peter Keith Rogan, London (CA); Joan Helen Knoll, London (CA)

(72) Inventors: Peter Keith Rogan, London (CA); Joan Helen Knoll, London (CA)

(73) Assignee: Cytognomix Inc., London, Ontario (CA)

(*) Notice: Subject to any disclaimer, the term of this patent is extended or adjusted under 35 U.S.C. 154(b) by 327 days.

(21) Appl. No.: 13/744,459

(22) Filed: Jan. 18, 2013

(65) Prior Publication Data

US 2014/0206543 A1   Jul. 24, 2014

Related U.S. Application Data

(60) Provisional application No. 61/591,755, filed on Jan. 27, 2012.

(51) Int. Cl.
*G01N 33/50* (2006.01)
*C12Q 1/68* (2006.01)

(52) U.S. Cl.
CPC ..... *C12Q 1/6886* (2013.01); *C12Q 2600/106* (2013.01); *C12Q 2600/156* (2013.01); *C12Q 2600/158* (2013.01)

(58) Field of Classification Search
None
See application file for complete search history.

(56) References Cited

PUBLICATIONS

Chin et al. Genome Biology 2007, 8:R215.*
Hicks et al. Genome Res., 16 (2006), pp. 1465-1479.*
Park et al. Molecular oncology 6.3 (2012): 347-359.*
Fridlyand et al. (BMC cancer 6.1 (2006): 96).*
S Chin et al.(Genome Biology 2007, 8:R215; 13 pages).*

* cited by examiner

*Primary Examiner* — Jason Sims
(74) *Attorney, Agent, or Firm* — Tracy Jong Law Firm; Tracy P. Jong; Cheng Ning Jong

(57) ABSTRACT

A method for determining genes in breast cancer that are stable in copy number, expression and sequence in tumors from nearly all patients. Certain stable genes are targets of standard chemotherapy. The effectiveness of therapies that act upon these targets depends on maintaining the stability and integrity of these genes in tumors. Mutations in these targets result in poor response to therapies that target these gene products. In the instant invention, ordinarily stable gene targets are characterized as either normal or mutant for the purpose of determining whether to include or exclude particular drugs as potential treatments.

25 Claims, 7 Drawing Sheets
(7 of 7 Drawing Sheet(s) Filed in Color)

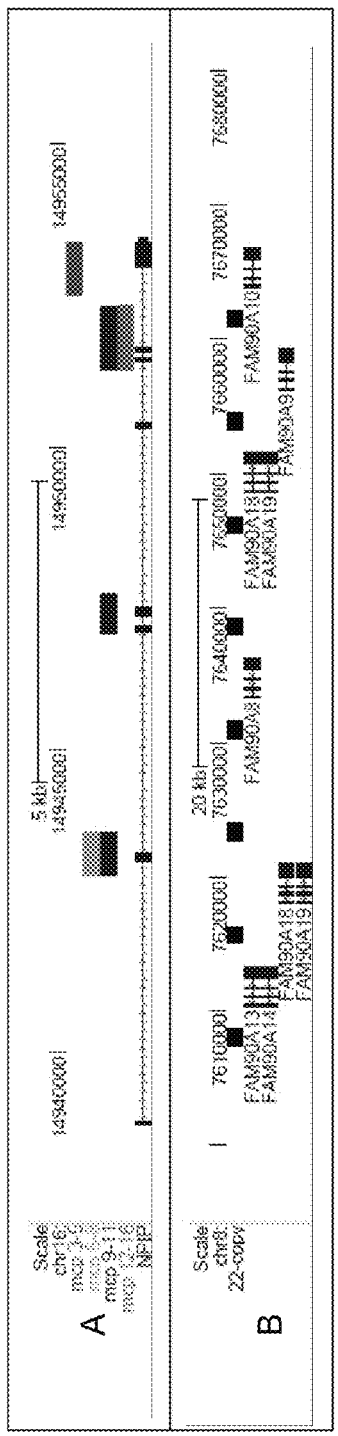
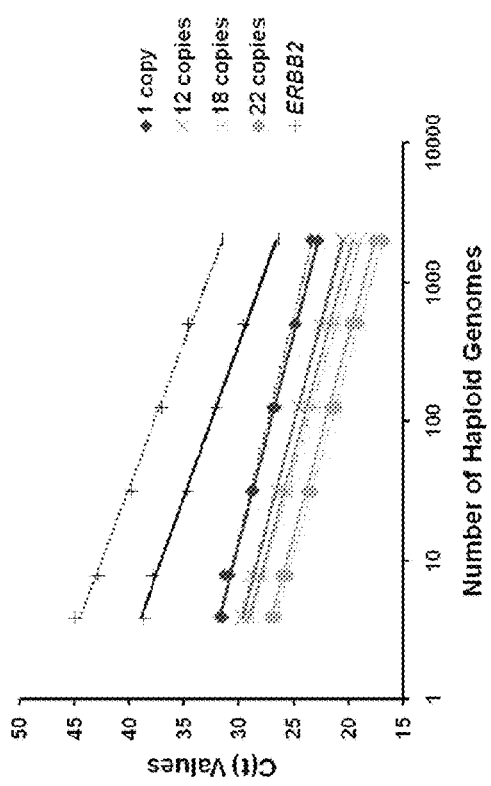
FIG. 6
FIG. 7

STABLE GENE TARGETS IN BREAST CANCER AND USE THEREOF FOR OPTIMIZING THERAPY

RELATED APPLICATIONS

This non-provisional patent application claims the benefit of priority from provisional application U.S. Ser. No. 61/591,755 filed Jan. 27, 2012.

BACKGROUND OF THE INVENTION

1. Field of the Invention

The present method relates to determination of the portion of the breast cancer genome common to many patients with normal inheritance and expression patterns for targeting pharmaceutical treatments. The method identifies drug targets for approved drugs and others in development and the sequences of these targets can be used to prioritize the selection of one or more drugs used in combination chemotherapy.

2. Description of the Related Art

Mutation studies establish which essential gene products are critical for growth and development of tumors. Despite extensive genomic instability, presumably, a minimal set of gene products are required for tumor cell survival. Loss-of-function mutations required for the proliferation and survival of cancer cells have been investigated using RNA interference. Ngo V N, Davis R E, Lamy L, Yu X, Zhao H, Lenz G, Lam L T, Dave S, Yang L, Powell J and others. 2006. A loss-of-function RNA interference screen for molecular targets in cancer. Nature 441:106-10; Silva J M, Marran K, Parker J S, Silva J, Golding M, Schlabach M R, Elledge S J, Hannon G J, Chang K. 2008. Profiling essential genes in human mammary cells by multiplex RNAi screening. Science 319:617-20.

Functional genetic analyses have identified causal cancer genes and much effort has been made to determine their contribution to the tumorigenic phenotype. Human cancers arise from the accumulation of numerous genetic and epigenetic alterations, which lead to dysregulation of protein-coding genes and interacting genes within a pathway. Schafer M, Schwender H, Merk S, Haferlach C, lckstadt K, Dugas M. 2009. Integrated analysis of copy number alterations and gene expression: a bivariate assessment of equally directed abnormalities. Bioinformatics 25:3228-35. Microarray studies assess abnormalities in copy number of specific genes, novel patterns of genome rearrangement and their association with survival in breast cancer, expression, and methylation status. Widschwendter and Jones, 2002. Hicks J, Krasnitz A, Lakshmi B, Navin N E, Riggs M, Leibu E, Esposito D, Alexander J, Troge J, Grubor V and others. 2006. Genome Res 16:1465-79. Perou C M, Sorlie T, Eisen M B, van de Rijn M, Jeffrey S S, Rees C A, Pollack J R, Ross D T, Johnsen H, Akslen L A and others. 2000. Molecular portraits of human breast tumors. Nature 406:747-52. Feinberg A P, Tycko B. 2004. The history of cancer epigenetics. Nat Rev Cancer 4:143-53. Widschwendter M, Jones P A. 2002. DNA methylation and breast carcinogenesis. Oncogene 21:5462-82. Genomic rearrangements, deletions, amplifications, and point mutations of genes regulating cell growth, apoptosis and DNA repair are responsible for unregulated proliferation. Vogelstein B, Kinzler K W. 2004. Cancer genes and the pathways they control. Nat Med 10:789-99.

Alterations in oncogenes and tumor-suppressor genes also contribute to tumorigenesis. Davies H, Bignell G R, Cox C, Stephens P, Edkins S, Clegg S, Teague J, Woffendin H, Garnett M J, Bottomley W and others. 2002. Mutations of the BRAF gene in human cancer. Nature 417:949-54. Friedberg E C. 2003. DNA damage and repair. Nature 421:436-40. Nowell P C. 2002. Tumor progression: a brief historical perspective. Semin Cancer Biol 12:261-6. Santarosa M, Ashworth A. 2004. Haploinsufficiency for tumor suppressor genes: when you don't need to go all the way. Biochim Biophys Acta 1654:105-22.

Common targets for amplification and deletion include ERBB2, MYC, CDKN2A, PTEN, and SMAD4. Collins S, Groudine M. 1982. Amplification of endogenous myc-related DNA sequences in a human myeloid leukaemia cell line. Nature 298:679-81. Hahn S A, Schutte M, Hoque A T, Moskaluk C A, da Costa L T, Rozenblum E, Weinstein C L, Fischer A, Yeo C J, Hruban R H and others. 1996. DPC4, a candidate tumor suppressor gene at human chromosome 18q21.1. Science 271:350-3. Kamb A, Gruis N A, Weaver-Feldhaus J, Liu Q, Harshman K, Tavtigian S V, Stockert E, Day R S, 3rd, Johnson B E, Skolnick M H. 1994. A cell cycle regulator potentially involved in genesis of many tumor types. Science 264:436-40. Li J, Yen C, Liaw D, Podsypanina K, Bose S, Wang S I, Puc J, Miliaresis C, Rodgers L, McCombie R and others. 1997. PTEN, a putative protein tyrosine phosphatase gene mutated in human brain, breast, and prostate cancer. Science 275:1943-7. Slamon D J, Clark G M, Wong S G, Levin W J, Ullrich A, McGuire W L. 1987. Human breast cancer: correlation of relapse and survival with amplification of the HER-2/neu oncogene. Science 235:177-82. Steck P A, Pershouse M A, Jasser S A, Yung W K, Lin H, Ligon A H, Langford L A, Baumgard M L, Nattier T, Davis T and others. 1997. Identification of a candidate tumor suppressor gene, MMAC1, at chromosome 10q23.3 that is mutated in multiple advanced cancers. Nat Genet 15:356-62.

In breast tumors, genomic regions that are consistently abnormal have been termed "saw-tooth" and "firestorm regions" because they possess the highest frequencies of gains and losses of genomic sequences (Hicks, et al., 2006). However, investigation of genes with little or no variation in copy number or expression has not been a focus of cancer studies, even though they may also contribute to maintenance of the tumor phenotype.

SUMMARY OF THE INVENTION

Confronted with frequent chromosome instability and gene mutation, some tumor cell lineages are surprisingly resilient to autophagy and apoptosis. The composition of the stable gene set in breast tumors contributes to their survival, regardless of whether they are derived from cancer stem cells or from source cells that have avoided inactivation of essential genes. Application of the instant invention characterizes regions of breast cancer genomes that share stable copy number (Chin S F, Teschendorff A E, Marioni J C, Wang Y, Barbosa-Morais N L, Thorne N P, Costa J L, Pinder S E, van de Wiel M A, Green A R and others. 2007. High-resolution aCGH and expression profiling identifies a novel genomic subtype of ER negative breast cancer. Genome Biol 8:R215. Hicks, et al 2006.) and exhibit levels of expression similar to matched normal tissues Naderi A, Teschendorff A E, Barbosa-Morais N L, Pinder S E, Green A R, Powe D G, Robertson J F, Aparicio S, Ellis I O, Brenton J D and others. 2007. A gene-expression signature to predict survival in breast cancer across independent data sets. Oncogene 26:1507-16. Turashvili G, Bouchal J, Baumforth K, Wei W, Dziechciarkova M, Ehrmann J, Klein J, Fridman E, Skarda J, Srovnal J and others. 2007. Novel markers for differentiation of lobular and ductal invasive breast carcinomas by laser microdissection and microarray analysis. BMC Cancer 7:55. These stable regions encode essential gene products by determining if standard breast cancer chemotherapies kill cancer cells by depriving tumors of these functions.

To overcome the limitations of the prior art, there is provided a novel and previously unknown method for determining gene targets for therapy of breast cancer specimens and for determining which of these targets are most suitable for selecting drugs for treatment. The method comprises:
(a): defining genes with stable copy number by the following steps:
(i), create a database consisting of microarray probe IDs, genomic coordinates, and hybridization copy number for each probe
(ii) group adjacent probes detecting the same copy number abnormality to form contiguous intervals and defined as regions of unstable copy number, wherein the copy number changes occur in a minimum of 10% of tumors,
(ii), identify the intervening regions as stable regions by complementing genomic coordinates of clusters of tightly linked unstable intervals
(iii) convolve the genomic coordinates of all known protein coding genes (CCDS) with those of stable and unstable regions,
wherein genes that overlapped adjacent stable and unstable intervals or that are present in unstable intervals are classified as unstable;
(b) defining genes with stable copy number and expression by the following:
(i) determine which genes were differentially expressed in breast tissue ductal and lobular carcinomas from normal adjacent ducts and lobules,
(ii) select the genes that are not differentially expressed in >90% of tumors,
(iii) join the gene set with stable copy number in tumors with the gene set that is not differentially expressed in the same matched tumors to form a set of dually stable genes with normal copy number and expression in a preponderance of tumors,
wherein the genes dually stable in genomic copy number and gene expression are independently confirmed as stable by a similar analysis of copy number and expression in an independent set of a different set of tumors and matched normal tissues of the same origin,
(c) identification of gene products involved in metabolism of cancer therapeutic agents as drug targets by comparison with pharmacogenetic databases, such as PharmGkb and Drugbank,
(d) restriction of drug targets to those classified as encoding dually stable genes, and
(e) determination of the metabolic pathways containing these stable drug targets, and the subsequent identification of with other stable targets co-occurred in the same pathway.

This novel process uses this gene selection procedure to identify candidates for novel therapeutic interventions in cancer. The process also uses this gene selection procedure to select among established, approved drugs whose protein targets are likely to be present and expressed in the preponderance of patients with tumors. This novel process also uses the recognition of mutations in otherwise dually stable genes to avoid prescribing established, approved drugs that are commonly used to treat cancer.

It is an object of the present invention to provide a process that determines which sequences in genomes of tumors contain normal copy numbers.

It is an object of the present invention to provide a process that determines which expressed sequences in tumors are similar to the expression of those sequences in normal cells.

It is an object of the present invention to provide a process that determines dually-stable genes with normal copy number and gene expression in tumors.

It is an object of the present invention to provide a process that identifies dually stable genes with normal copy number and gene expression in tumors that are targets of pharmacological treatment of said tumors.

Still another feature of this invention is that it identifies which dually stable genes in tumors contain mutations that reduce the effectiveness of pharmacological therapies ordinarily used to treat such tumors.

It is an object of the present invention to provide a process that repurposes pharmacological treatments ordinarily used to treat diseases distinct from cancer for treatment of tumors that contain dually stable gene products encoded by genes with normal copy number and gene expression that are targets of such pharmacological treatments.

These and other objects, features, and advantages of the present invention will become more fully apparent from the following description and appended claims, or may be learned by the practice of the invention as set forth hereinafter.

Particular Advantages of the Invention

The conventional and prevailing understanding about the mechanism of cancer initiation and maintenance is that it is driven by a set of abnormal genes which confer upon the tumor cell a number of unique phenotypes that are not present in the normal cell lineages from which it is derived. If cancer is driven and maintained solely by abnormal tumor suppressor genes and oncogenes, then all other genes in a tumor should be mutable. This is certainly not the case based on application of the instant invention to breast cancer genomes.

We have deduced a set of genes with unaltered copy number and expression in the majority of breast tumors that encode products in multiple tumor-associated biochemical pathways. Stably expressed genes contained within these stable genomic regions, their assigned functions and the pathways, and the susceptibility of cells to drugs that target their gene products are all consistent with selection for their preservation in the breast cancer genome. The large numbers of tumors analyzed, many of which exhibit defective DNA repair facilitating genome-wide mutation accumulation (Lahtz C, Pfeifer G P. 2011. Epigenetic changes of DNA repair genes in cancer. J Mol Cell Biol 3:51-8. Lahtz and Pfeifer, 2011), and our initial and replication analyses defining a consistent core set of dually stable genes each mitigate against the possibility that these are bystander genes that have fortuitously escaped mutation. The present analysis considers whether this gene set encodes functions required for homeostatic tumor initiation and maintenance in a set of phenotypically heterogeneous tumors. Dysregulated signalling still requires downstream genes stable in copy number and expression to propagate these signals and maintain basal cellular processes in cancer cells.

We also define a subset of sequence families in cis in tumor cells that possess the original germline genomic structure. A plausible explanation for retention of these multiplex structures is that they encode functionally essential genes or contain regulatory sequences; and/or maintain genomic architectures required for tumor viability. We confirm stable copy numbers in multiple breast cancer cell lines by Q-PCR and FISH. All multi-copy regions tested were stable in copy number, with the exception of a 22-copy per haploid sequence in the HS578T and T47D cell lines (Supporting Information FIG. 5). The 22-copy sequence is organized in four distinct clusters across 900 kb on chromosome 8p23.1 and contiguous loss of one or two of these clusters would result in a decrease in copy number. Array comparative hybridization of HS578T and T47D breast cancer cell lines confirms these results (Kao J, Salari K, Bocanegra M, Choi Y L, Girard L, Gandhi J, Kwei K A, Hernandez-Boussard T, Wang P, Gazdar A F and others. 2009. Molecular profiling of breast cancer cell lines defines relevant tumor models and provides a resource for cancer gene discovery. PLoS One 4:e6146. Kao et al., 2009). These deletions may be polymorphic or perhaps, all copies of this sequence family are not essential for somatic viability.

Stable genes which apparently do not undergo genomic rearrangement or do so at a low frequency are unlikely to be a chance observation, as the gene set is stable in both copy number analysis of a large number of tumors and in gene expression studies of breast cancer. 5,804 genes occur in stable copy number regions and exhibit stable expression in most tumors. Furthermore, analysis of 5 additional GEO sets, COSMIC and Cancer Consensus gene databases and sequencing dataset (Stephens P J, McBride D J, Lin M-L, Varela I, Pleasance E D, Simpson J T, Stebbings L A, Leroy C, Edkins S, Mudie L J and others. 2009. Complex landscapes of somatic rearrangement in human breast cancer genomes. Nature 462:1005-1010.), decreased our stable gene set by <2%. These stable genes are more consistently represented in metabolism, transcription, RNA metabolic processes, cell communication, chromatin assembly or disassembly, plasma membrane organization and biogenesis, cellular component assembly and protein transport. Although some of the pathways (e.g. MAPK, FIG. 4) containing stable genes, are also known to contain unstable mutation targets, we reconcile dysregulation of signalling proteins with the requirement for downstream stable genes to propagate abnormal signals and maintain basal cellular physiology. Mutations resulting in abnormal signalling at the inception of the pathway may dictate dysregulation and malfunction downstream, and therefore, stability of downstream genes in certain pathways may be critical for maintaining the tumor phenotype. Only a subset of genetic and epigenetic alterations are stable in the breast cancer genome (Feinberg and Tycko, 2004; Hicks, et al., 2006; Perou, et al., 2000; Widschwendter and Jones, 2002). Our findings support the idea that a common set of functional pathways are under selection to maintain tumor viability in all types of breast cancer. Stable genes tend to include those encoding responses to environmental stimuli. Primary ontologies describing these genes include cell recognition, intracellular protein transport, post-translational protein modification, cell cycle, ATP-binding and activity, drug response, membrane integrity, and signal transduction.

Our data also support the suggestion that certain therapeutic agents approved for treating other diseases might also be good candidates for treatment of breast tumors. Antidepressants, in particular, have been shown to act on some of the gene products encoded by stable genomic regions. Venlafaxine targets five gene products, four of which are encoded by genes in stable regions (HTR1A, SLC6A2, SLC6A4, and HTR1B). Targeting 5-hydroxytryptamine 1A and 1B receptors (HTR1A and HTR1B), inhibits growth and induces apoptosis in cell lines for prostate (Siddiqui E J, Shabbir M, Mikhailidis D P, Thompson C S, Mumtaz F H. 2006. The role of serotonin (5-hydroxytryptamine1A and 1B) receptors in prostate cancer cell proliferation. J Urol 176:1648-53.) and colorectal (Ataee R, Ajdary S, Zarrindast M, Rezayat M, Shokrgozar M A, Ataee A. 2010. Y25130 hydrochloride, a selective 5HT3 receptor antagonist has potent antimitogenic and apoptotic effect on HT29 colorectal cancer cell line. Eur J Cancer Prev 19:138-43.) cancer. Metformin, an anti-diabetic drug, targets PRKAB1 and is present within a stable interval, has anti-cancer activity against triple-negative breast cancer cell lines. Liu B, Fan Z, Edgerton S M, Deng X S, Alimova I N, Lind S E, Thor A D. 2009. Metformin induces unique biological and molecular responses in triple negative breast cancer cells. Cell Cycle 8:2031-40.

The effectiveness of these drugs may be related to preservation of gene structure and copy number of the multiple gene products that they target. Disruption of stable genes under selection would be expected to compromise key pathways needed to maintain tumors. Therapies that inhibit or inactivate multiple targets characterized by their stability in the genome and transcriptome may be an effective strategy to kill tumors. Judicious selection of stable targets in pathways that are intact in tumor cells, in which salvage (or alternative) pathways are mutated in these same cells, may provide a safer treatment approach. Redundant pathways could protect normal cells from toxic effects of these drugs, however tumor cells would remain susceptible. New therapies could focus on candidates that act on gene products encoded from within stable genomic regions (regardless of whether they were developed to treat breast cancer) and occur within key pathways required for tumor survival.

The claimed process facilitates a new way of using an existing drug because drugs previously approved for diagnosis of non-cancerous conditions target genes that we find to be dually stable in tumors. Therefore, the targets of these drugs are, based on the definition of stability in the instant invention, expressed in the majority of patients and may be effective in inhibiting biochemical pathways containing these targets.

The claimed process confines its reach to particular applications of natural laws by showing that an existing drug to be contraindicated in the treatment of a disease, where it may already be considered standard of care or at least a primary therapeutic approach. It is well known that some patients treated with conventional chemotherapies fail to respond to those therapies. If the therapeutic agent is directed towards a stable target gene product, that, in a non-responsive patient has succumbed to a rare or infrequent mutation, then the outcome of the therapy will be unsatisfactory. Detection of such rare mutations is essential to justify changing the chemotherapy regimen to one or more compounds that target distinctly different gene products. Thus, timely detection of an uncommon, unstable gene product in an otherwise stable target, can dictate alteration of the therapeutic regiment in order to improve the patient's outcome.

"[T]he claimed process includes not only a law of nature but also several unconventional steps that given the state of the art are antithetical to the "well-understood, routine, conventional activity already engaged in by the scientific community." Stable genes are considered the antithesis of the conventional 2-hit model of cancer (because, by definition, they generally are unmutated), which is the prevailing, accepted mechanism for the underlying genetic events that lead to cancer. The method employs a novel combination of steps, identifying genes with stable copy number, and identifying stable gene expression, lacking mutations, to deduce likely therapeutic targets of cancer.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. The patent or application file contains at least one drawing executed in color. Copies of this patent or patent application publication with color drawing(s) will be provided by the Office upon request and payment of the necessary fee. Understanding that these drawings depict only typical embodiments of the invention and are not therefore to be considered to be limiting of its scope, the invention will be described and explained with additional specificity and detail through the use of the accompanying drawings in which:

FIG. 6 shows stable multi-copy sequences are localized within and upstream of genes. The multicopy regions (mcp) are categorized by 3-5 copies (red bars), 6-8 copies (green bars), 9-11 copies (blue bars), 12-16 copies (magenta bars) and 22 copies (black bars). These were uploaded as custom tracks along with RefSeq genes track (NCBI Reference Sequence Collection) to the UCSC genome browser. (A) NPIP. A nuclear pore complex interacting protein, displays an intertwined set of multi-copy sequences that occur in 6-8, 9-11 and 12-16 copies. These sets of multi-copy sequences have unique compositions but share a common core sequence. For example, a portion of the 6-8 copy sequence is present in the 9-11 copy sequence. (B) Eight stable sequence intervals of a total twenty-copy multi-copy subfamily are located on 8p23.1. These stable multi-copy sequences occur upstream of subfamily II of primate-specific FAM90A, which originated from multiple duplications and rearrangements.

FIG. 7 shows quantitative real-time PCR confirms stable multi-copy regions and instable amplified ERBB2 region in SKBR3 breast cancer cell line. Standard curves of the SKBR3 cell line (solid lines) and normal DNAs (dotted lines) display C(t) values for ERBB2 and a variety of cis multi-copy probes (~100-2000) targeted to stable regions. The C(t) values are based on six 1:2 serial dilutions done triplicate (8000 copies→3.5 copies). ERBB2, a positive control, shows amplification and lower multi-copy regions of genomes in both SKBR3 and normal DNAs.

MDA-MB-231 metaphase cell hybridized with the P14KA probe. Hybridizations were consistently observed on the q arms of two chromosomes.

Figure 9:
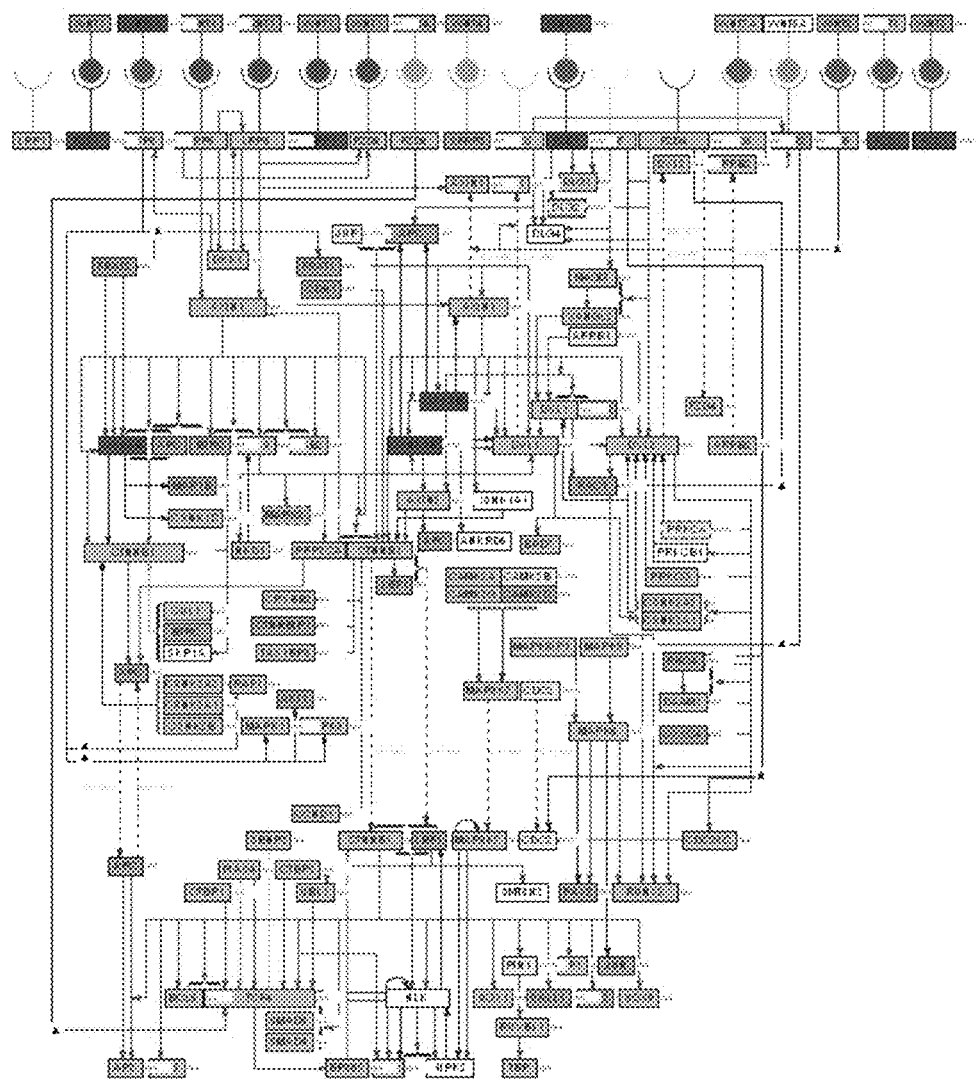

FIG. 9 shows MAPK signaling pathways with enrichment of unstable genes that also contain substantial numbers of genes with stable copy number and expression. Wnt signalling pathway with enrichment of unstable genes that also contain substantial numbers of genes with stable copy number and expression. The Wnt signalling pathway is annotated to show amplified genes (red), deleted genes (green), either amplified or deleted genes (yellow) and stable genes (blue). The preponderance of genes at the entry point (cell membrane) are either amplified and/or deleted, whereas genes with stable copy numbers are present downstream. This is consistent with abnormal signalling transmitted through these downstream gene products. Such downstream nodes may be selected to remain stable for the maintenance and viability of breast tumours. These may be potentially good drug targets for disrupting this pathway.

DETAILED DESCRIPTION OF THE PREFERRED EMBODIMENT

Briefly, the instant invention is a method for determining stable gene targets present in a set of breast cancer specimens comprising the following sequential steps: (a) definition of stable and unstable genomic regions in the breast cancer genome; (b) gene expression analysis with copy number data across breast cancer subtypes to identify genes that are dually stable in both copy number and gene expression; (c) pathway and gene ontology analysis of dually stable genes; and (d) selection of stable gene products as targets for breast cancer therapy. Each of these steps is described in greater detail below.

As used in this specification and the appended claims, the term "normal" or "demonstrated to be normal" shall mean the determination of which genes were differentially expressed in breast tissue ductal and lobular carcinomas from normal adjacent ducts and lobules and having a normal genomic copy number as diploid (2 copies for autosomes) and stable genes (normal gene expression)—as NOT being in the top or bottom 10 percentile of changes in expression. As will appreciated by those skilled in the art, when genetic abnormalities in a tumor are discovered, it requires a normal control tissue to compare it with. In breast cancer, the biopsy or the extracted tumor usually contains both the tumor and some adjacent normal breast tissue (since the surgeon wants to be certain that the entire tumor was removed). The normal tissue adjacent to the margin of the tumor is the preferred "matched normal." However, sometimes normal tissue of the same type is not available, and a different source (unaffected by the disease) is used. This is often blood. At the DNA level, the sequences of normal breast and blood are extremely similar. At the RNA level to measure gene expression, there can be some differences in representation of each gene, since different genes are expressed in white blood cells and breast tumor. In some instances, these were not matched from the same patient as the tumor. However, we argue that stable genes that are expressed in normal breast from a large number of women will diminish any inherent inter-individual variability, and probably represent the next best data to matched normal expression data from the same individual as the tumor was derived from.

Definition of Stable and Unstable Genomic Regions in the Breast Cancer Genome

Copy number and expression were analyzed from independent array comparative genomic hybridization datasets (aCGH): by a Representational Oligonucleotide Microarray Analysis (ROMA; GEO GPL7313) and a custom 30K 60-mer oligonucleotide array (GEO GPL5737). The ROMA platform contained approximately 85,000 probes with an approximately uniform genomic distribution. Lisitsyn N, Lisitsyn N, Wigler M. 1993. Cloning the differences between two complex genomes. Science 259:946-51. Lucito R, Healy J, Alexander J, Reiner A, Esposito D, Chi M, Rodgers L, Brady A, Sebat J, Troge J and others. 2003. Representational oligonucleotide microarray analysis: a high-resolution method to detect genome copy number variation. Genome Res 13:2291-305.

The data consist of 2,847 probes that detected autosomal deletions and amplifications in 243 primary breast carcinoma tissues (Hicks, et al., 2006). The custom array contained 60-mer oligonucleotides representing 28,830 unique genes (van den Ijssel P, Tijssen M, Chin S F, Eijk P, Carvalho B, Hopmans E, Holstege H, Bangarusamy D K, Jonkers J, Meijer G A and others. 2005. Human and mouse oligonucleotide-based array CGH. Nucleic Acids Res 33:e192.) In this aCGH platform, 1,684 highly recurrent altered regions were found in 171 primary breast tumors (Chin, et al., 2007).

Autosomal variations in copy number among multiple tumors were determined relative to a normal diploid male DNA (Hicks, et al., 2006) or to a reference pool of 50 randomized tumors (Chin, et al., 2007). In both studies, at least 10% of the tumors were required to display a consistent increase or decrease of at least one copy of the target locus. Neither study (Chin, et al., 2007; Hicks, et al., 2006) controlled for tumor subtype or heterogeneity. The requirement for ubiquitous genomic stability across all breast tumor subtypes is expected to identify common genomic intervals that are essentially un-altered in the most prevalent types of tumors (however, conclusions about stability in individual subtypes may not be valid).

ROMA probe IDs were ordered by genomic coordinate and hybridization copy number (based on NCBI Build 36/hg18 assembly). Adjacent probes with identical copy numbers (either increased or decreased) were grouped to form contiguous intervals with the same unstable genotypes. This same approach was taken to cluster intervals of gains or losses less than 105 kb apart using an independent dataset (Chin, et al., 2007).

Stable genomic intervals were inferred by complementing genomic coordinates of clusters of tightly linked unstable intervals. Genes located within stable and unstable regions were determined by convolving the genomic coordinates of all known protein coding genes (CCDS; build Hs36.3) with those of stable and unstable regions using the Galaxy metaserver. The history and results of the operations used to derive this and other genomic datasets are available at Cytognomix. However, the instructions provided herein are sufficient to obtain the same results as indicated below. Genes that overlapped the interface between adjacent stable and unstable intervals were classified as unstable. Although conservative, this approach avoided false assignments of unstable regions as stable. Stable chromosomal regions were further characterized by comparing the cumulative stability across each chromosome to the frequency of recurrent cytogenetic abnormalities in breast cancer (Mitelman Database of Chromosome Aberrations and Gene Fusions in Cancer; n=5328, September 2010 version).

Gene Expression Analysis with Copy Number Data Across Breast Cancer Subtypes

To identify genes in stable regions with nominal expression, datasets for tumor and normal samples were compared. These consisted of either matched tumor and normal marginal tissues from the same individual (Turashvili, et al., 2007) or individual tumors compared with average expression in a pooled set of 50 tumors (Naderi, et al., 2007). These comparisons were done to mitigate inter-individual sources of variability in differential gene expression.

Differentially expressed genes (the highest and lowest 10%) present in tumors relative to normal matched tissues in the Turashvili et al (2007) data were identified with Oncomine. These genes were then categorized with Galaxy according to their genomic stability using data from Hicks et al (2006). These results were replicated by analyzing the distribution of stable genomic intervals in an independent set of 113 matched primary breast tumors, for which both expression (Naderi, et al., 2007) and copy number abnormalities (Chin, et al., 2007) were available (Array Express: E-UCON-1). However, Chin et al (2007) and Naderi et al (2007) used a lower resolution microarray which detects genomic sequences at a lower density. Over- and under-expressed genes were similarly eliminated with GeneSpring GX Software (Agilent). P-values of log 2 ratios (fold change) were adjusted using the Benjamini-Hochberg multiple testing correction (p<0.05). The sets of stable genes and genes with nominal expression were indexed by HGNC (HUGO [Human Gene Organization] Gene Nomenclature Committee) symbol and joined with the Galaxy metaserver to identify common members of both sets. This set of stable genes should be independent of differentially genes expressed in a series of unrelated breast tumors. Subsequently, we analyzed differentially expressed genes in 5 independent series of paired breast tumor and matched normal specimens using the Student's t test (p<0.01; GEO datasets GDS2739, GDS3716, GDS3324, GDS3139, GDS2635); and compared these results with the stably expressed gene set deduced from Turashvili et al (2007) and Hicks et al (2006). The deduced dually stable gene set was also compared with the spectrum of commonly found mutations that either abolish gene function or cause rearrangement detected by DNA sequencing of candidate cancer genes and breast tumor exomes. The data sources included the most prevalent genes mutated in breast tumors in the Wellcome Trust Sanger Institute COSMIC database, the Sanger Cancer Gene Census database (as of Oct. 12, 2011), and from high throughput genome sequences of breast tumors (Stephens, et al., 2009).

It would be understood by those of skill in the art that the order of operations in defining stable genes in both copy number and expression is transitive. That is, the set of stably expressed genes can either be determined prior to identifying genes with normal copy number in a tumor, or this step can occur after identification of the genes with normal copy number. The intersection of these 2 genes sets will result in the same final set of stable genes, regardless of the order of the steps that determine them.

Pathway and Gene Ontology Analysis

Figure 4:
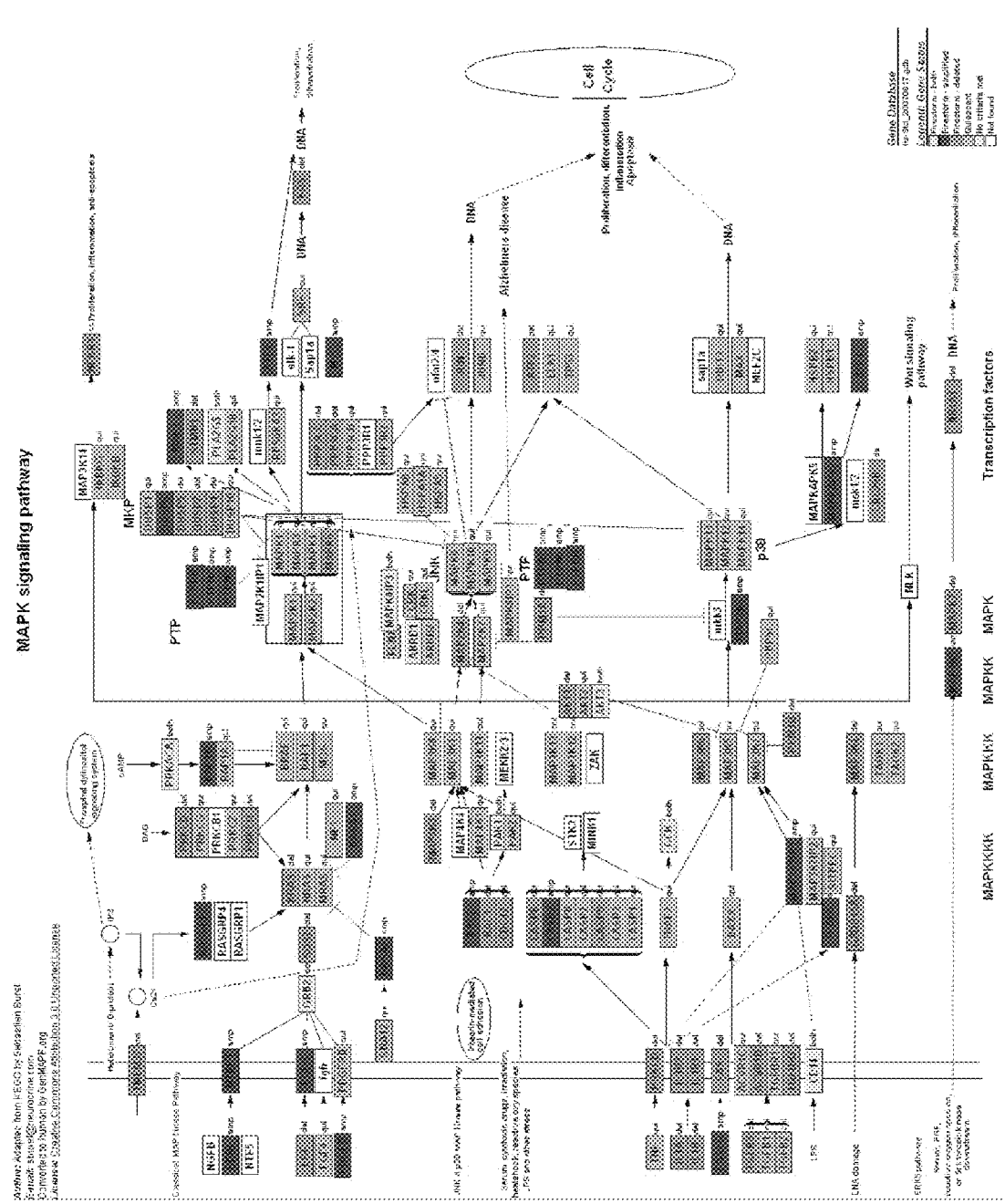
FIG. 4 shows MAPK signalling pathway with unstable and stable (copy number and expression) genes represented. The pathway is annotated to show amplified genes (red), deleted genes (green), either amplified or deleted genes (yellow) and stable genes (blue). The preponderance of genes at the entry point (cell membrane) are either amplified and/or deleted, whereas genes with stable copy numbers are present downstream. This is consistent with abnormal signalling propagated through these downstream gene products.

Protein-coding genes residing in stable regions were assigned to biochemical pathways with Webgestalt. Significant KEGG (Kyoto Encyclopedia of Genes and Genomes) pathways enriched in stable genes in the complete genome, were identified based on a hypergeometric test (p<0.01) for enrichment scores R>1 (Supporting Information Table S1). Genes were color-coded with the Gene Map Annotator & Pathway Profiler based on whether the copy number was decreased, increased or diploid (eg. FIG. 4, Supporting Information FIG. 9).

Previously annotated cancer pathways (KEGG: hsa05200) were compared to those enriched in the stable gene set. Stable cancer-related genes were classified according to gene ontology [GO] (Ashburner M, Ball C A, Blake J A, Botstein D, Butler H, Cherry J M, Davis A P, Dolinski K, Dwight S S, Eppig J T and others. 2000. Gene ontology: tool for the unification of biology. The Gene Ontology Consortium. Nat Genet 25:25-9.) and relevant GO terms were annotated using the Database for Annotation, Visualization and Integrated Discovery (DAVID). The Benjamini-Hochberg correction was applied to adjust for false positive stable gene assignments.

Genes in Stable Genomic Regions as Targets for Breast Cancer Therapy

Stable gene products involved in metabolism of breast cancer therapeutic agents were retrieved from the Pharmacogenomics Knowledge Base. For each agent, the KEGG pathways and the number of targets associated with stable genes were tabulated. The KEGG and PharmGKB results were linked to relate stable gene products with associated drugs and diseases. This process was repeated for all pathways that were significantly enriched (p<0.01) in the KEGG table of drug targets. We also determined which drugs targeted the largest number of stable genes in the significantly enriched pathways.

Identification and Confirmation of Multi-Copy Sequences in Stable Regions

Copy number changes were assessed in several multi-copy sequences predicted to be stable in breast cancer, since such changes would be more likely to occur in tumor genomes as a result of aberrant replication or recombination. Multi-copy, stable regions were identified using Galaxy by intersecting stable repeat-masked intervals with segmentally duplicated sequences in the genome (>500 bp long). The genomic copy number of each stable multi-copy interval was determined with mpiBLAST (www.mpiblast.org) and parsed to extract all divergent sequences with >70% and >80% similarity over >200 bp and >100 bp lengths, respectively. Multi-copy sequences which intersected unstable copy number sequence intervals in GEO GPL7313 were excluded from subsequent analyses. Stability of a subset of multi-copy regions from 5 different chromosomes was determined by quantitative PCR (Q-PCR) in 5 breast cancer cell lines [SKBR3 (Trempe, 1976), MCF7 (Soule et al., 1973), T47D (Keydar et al., 1979), HS578T (Hackett et al., 1977), and MDA-MB-231 (Cailleau et al., 1974)] and 10 control individuals (Supporting Information Table S2). Cailleau R, Young R, Olive M, Reeves W J, Jr. 1974. Breast tumor cell lines from pleural effusions. J Natl Cancer Inst 53:661-74. Hackett A J, Smith H S, Springer E L, Owens R B, Nelson-Rees W A, Riggs J L, Gardner M B. 1977. Two syngeneic cell lines from human breast tissue: the aneuploid mammary epithelial (Hs578T) and the diploid myoepithelial (Hs578Bst) cell lines. J Natl Cancer Inst 58:1795-806. Keydar I, Chen L, Karby S, Weiss F R, Delarea J, Radu M, Chaitcik S, Brenner H J. 1979. Establishment and characterization of a cell line of human breast carcinoma origin. Eur J Cancer 15:659-70. Soule H D, Vazguez J, Long A, Albert S, Brennan M. 1973. A human cell line from a pleural effusion derived from a breast carcinoma. J Natl Cancer Inst 51:1409-16. Trempe G L. 1976. Human breast cancer in culture. Recent Results Cancer Res 33-41.

ERBB2 (chr17q12) which is amplified in SKBR3 (Xiao Y, Gao X, Maragh S, Telford W G, Tona A. 2009. Cell lines as candidate reference materials for quality control of ERBB2 amplification and expression assays in breast cancer. Clin Chem 55:1307-15.) served as a positive copy number control. The Pfaffl method was used to determine the copy number relative to diploid. Pfaffl M W. 2001. A new mathematical model for relative quantification in real-time RT-PCR. Nucleic Acids Res 29:e45.

Genomic stability was also assessed by fluorescence in situ hybridization (FISH) on metaphase chromosomes with synthetic multi-copy probes developed from stable regions (DEFA1-chr 8p23.1 and P14KA-chr 22q11.2, Supporting Information Table S2) (Khan et al., 2011; Knoll and Rogan, 2003) and BAC clones (Osoegawa et al., 2001) spanning stable chemotherapy gene targets from 3 different chromosomes: FLT4 RP11-179D12-chr 5q35), GMPR2 (RP11-368G9-chr14q12), CSF1R (RP11-754J8-chr 5q33.1) (Knoll and Lichter, 2005). An ERBB2 BAC probe [RP11-94L15-chr 17p12,] in combination with a chromosome 17 centromere specific probe (CEP17) served as a positive control for copy number amplification (Wolff et al., 2007). Osoegawa K, Mammoser A G, Wu C, Frengen E, Zeng C, Catanese J J, de Jong P J. 2001. A bacterial artificial chromosome library for sequencing the complete human genome. Genome Res 11:483-96. Khan W A, Knoll J H M, Rogan P K. 2011. Context-based FISH localization of genomic rearrangements within chromosome 15q11.2q13 duplicons. Mol Cytogenet 4(1):15. Knoll J H, Rogan P K. 2003. Sequence-based, in situ detection of chromosomal abnormalities at high resolution. Am J Med Genet A 121A (3):245-57. Knoll J H M, Lichter P. 2005. In Situ Hybridization to Metaphase Chromosomes and Interphase Nuclei. In: Haines J L, Korf B R, Morton C C, Seidman C E, Seidman J G, Smith D R, editors. Current Protocols in Human Genetics: John Wiley & Sons, Inc. p 4.3.1-4.3.31. Wolff A C, Hammond, M E, Schwartz J N, Hagerty K L, Allred D C, Cote R J, Dowsett M, Fitzgibbons P L, Hanna W M, Langer A, McShane L M, Paik S, Pegram M D, Perez E A, Press M F, Rhodes A, Sturgeion C, Taube S E, Tubbs R, Vance G H, van de Vijver M, Wheeler T M, Hayes D F. 2007. American Society of Clinical Oncology/College of American Pathologists guideline recommendations for human epidermal growth factor receptor 2 testing in breast cancer. J Clin Oncol 25:118-45.

Example 1

Stable Regions in Genomes of Breast Cancer Patients

Figure 1:
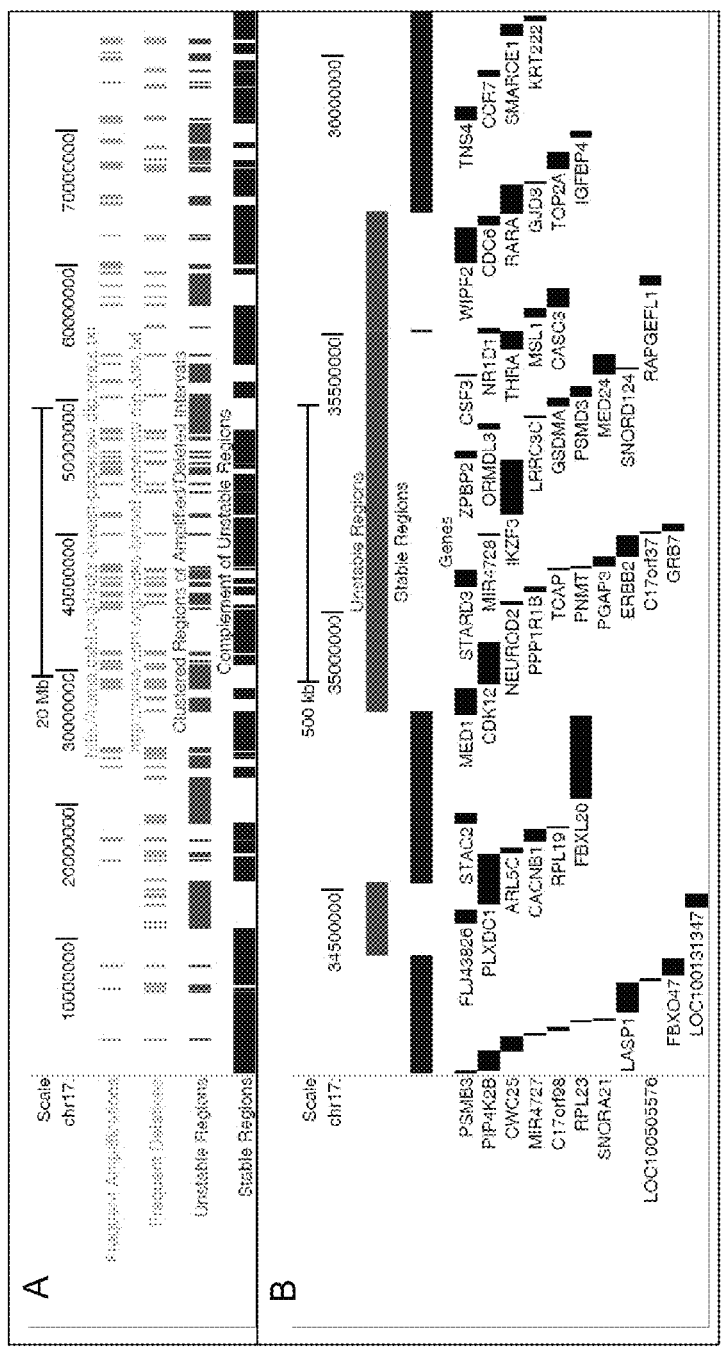
FIG. 1 shows unstable and stable genomic regions mapped to chromosome 17. (A) Probes that detected frequent amplifications and deletions are displayed (orange) along the entire chromosome 17. Merging genomic intervals corresponding to these probes formed unstable regions (red). Stable regions (blue) were derived from the complement of unstable regions. (B) Unstable regions, stable regions, and genes (black) are displayed for chromosome 17q12q21.1. The red arrow indicates the location of ERBB2, a gene within an unstable region and amplified in ~25% of breast cancers.

We report stable regions in the breast cancer genome based on analysis of two independent datasets which mapped copy number alterations (Chin, et al., 2007; Hicks, et al., 2006), and filter the content of these regions for genes with nominal expression levels (see Section 3.1.2). From 2,847 'representative or core' oligonucleotide probes that detected frequent deletions and amplifications in 243 primary breast carcinoma tissues, 766 contiguous genomic regions were derived and classified as unstable and 812 adjacent genomic intervals as stable (FIG. 1 and Table 1).

TABLE 1

Summary of aCGH Datasets Used to Derive Stable Copy Number Regions

|  | Dataset 1 (Hicks et al. 2006) | Dataset 2 (Chin et al. 2007) |
| --- | --- | --- |
| aCGH Platform | ROMA (GEO: GPL7313) | Custom array (GEO: GPL5737) |
| Total Probe No. | 85,000 (50-mer) | 30,000 (60-mer) |

TABLE 1-continued

Summary of aCGH Datasets Used to Derive Stable Copy Number Regions

|  | No. of Probes | | | No. of Regions | |
| --- | --- | --- | --- | --- | --- |
| Copy Number Abnormalities | 1,772 (amp) | 1,864 (del) | 782 (both) | 1,911 (gain) | 1,255 (loss) |
| Unstable Regions[1] | 766 | | | 828 | |
| Stable Regions | 812 | | | 680 | |
| Genes (CCDS) in Stable Regions[2] | 9,463 | | | 7,692 | |
| Stable Regions Common to Both Datasets | 535 regions (1,348,553,559 bp) | | | | |
| Stable Genes Common to Both Datasets | 3,859 | | | | |

[1]Merged genomic coordinates of adjacent probes (Dataset 1) or regions (Dataset 2) with the same copy number abnormality (see 2.1);
"amp" refers to amplification, "del" refers to deletion, and "bp" refers to base pair;
[2]Includes genes with and without corresponding Entrez IDs.

The number of probes and regions of frequent copy number abnormality are summarized by Dataset 1 and Dataset 2, respectively. Dataset 2 was used in our replication study. The numbers of unstable and corresponding stable regions are shown, as well as the number of protein-coding genes wholly contained within stable regions. The numbers of stable regions and protein-coding genes common to both datasets are summarized.

Figure 2:
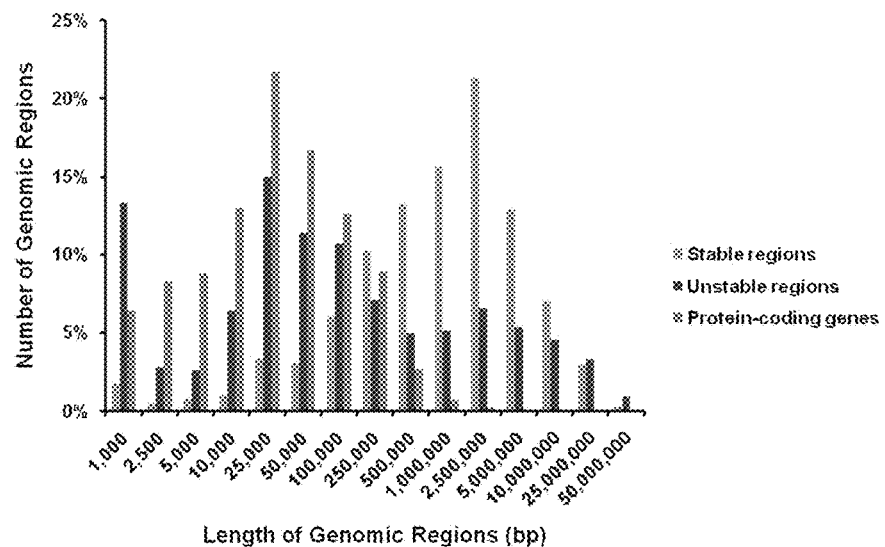
FIG. 2 shows frequency and length distributions of unstable and stable genomic regions and protein-coding genes. Histogram indicates that the majority of unstable regions (dark blue) are ≤250 kb in length (bin 250,000 bp) and stable regions (turquoise) are longer than 250 kb (bin 250,000 bp). The Y-axis represents the number of stable or unstable regions, and genes as a percentage from each group. The X-axis depicts genomic lengths binned in units of 1,000 bp. In comparison to stable regions, protein-coding genes (grey; consensus coding sequence project) have a smaller size distribution similar to that of unstable regions.
Figure 3:
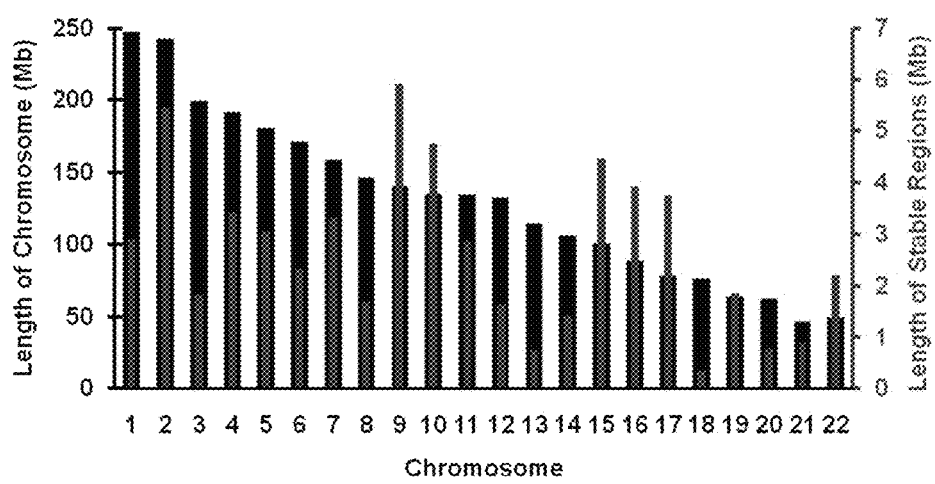
FIG. 3 shows length distribution of single-copy (sc) stable genomic intervals per autosome. Histogram compares the lengths of stable regions including those within segmentally duplicated regions (red) with overall chromosome length (black). While all chromosomes contain stable regions, the distribution of stable material is not related to chromosome length ($r^2$=0.401). On a per nucleotide basis, there is a higher degree of preservation of sc-genomic stability on chromosomes 2, 7, 9, 10, 15, 16, 17, 19 and 22. Stable regions of chromosome 13 and 18 appear to have more repetitive DNA (as represented by diminished length of sc-intervals) than the other chromosomes.

Stable copy number regions comprise 56.3% of the entire genome or 1.6 Gb. The distribution of unstable genomic region lengths is on average smaller (<250 kb) than the stable genomic intervals (>250 kb). Typically, stable interval lengths ranged from 1-2.5 Mb (21.3%; 173 of total 812). The most frequent protein-coding genes in stable intervals were 10,001-25,000 bp in length (4,310 of 19,856). Stable regions are therefore characterized by higher gene densities (FIG. 2). Using the same approach with data from another study (Chin, et al., 2007), we observed many of the same stable regions. That is, 828 unstable regions and 680 adjacent stable regions were deduced from the aCGH data. Of the 680 stable regions, 535 of them overlapped stable regions determined from Hicks et al (2006), equivalent to 1.3 Gb of the genome (Table 1). Chromosomes with the largest fraction of stable regions (FIG. 3) were associated with lower frequencies of cytogenetic abnormalities (for chromosomes 2, 9, 10 and 15: 3.1-3.5%) and those with lower stable region coverage had disproportionately higher frequencies of abnormalities (chromosomes 8, 13, 18, and 20) (Supporting Information Table S3).

Genomic architecture and paralogous structures often potentiate DNA rearrangements in tumor cells (Kolomietz, et al., 2002; Pace, et al., 2009). Kolomietz E, Meyn M S, Pandita A, Squire J A. 2002. The role of Alu repeat clusters as mediators of recurrent chromosomal aberrations in tumors. Genes Chromosomes Cancer 35:97-112. Pace J K, 2nd, Sen S K, Batzer M A, Feschotte C. 2009. Repair-mediated duplication by capture of proximal chromosomal DNA has shaped vertebrate genome evolution. PLoS Genet 5:e1000469.

Figure 5:
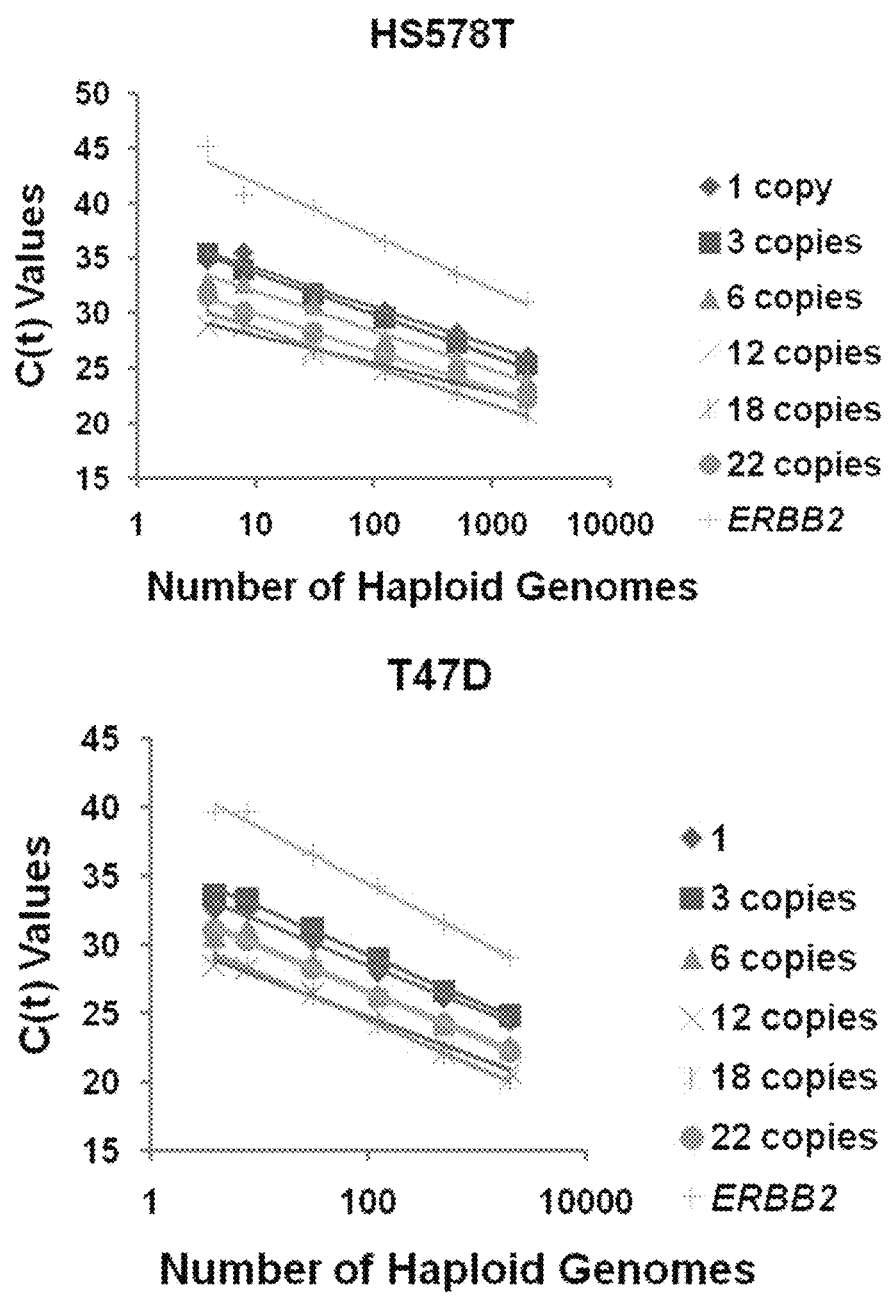
FIG. 5 shows Q-PCR results of multi-copy regions in breast cancer cell lines. Standard curves of C(t) values for different template concentrations for HS578T and T47D are shown. Amplification of different targets of stable multi-target intervals are color coded as indicated. The C(t) values represent the linear standard curve points based on six 1:2 serial dilutions done in triplicate (8000 copies→3.5 copies). As expected, lower copy sequences generally had higher C(t) values than higher copy number sequences except for 22-copy sequence in HS578T and T47D. In these cell lines, this sequence had C(t) values resembling that of 6-12 multi-copies.
Figure 8:
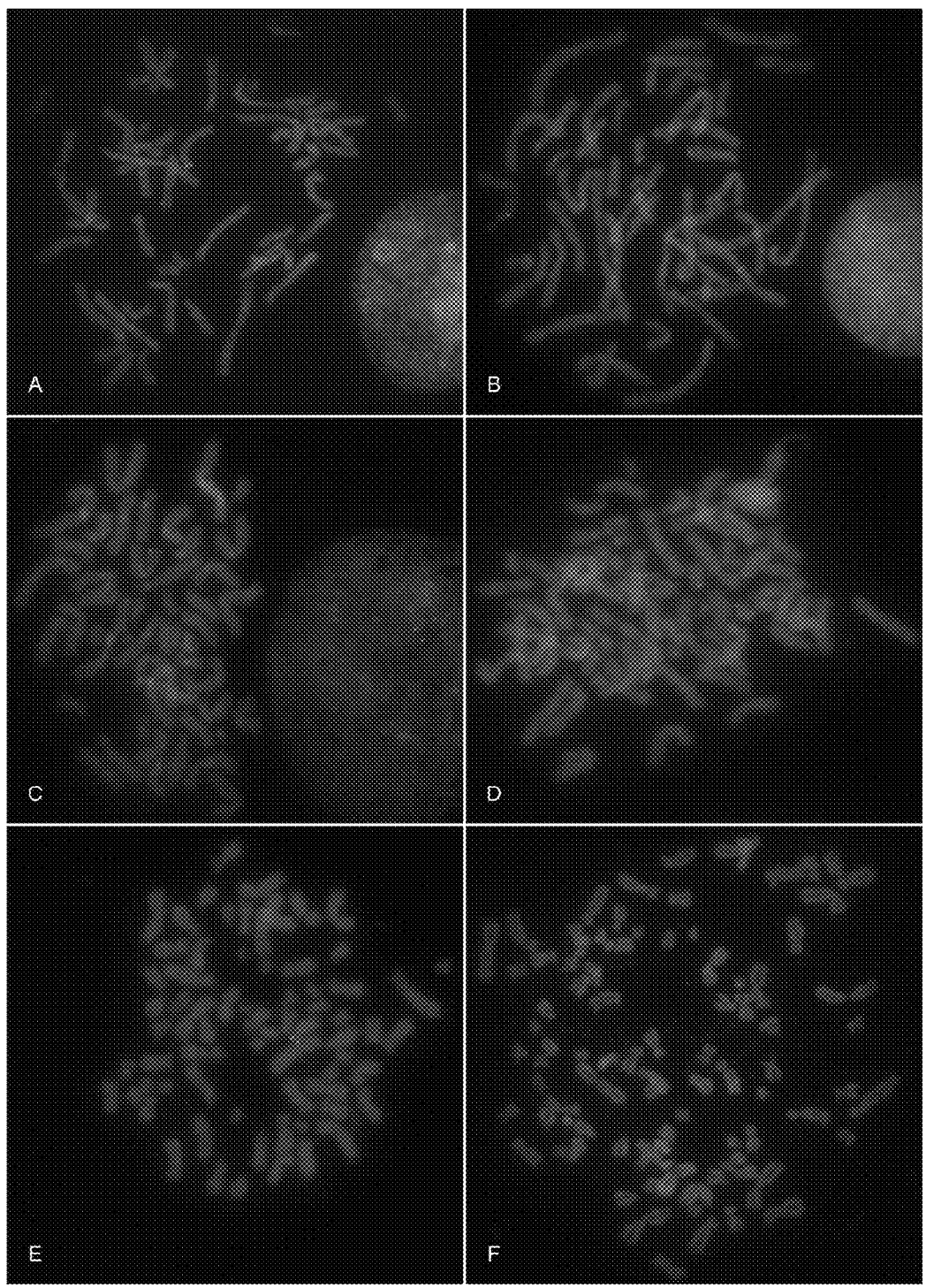
FIG. 8 shows FISH with DEFA1 and PI4KA multi-copy probes on human metaphase chromosomes from normal and breast cancer cell lines. Probes were labelled with digitoxigenin-11-dUTP and detected with rhodamine conjugated digoxigenin-antibody. Chromosomes were counterstained with 4',6-diamidino-2-phenylindole (DAPI). (A) Normal lymphocyte hybridized with a 4,242 base pair probe from DEFA1 on chromosome 8p23.1 The DEFA1 probe hybridizes to 3 genomic targets in cis at coordinates 1) 6862898-6867122; 2) 6843799-6848028; and 3) 88-6828923. Occasionally, two of the targets on a chromatid could be discriminated as shown in this cell but most often the hybridization targets which span 42 kb, coalesce on metaphase chromosomes to form a single hybridization on each chromatid. (b) Normal lymphocyte hybridized with a 2700 base pair probe from P14KA on chromosome 22q11.2. This P14KA probe hybridizes to 3 genomic targets in cis within 22q11.2 at coordinates 1) 201585595-20161294; 2) 19393293-19395994; and 3) 18764821-18767520. These targets span ~1.4 Mb near the centromere but individual targets could not be discriminated. (C) HS578T metaphase cell hybridized with DEFA1 probe. Hybridizations were consistently observed on the p arms of two chromosomes. (D) T47D metaphase cell hybridized with the P14KA probe. Hybridizations were consistently observed on the q arms of two chromosomes. (E) MCF-7 metaphase cell hybridized with the DEFA1 probe. Hybridizations were consistently observed on the p arm of only one chromosomes. (F)

We found stable regions contain paralogous regions in cis that appear to be maintained as an ensemble. Multi-copy, paralogous sequences in stable regions (FIG. 3) are present on every chromosome, but are proportionately less abundant on longer chromosomes and more common on shorter chromosomes. The highest percentages of paralogs are present on chromosomes 2 (9.1%), 9 (9.9%), 10 (7.9%), 15 (7.5%) and the lowest in chromosomes 13 (1.3%) and 18 (0.6%). Chromosome 18 was substantially underrepresented for stable regions relative to other F group chromosomes (ie. chr 16 and 17) and chromosome 15 was overrepresented compared to other D group chromosomes (ie. chr 13 and 14) (Supporting Information Table S3). The number of stable, in cis multi-copy sequences ranged from none on chromosome 1 to 356 for chromosome 16 (Supporting Information Table S4). Multi-copy families were more often distributed in cis (771) than in trans (360). There were 21 different multi-copy sequence families covering 5.7 Mb, with copy numbers ranging from 2 to 26 copies per haploid genome. Stability of 22, 18, 12, 6, and 3 copy sequence families in cis were tested in breast cancer cell lines and normal controls. Table 2 indicates stable genes present in multiple copies in the genome. Copy numbers of these sequence families were conserved in the cell lines by Q-PCR, with the exception of the 22-copy sequence family which was estimated to have 6-12 copies in HS578T and T47D (Supporting Information FIG. 5). Members of this sequence family were 1,234 bp in average length, organized in cis on chromosome 8 and distributed intergenically between FAM90A gene family members (Supporting Information FIG. 6). ERBB2 amplification in SKBR3 served as a positive control by Q-PCR (Supporting Information FIG. 7) and metaphase FISH. The stability of other deduced multi-copy sequences (DEFA1, P14KA) was also demonstrated by metaphase FISH in all but one breast cancer cell line, despite differing modal chromosome numbers (Supporting Information Table S5; Supporting Information FIG. 8).

TABLE 2

Stable Copy Number Genes Contained within in cis Multi-Copy Regions

| Gene Symbol | Gene Description |
|---|---|
| 3-5 Multi-Copy | |
| ABCC6 | NM_001171: ATP-binding cassette, sub-family G, member 6; NM_001079528: URG7 protein isoform 2 |
| ANAPC1 | anaphase promoting complex subunit 1 |
| AQP7 | aquaporin 7 |
| C2orf78 | hypothetical protein LOC388960 |
| CCDC144A | coiled-coil domain containing 144A |
| CCDC144B | coiled-coil domain containing 144B |
| CCDC144C | *Homo sapiens* cDNA clone IMAGE: 4837395. |
| CNTNAP3 | cell recognition molecule CASPR3 |
| DEFA1B | alpha-defensin 1b |
| DEFA3 | defensin, alpha 3 preproprotein |
| DUB3 | deubiquitinating enzyme 3 |
| FAM86B1 | NM_001083537: hypothetical protein LOC85002; NR_003494: FAM86B1 protein |
| FLJ32679 | hypothetical protein LOC440321 |
| FLJ36492 | *Homo sapiens* cDNA, FLJ18738 |
| GGT1 | gamma-glutamyltransferase 1 precursor |
| GOLGA6L1 | golgi autoantigen, golgin subfamily a-like |
| GOLGA8E | golgi autoantigen, golgin subfamily a, 8E |
| GOLGA8G | golgi autoantigen, golgin subfamily a, 8G |
| HERC2 | hect domain and RLD 2 |
| HERC2P3 | Putative uncharacterized protein (Fragment) |
| KIAA0393 | Uncharacterized protein ENSP00000372404 |
| LOC339047 | hypothetical protein LOC339047 |
| LOC339240 | Putative uncharacterized protein FLJ46089 precursor |
| LOC375133 | *Homo sapiens* cDNA FLJ11279 fis, clone place1009444, highly similar to phosphatidylinositol 4-kinase alpha |
| LOC375133 | *Homo sapiens* cDNA FLJ11279 fis, clone place1009444, highly similar to phosphatidylinositol 4-kinase alpha |
| LOC392196 | *Homo sapiens* deubiquitinating enzyme 3 pseudogene (LOC392196), non-coding RNA |
| MBD3L2 | methyl-CpG binding domain protein 3-like 2 |
| NOMO1 | nodal modulator 1 |
| NOMO2 | nodal modulator 2 isoform 1 |
| NOMO3 | nodal modulator 3 |
| NPIP | nuclear pore complex interacting protein |
| OVOS2 | ovostatin 2 |
| PDXDC1 | pyridoxal-dependent decarboxylase domain |
| PI4KA | phosphatidylinositol 4-kinase type 3 alpha |
| PKD1 | NM_001009944: polycystin 1 isoform 1 precursor; NM_000296: polycystin 1 isoform 2 precursor |
| PLGLA | *Homo sapiens* plasminogen-like A (PLGLA), non-coding RNA |
| PLGLB1 | plasminogen-like B1 |
| PLGLB2 | plasminogen-like B2 |
| PRR20 | proline rich 20 |
| RGPD1 | RANBP2-like and GRIP domain containing 1 |
| RGPD2 | RANBP2-like and GRIP domain containing 2 |
| RGPD5 | RANBP2-like and GRIP domain containing 5 isoform |
| RGPD6 | RANBP2-like and GRIP domain containing 6 |
| RIMBP3 | DKFZP434H0735 protein |
| RIMBP3B | RIMS binding protein 3B |
| RIMBP3C | RIMS binding protein 3C |
| RRN3P1 | RNA polymerase I transcription factor homolog (*S. cerevisiae*) pseudogene 1 |
| URG7 | *Homo sapiens* up-regulated gene 7 (URG7) mRNA, complete cds |
| ZNF705D | zinc finger protein 705D |
| 6-8 Multi-Copy | |
| C2orf78 | hypothetical protein LOC388960 |
| DKFZp434P211 | *Homo sapiens* mRNA; cDNA DKFZp434P211 |
| FLJ32679 | hypothetical protein LOC440321 |
| GOLGA6L1 | golgi autoantigen, golgin subfamily a-like |
| GOLGA8E | golgi autoantigen, golgin subfamily a, 8E |
| GOLGA8G | golgi autoantigen, golgin subfamily a, 8G |
| LOC339047 | hypothetical protein LOC339047 |
| NPIP | nuclear pore complex interacting protein |
| PDXDC1 | pyridoxal-dependent decarboxylase domain |
| PKD1 | NM_001009944: polycystin 1 isoform 1 precursor; NM_000296: polycystin 1 isoform 2 precursor |
| RGPD1 | RANBP2-like and GRIP domain containing 1 |
| RGPD2 | RANBP2-like and GRIP domain containing 2 |
| RGPD5 | RANBP2-like and GRIP domain containing 5 isoform |
| RGPD6 | RANBP2-like and GRIP domain containing 6 |
| USP18 | ubiquitin specific protease 18 |
| 9-11 Multi-Copy | |
| LOC339047 | hypothetical protein LOC339047 |
| NPIP | nuclear pore complex interacting protein |
| RANBP2 | RAN binding protein 2 |
| RGPD1 | RANBP2-like and GRIP domain containing 1 |
| RGPD2 | RANBP2-like and GRIP domain containing 2 |
| RGPD5 | RANBP2-like and GRIP domain containing 5 isoform |
| RGPD6 | RANBP2-like and GRIP domain containing 6 |
| USP17 | ubiquitin specific peptidase 17 |
| 12-16 Multi-Copy | |
| LOC339047 | hypothetical protein LOC339047 |
| NPIP | nuclear pore complex interacting protein |
| NPIPL3 | nuclear pore complex interacting protein-like 3 |
| PDXDC2 | *Homo sapiens* cDNA: FLJ23482 fis, clone KAIA03142 |
| RUNDC2B | RUN domain containing 2B |

Multi-copy intervals are categorized by copy number, ie. 3-5, 6-8, 9-11 and 12-16 copies. More genes are associated with the lower number multi-copy intervals. Some genes contain several distinct multi-copy subfamilies giving rise to overlapping multi-copy sequences (e.g. NPIP, GOLGA8E). Many genes have not been assigned a function (e.g. PDXDC2, URG7).

Example 2

Stably expressed genes in stable copy number regions: major pathways and functions involved in tumor maintenance.

Within stable regions, there were 9,463 complete CCDS genes (8,083 with Entrez Gene IDs) and 7,403 genes within unstable regions. Expression analysis of paired breast tumors and normal controls (Turashvili, et al., 2007) demonstrated 5,804 genes to be stable at both genomic and transcript levels. These dually stable genes were analyzed in established cellular pathways and gene ontologies, which suggested functions that are maintained in the majority of breast tumors. Interestingly, many of the same pathways containing stable genes are also disrupted by abnormalities in unstable or mutated genes. We suggest that this overlap may be relevant to tumor initiation and/or maintenance. The dually stable gene set was enriched for KEGG pathway hsa05200, which includes neuroactive ligand-receptor interaction ($p=7.32e^{-14}$), cytokine-cytokine receptor interaction ($p=2.54e^{-12}$), MAPK signalling pathway ($p=1.76e^{-7}$), focal adhesion ($p=3.55e^{-10}$), Jak-STAT signalling pathway ($p=6.04e^{-8}$), cell cycle ($p=2.64e^{-7}$), cell-cell/adherens junction ($p=7.19e^{-9}$), and TGF-beta signalling ($p=1.01e^{-7}$; Supporting Information Table S1). Other pathways with significantly enriched stable genes included oxidative phosphorylation ($p=1.46e^{-14}$), Wnt signaling ($p=7.30e^{-10}$), natural killer cell mediated cytotoxicity ($p=2.58e^{-8}$), leukocyte transendothelial migration ($p=3.53e^{-8}$), and cell adhesion ($p=3.81e^{-5}$). Some interesting patterns emerge among the stable and unstable genes in the same pathways. In the MAPK pathway (FIG. 4), we noted a higher propensity for unstable gene products encoding surface receptors and ligands (i.e. initiating sites of aberrant signalling), contrasting with many stable genes being distributed throughout the rest of these pathways (i.e. to propagate the abnormal signals). A similar pattern emerged for the Wnt signalling pathway (Supporting Information FIG. 9).

Dually stable genes were classified according to biological processes to which they contribute. Cell adhesion and motility, signal transduction, transcriptional regulation, transport, cellular metabolism, and RNA metabolism are dysregulated in breast neoplasia. Sjoblom T, Jones S, Wood L D, Parsons D W, Lin J, Barber T D, Mandelker D, Leary R J, Ptak J, Silliman N and others. 2006. The consensus coding sequences of human breast and colorectal cancers. Science 314:268-74. Contrary to expectation, the pathways containing stable genes were not distinct from those containing dysregulated genes with abnormal copy number. The gene ontologies of 373 stable genes were significantly enriched for known cancer pathways. Cell surface receptor-linked signal transduction (42.9% of stable gene set; $p=2.16e^{-41}$), followed by intracellular signalling cascade (31.9%; $p=2.55e^{-32}$) and G-protein coupled receptor protein signalling (24.4%; $p=1.35e^{-20}$) showed the most significant enrichment. Additionally, positive regulation of catalytic activity ($p=2.59e^{-26}$), regulation of cell proliferation ($p=1.35e^{-20}$), protein amino acid phosphorylation ($p=5.84e^{-19}$), regulation of macromolecule metabolic process ($p=1.90e^{-12}$), regulation of cell motion ($p=1.58e^{-8}$), anti-apoptosis ($p=5.08e^{-4}$), and regulation of epithelial cell proliferation ($p=0.02$) were significantly enriched. These functions are associated with tumor cell survival, proliferation, repair, and regeneration.

Replication of Findings.

Results were replicated using an independent data set of tumor-normal pairs analyzed for both copy number and expression (Chin, et al., 2007; Naderi, et al., 2007). Of the 7,692 protein-coding genes with stable copy number, 3,589 did not exhibit differences in expression. These genes were represented in 150 enriched pathways, 95 of which were shared by the Hicks et al., (2006) ($n_1$) and Chin et al., (2007) ($n_2$) datasets (Table 5 contains a list of these genes). The most significant pathways common to both analyses included MAPK signalling ($n_1=74$, $n_2=67$), regulation of actin cytoskeleton ($n_1=64$, $n_2=50$), Wnt signalling ($n_1=52$, $n_2=40$), insulin signalling ($n_1=50$, $n_2=37$), VEGF signalling ($n_1=23$, $n_2=14$), apoptosis ($n_1=22$, $n_2=17$) and glycolysis/gluconeogenesis ($n_1=21$, $n_2=23$) (Supporting Information Table S6). This study revealed 325 gene ontologies enriched for stable genes ($n_2$; $p \leq 0.05$), with 183 gene ontologies shared with the above gene set ($n_1$) (Supporting information Table S7).

The composition of the dually stable gene set was supported by several other replicate genomic and expression breast cancer studies from the Cytognomix databases. A high throughput, sequence-based genomic analysis (Stephens, et al., 2009) identified 130 genes mutated in 2 or more tumors (~10% for n=24). However, only 20 of these genes were present in the stable gene set (Supporting Information Table S8). The deduced dually stable gene set was also compared with the COSMIC and Cancer Gene Consensus Databases of mutations. Of the genes that are commonly mutated in breast cancer in these databases, 8 were present among the deduced set of stable copy number and expressed genes. Furthermore, differentially expressed genes in 5 independent series of paired breast tumor-normal GEO datasets (see Methods) identified 69 differentially expressed genes in 2 or more series among the 5,804 stably expressed genes with normal copy number (Supporting information Table S8). After accounting for unstable or mutated genes present in the combined GEO, COSMIC, Cancer Gene Consensus, and high throughput tumor sequencing data, the number of dually stable genes deduced from Hicks et al., 2006 and Turashvili et al., (2007) was reduced by 1.6% (n=96) to 5,708. Intersecting the above data with Chin, et al., 2007 and Naderi, et al., 2007, the combined unstable or mutated gene datasets reduce the number of dually stable genes by 1.7% (n=66) to 3,793. The low numbers of unstable genes in the replicates overlapping the deduced stable sets suggest that this core set of stable genes will be present in the majority of breast tumors.

Example 3

Stable Gene Products as Targets for Breast Cancer Therapy

A common set of dually stable genes is more likely to be functional in a plurality of tumors. Their products may represent potential therapeutic targets, since drugs acting upon them would be effective in a preponderance of tumors. These gene products are thus plausible targets for systemic breast tumor chemotherapies that are approved because of their efficacy in ablating tumors in the maximum number of patients. Genes encoding these targets would thus be maintained as an ensemble in the breast tumor genomes, since drugs would be expected to disrupt multiple functions or pathways containing them.

Of the 68 agents commonly used in breast cancer treatment, 24 of them target proteins encoded by dually stable genes (Table 3). Genomic stability of the 3 genes tested (CSF1R, FLT4, and GMPR2) was confirmed by metaphase FISH (Supporting information Table S5). Pathways containing each of these gene products included metabolic processes (e.g. purine, pyrimidine metabolism and glycolysis), inflammation (natural killer cell-mediated cytotoxicity and gamma R-mediated phagocytosis) and cellular interactions (neuroactive-ligand receptor interactions, endocytosis, focal adhesion and cytokine-cytokine interaction). The context of these drug targets showed a broad distribution of biochemical pathways. In some instances, these targets occurred at the intersection of multiple pathways; for example, glycolysis and gluconeogenesis are enriched for stable gene products (p=0.000117). Among these products, glucokinase is an investigational target for potential breast cancer therapy because of increased energy requirements of tumor cells. Pelicano H, Martin D S, Xu R H, Huang P. 2006. Glycolysis inhibition for anticancer treatment. Oncogene 25:4633-46. Warburg O. 1956. On the origin of cancer cells. Science 123:309-14. Lu W, Huang P. 2010. Glycolytic Pathway as a Target for Tumor Inhibition. In: Bagley R G, editor. The Tumor Microenvironment Springer. p 91-118.

In some instances, multiple dually stable gene products were targets of the same drug and are members of the same pathways. For example, FLT4, KDR, CSF1R, and RET comprise four of nine known drug targets of sunitinib. FLT4, KDR, and CSF1R belong to signalling pathways characterized by cytokine-cytokine receptor interactions, focal adhesion, and endocytosis. These genes also contribute to vascular development, VEGF signalling and hematopoiesis, both of which are essential for tumor growth. Folkman J. 2006. Angiogenesis. Annu Rev Med 57:1-18.

TABLE 3

Drugs Used In Breast Cancer Therapy That Act On Stable Gene Products*

| Drug: No. of Targets | Stable Drug Targets | Associated Pathways |
| --- | --- | --- |
| Azathioprine: 12 | GMPR2 | Purine metabolism |
| | AMPD3 | Purine metabolism, metabolic pathways |
| Cetuximab: 12 | FCGR3B | Natural killer cell mediated cytotoxicity, *Leishmania* infection, systemic lupus erythematosus |
| | FCGR2A | Fc gamma R-mediated phagocytosis, *Leishmania* infection, systemic lupus erythematosus |
| Cyanocobalamin: 11 | TCN2 | N/A |
| | MTRR | N/A |
| | MMACHC | N/A |
| Dasatinib: 10 | ABU | ErbB signaling pahtway, cell cycle axon guidance, neurotrophin signaling pathway, pathogenic *E. coli* infection, pathways in cancer, chronic myeloid leukemia, viral myocarditis |
| | YES1 | Tight junction, adherens junction |
| Docetaxel: 2 | BCL2 | Apoptosis, neurotrphin signaling pathway, amyotrophic lateral sclerosis, pathways in cancer, colorectal/prostate/small cell lung cancer |
| Estradiol: 4 | SHBG | N/A |
| Estrone: 5 | SHBG | N/A |
| Fluvoxamine: 3 | HTR1A | Neuroactive ligand-receptor interaction |
| Folic Acid: 5 | SLC25A32 | N/A |
| Gemcitabine: 3 | RRM1 | Pyrimidine metabolism, purine metabolism, glutathione metabolis, metabolic pathways |
| Irinotecan: 2 | TOP1MT | Panther pathways: DNA replication |
| Losartan: 1 | AGTR1 | Calcium signaling pathway, neuroactive ligand-receptor interaction, vascular smooth muscle contraction, renin-angiotensin system |
| Mercaptopurine: 12 | GMPR2 | Purine metabolism |
| | AMPD3 | Purine metabolism, metabolic pathways |
| Paclitaxel: 2 | BCL2 | Apoptosis, neurotrphin signaling pathway, amyotrophic lateral sclerosis, pathways in cancer, colorectal/prostate/small cell lung cancer |
| Sertraline: 3 | HTR1A | Neuroactive ligand-receptor interaction |
| Sulfasalazine: 2 | ACAT1 | Butanoate metabolism, lysine degradation, pyruvate metabolism, benzoate degradation via CoA ligation, fatty acid metabolism, propanoate metabolism, valine, leucine and isoleucine degradation, synthesis and degradation of ketone bodies, tryptophan metabolism, terpenoid backbone biosynthesis, metabolic pathways |
| | FLT4 | Cytokine-cytokine receptor interaction, focal adhesion |
| | KDR | Cytokine-cytokine receptor interaction, focal adhesion, VEGF signaling pathway, endocytosis |
| Sunitinib: 9 | CSF1R | Hematopoietic cell lineage, cytokine-cytokine receptor interaction, endocytosis, pathways in cancer |
| | RET | Panther pathways: Endothelin signaling pathway, heterotrimeric G-protein signaling pathway-Gi alpha and Gs alpha mediated pathway, metabotropic glutamate receptor group I pathway |
| Topotecan: 3 | TOP1MT | Panther pathways: DNA replication |
| | ABCG2 | ABC transporters - General |
| Trastuzumab: 13 | FCGR3B | Natural killer cell mediated cytotoxicity, *Leishmania* infection, systemic lupus erythematosus |
| | FCGR2A | Fc gamma R-mediated phagocytosis, *Leishmania* infection, systemic lupus erythematosus |
| Venlafaxine: 5 | HTR1A | Neuroactive ligand-receptor interaction |
| Warfarin: 3 | VKORC1L1 | N/A |

*Drugs used in breast cancer treatment (from PharmGKB) along with the number of genes they target. Some of these drugs may not be used for killing tumor cells. Gene names of targets that are stable by copy number and expression data are reported along with associated KEGG biological pathways unless otherwise specified. N/A refers to not available.

Inhibition of KDR decreases tumor growth and angiogenesis. Shao R, Bao S, Bai X, Blanchette C, Anderson R M, Dang T, Gishizky M L, Marks J R, Wang X F. 2004. Acquired expression of periostin by human breast cancers promotes tumor angiogenesis through up-regulation of vascular endothelial growth factor receptor 2 expression. Mol Cell Biol 24:3992-4003.

GMPR2 and AMPD3 are also members of common nucleoside metabolic pathways which are targets of azathioprine and mercaptopurine. GMPR2 and AMPD3 are both components of purine and pyrimidine metabolism. $F_c$ receptors encoded by FCGR3B and FCGR2A are targets of cetuximab and trastuzumab, and belong to the same pathways associated with natural killer cell mediated cytotoxicity and $F_c$ gamma R-mediated phagocytosis. Anti-tumor effects of monoclonal antibodies are dependent on immune activation through these receptors. Clynes R A, Towers T L, Presta L G, Ravetch J V. 2000. Inhibitory Fc receptors modulate in vivo cytoxicity against tumor targets. Nat Med 6:443-6. Stavenhagen J B, Gorlatov S, Tuaillon N, Rankin C T, Li H, Burke S, Huang L, Vijh S, Johnson S, Bonvini E and others. 2007. Fc optimization of therapeutic antibodies enhances their ability to kill tumor cells in vitro and controls tumor expansion in vivo via low-affinity activating Fcgamma receptors. Cancer Res 67:8882-90.

Based on the independent replication dataset (Chin, et al., 2007; Naderi, et al., 2007), 5 of the 24 dually stable gene targets were also targets of venlafaxine (HTR1A), mercaptopurine (GMPR2), azathioprine (GMPR2), sertraline (HTR1A), fluvoxamine (HTR1A), sunitinib (KDR), and topotecan (ABCG2).

Approach for Determining Effective Chemotherapy Agents

Certain anti-breast cancer therapies have been evaluated in the NCl-60 panel of cancer cell lines (Staunton J E, Slonim D K, Coller H A, Tamayo P, Angelo M J, Park J, Scherf U, Lee J K, Reinhold W O, Weinstein J N and others. 2001. Chemosensitivity prediction by transcriptional profiling. Proc Natl Acad Sci USA 98:10787-92.) including four cell lines we studied (MCF7, MDA-MB-231, HS578T, and T-47D). We have confirmed stable copy numbers for a representative group of target genomic intervals in 5 breast cancer lines (MCF7, MDAMB231, HS578T, T47D and SKBR-3). Despite the lack of stratification in pathology in the tumors studied, genomic architectures and functions were preserved in these regions. Paclitaxel and its derivatives, estrone, estradiol, and topotecan are common therapies that act on multiple products encoded by dually stable genes which may, in part, explain why they are effective for inhibiting growth of these cell lines and for treating breast cancer.

Based on these data, preservation of stable, essential genes is generally related to the effectiveness of breast cancer chemotherapeutic agents that act on one or more stably encoded gene products; and 2) that drugs acting on stable gene targets are more effective at selectively inhibiting tumor growth when they are intact in the genome Some approved agents are considered effective because they target functional pathways or gene products that are operative in the majority of tumors. For example, Herceptin, which is commonly used as an example of personalized neoadjuvant chemotherapy, would be an exception to this concept because it targets a gene amplification present in only ~20% of cases.

By examining genotypes (copy number, expression, point mutations) of stable target genes and partners they interact with in breast cancer, growth inhibition by chemotherapies known to target certain stable gene products can be related to genotype. Although the data in Table 4 represent breast cancer cell lines, one of skill in the art can appreciate that the same strategies and interpretation of findings would be applicable to the tumors from which breast tumor cell lines have been derived, and by extension, breast tumors from patients, in general. Nevertheless there are exceptions in the data shown in Table 4 that obviate the concept that all patients harbor stable, intact copies of these genes. Mutations in these stable target genes to reduce or abolish their expression make them less suitable as targets for chemotherapy. There is evidence of differences between 'replicate' GI50 assays with the same drug in certain cell lines. For example, Gm showed significant variability in T47D and HS578T that was not evident with the other lines. After mutation analysis of these targets, the drugs can be used in combination at concentrations (optimized for individual drugs) to determine if there are synergistic or additive effects of the drugs on cell killing. Drug combinations consisting of one with low GI50 in a cell line (due to a loss of function mutation) can be rescued by treating with a drug with a high GI50 (and different target gene and no mutation). For example, if HS578T has inefficient growth inhibition with To (−log 10M mean concentration of 4.55, Table 2) and there is no mutation in To targets or associated partner genes then To with Pa (−log 10M mean concentration of 8.5, Table 2) might be better than either alone. If however, there is a mutation in To gene targets (TOP1MT, ABCG2), then To treatment should be no more effective at growth inhibition than Pa alone. The drug combinations can be determined based on the efficacy of cell killing and the presence or absence of mutations in drug targets as determined in the instant invention.

TABLE 4

GI50s* of 5 Breast Cancer Cell Lines from NCI60 Panel

| Drug | BT549 | HS578T | MCF7 | MDA231 | T47D | CV | Targets | Associated KEGG Pathways |
|---|---|---|---|---|---|---|---|---|
| Me | 4.52 | 4.85 | 5.78 | 4.61 | 5.45 | 0.10 | GMPR2 | Purine metabolism |
| Me | 3.74 | 4.84 | 5.74 | 5.14 | 5.62 | 0.14 | AMPD3 | Purine metabolism, |
| Me | 4.00 | 4.85 | 5.82 | 4.61 | 5.45 | 0.13 | | Metabolic pathways |
| Pa | 7.60 | 8.22 | 8.01 | 7.27 | 7.27 | 0.05 | BCL2 | Apoptosis, NS pathways, |
| Pa | 8.45 | 8.52 | 8.53 | 7.91 | 6.91 | 0.08 | | ALS, pathways in cancer, |
| Pa | 9.30 | 8.81 | 9.06 | 8.56 | 6.56 | 0.12 | | colorectal/prostate/SCLC |
| Gm | 7.80 | 5.65 | 7.99 | 5.86 | 6.26 | 0.15 | RRM1 | Pyrimidine & Purine metabolism, |
| Gm | 8.00 | 4.00 | 8.00 | 6.28 | 8.00 | 0.23 | | Glutathione metabolism, |
| Gm | 8.00 | 4.00 | 8.00 | 6.03 | 5.86 | 0.24 | | Metabolic pathways |
| To | 7.36 | 5.96 | 8.09 | 6.41 | 8.24 | 0.13 | TOP1MT | DNA replication |
| To | 7.05 | 5.14 | 7.79 | 5.67 | 7.82 | 0.16 | ABCG2 | ABC transporters (general) |
| To | 7.32 | 5.73 | 7.83 | 5.65 | 7.73 | 0.14 | | |

*Drug concentrations are $-\log_{10}M$ units, Me, mercaptopurine; Pa, Paclitaxel; Gm = gemcitabane; To, topotecan; CV, coefficient of variation of GI50s; KEGG = Kyoto Encyclopedia of Genes and Genomes; NS, neurotrophin signaling; ALS, amyotrophic lateral sclerosis; SCLC, small cell lung cancer; cell line MDAMB231 is abbreviated to MDA231; gene names are italicized. Data extracted from Ring et al, 2008.

For example, the MCF7 and BT549 cell lines are more sensitive to Gm than HS578T. This could be explained by stability of the drug's target gene and/or associated genes for MCF7 and BT549, but these genes will be normal in HS578T. The sequence, copy number and expression of one or more drug targets would harbor a mutation in the lines (or tumors) that show diminished drug response. Mutations are identified by sequencing, and significant reproducible copy number or expression changes are derived from the array comparative genomic hybridization and expression data. In other cases, inactivating or leaky point mutations may occur in combination with copy number changes, such as unmasking a recessive allele due to loss of heterozygosity at a target gene locus. If point mutations are not found, copy or expression changes are detected in known targets, other potential targets, whose functions, complexes or enzymatic products are required for the activity of the target are examined. These include other proteins encoded in the same pathway as the drug target (ie. epistatic), genes in pathways that produce potential cofactors for drug target activity, or other components of multi-subunit complexes that may be associated with the stable drug target. Pathway software (eg. multiple public resources such as KEGG, Reactome, Panther, Ingenuity are available) identifies potential candidates that harbor mutations affecting metabolism or efflux transport of the selected drugs in less sensitive cell lines. Copy number, expression and mutations in these associated genes are assessed using the same procedures that are applied to analyze the drug target genes themselves.

If the drug targets an essential, stable gene product, then higher concentrations of drug are likely to be required to kill the cell for target genes located in hyperploid genomic intervals with additional gene copies, assuming that the gene is not subject to dosage compensation. If the drug targets a gene product for which alternative pathways exist to produce key substrates (e.g. de novo and salvage pathways for purine synthesis), then mutations in a target gene will drive synthesis through the alternative pathway. In such an instance, a mutation which inactivates a salvage pathway target will require increased drug concentrations for inhibition.

While unlikely, if no mutation, copy number or expression change can be detected in any of the suspected target genes or associated loci, then either (a) mutations are not recognized as deleterious because the predictive mutation analyses lack sufficient sensitivity and specificity, (b) mutations reside in unstable regions of the genome, or (c) the effect is transient and based on epigenetic differences between cell lines. This seems unlikely as the GI50 indices were generally reproducible. If the GI50 values are not reproducible between different assays of the same cell line, an epigenetic explanation may be correct. If the mutations reside in unstable regions, copy number, expression and sequence differences between cell lines with higher GI50s relative to those with lower GI50s are examined. For example, To has 3 target gene products of which 2 are stable, Pa has 1 of 2 targets, Gm has 1 of 3 targets and Me has 2 of 11 targets. Associated unstable target genes, including members of the pathways in which they reside are also analyzed. Against the background of pre-existing mutation or copy number expression changes, such differences reveal diagnostic genotypes which are likely to be associated with lower efficacy of a drug.

Genes mutated in drug resistant cell lines (high drug concentrations) will also be susceptible to inhibition by targeted shRNA therapy in tumors without these mutations. If cells containing the silenced target gene are not inhibited to the same degree as in the mutated tumor, then cells may be employing an alternative pathway to produce the metabolites that are thought to be limiting due to the action of the drug. Changes in the levels of intermediates produced by alternate pathways should be an effective strategy to dissect the significance of associated gene products in the same pathway or which bind to the primary target.

This approach has the potential to predict drug efficacy based on the functional status of stable drug targets in individual patients (aside from the contributions of other established pharmacogenetic mechanisms).

TABLE 5

Dually stable genes common to both the Hicks/Turashvilli AND Chin/Naderi datasets DUOXA1, HIF3A, RNF10, NCBP1, HIST1H4E, HSPA4, REM1, HSPA9, HSPA8, SSFA2, LGALS3,
B2M, INSL3, EMILIN2, PMM2, HIST1H4G, ASS1, RNF11, ZNF708, HSPA5, ZNF703, ZNF701,
ZNF700, PIK3CG, ZC3H10, CRBN, ZSWIM1, ZSWIM2, HMGCLL1, GRIN1, ABCD2, TMEM53,
CBLC, PPHLN1, ZNF45, TCOF1, JRKL, NUP98, MUC7, ZNF682, PPP2R2C, MUC4,
OPA3, IREB2, PIK3C3, RAB40C, BEST4, ZNF677, ZNF675, ZNF671, PARP16, MAX, WHSC2,
MAZ, PARP10, CSN2, CSN3, CTBP2, C10orf25, MAL, C10orf27, KIAA1274, ATP2A1, ITGA2,
ITGA4, RIT2, SIM1, TRHR, PDCD10, GTF3C1, DOLPP1, GTF3C4, IQSEC3, ADH1B, LILRB5,
LILRB4, XPO4, LILRB1, XPO6, DGAT1, DGAT2, AGPAT5, FBXL13, HRH2, CYP27B1, HRH1,
JAGN1, KCNIP1, SLC35D3, GRP, TLCD1, CHST8, COL4A4, COL4A3, GTF2IRD2, SLC35D2,
GART, CD83, ANAPC5, GATAD2A, RPS6KA4, WFDC2, TP53I13, ATAD1, PSMD13,
PSMD12, SLC28A2, C9orf119, ITGAL, GIT1, GIT2, HLF, MINPP1, C9orf116, C22orf26,
GANAB, TRERF1, SESN3, SMAD6, SMAD7, RIC3, SMAD2, SMAD3, SHROOM3, MUS81, SHROOM1,
FOXM1, ZWILCH, GRHL1, TMPRSS11B, CEBPG, TMPRSS11D, TMPRSS11E, PELI3,
ZSWIM5, ELL2, SLC36A1, SPARC, C16orf63, MRPL50, C14orf119, ART3, MYEOV, DRAP1,
MYLK2, SULT1A2, COX4I2, COX4I1, PRKAR1A, PRKAR1B, SH2B1, NOL7, PQLC3, SRPK2,
RAB11FIP3, CRTAM, SCLY, PIPOX, CCDC115, MCF2L, FAM124B, CCDC111, LEO1, SPP1,
CLPTM1, ATP1A1, MYL6B, CTHRC1, DHX8, SPHK1, IPO11, CALCRL, ACTR10, CPEB4,
HMGB1, PGLYRP2, ZNF264, ZNF689, CHAF1A, PDDC1, ABAT, CDH20, ZNF780A, IFT81,
RDH5, IFT88, ANGEL2, DPYS, ACTL7B, ACTL7A, CDCA5, HOMER3, KIAA1529, GFAP, DEPDC7,
EIF1B, PRICKLE1, NUP93, CD40, CA11, FPGS, SP6, CRB2, SASH1, MOGAT2, SLC34A1,
GPT2, ALKBH2, GLRA1, LYPD1, DZIP1L, OR5P3, OR5P2, PNN, TCHP, ATP6V0E1, CHID1,
SPG11, STAM2, WDR77, ZNF43, RPN1, QTRTD1, AMHR2, IQCE, NTAN1, SIDT1, KRT77,
CATSPER1, SFMBT2, CHI3L2, CYP4F2, ARL2BP, TMC4, ASB1, ATG3, PRL, CLOCK, RGS6,
RELN, LRRC41, C8orf55, C2orf50, KNDC1, MRPL37, MRPL35, MRPL30, C4orf14, RFFL,
C4orf17, PTH2R, KLK1, KLK2, KLK3, KLK4, KLK6, KLK7, KLK8, CHFR, FAM120AOS, SYPL1,
DBH, RAB27B, FAM45B, RFX4, CSAD, RGS9, SNN, FAM81B, TMEM49, MTRR, PAK4, STXBP5,
DBT, SFRS2IP, CEPT1, ZNF354B, GGCX, RCCD1, ZNF57, COPS2, KCNG2, C11orf1,
CCDC52, COPS4, ASTE1, C19orf44, ZNF596, GABRA4, C17orf64, ZNF599, PANX2, ESPL1,

TABLE 5-continued

Dually stable genes common to both the Hicks/Turashvilli AND Chin/Naderi datasets ZNF600, ITIH2, ZNF607, RPRM, OR1Q1, DEFB118, DEFB119, FECH, LCN12, C10orf54,
RHBDD2, TRAF3IP1, C10orf53, TCF4, TCF7, KIAA0831, ARID2, C11orf9, NUDT3, NPFFR2,
NUDT5, DNAJB8, IGFBP6, IGFBP5, EPS8L1, EPS8L2, EPS8L3, AFP, GJA1, BSND, GJA3,
PROZ, GJA8, DHX40, CALML5, COX19, NUBP1, BTC, COX11, ZNF114, TRIM5, TRIM7, HPN,
MDN1, ZNF337, ZNF334, ZNF335, ANKRD13B, TMC1, ZNF331, AMPD3, CD248, AMPD1, TMC8,
KIAA1462, TEX12, CYLC2, TMSB10, PPA1, C20orf54, LRRC3B, MCTP1, MCTP2, AREG,
ECD, TMEM14C, NOTCH2NL, TPM4, WDR24, TPM1, RPS6KB2, FBXW8, CIB3, CIB1, MCART1,
THYN1, C22orf30, FBXW5, KIAA1683, TRIO, NTF3, MTMR11, UPP2, UGDH, SEPHS2,
KRTAP2_1, KIAA0020, ITGA5, NUP155, TMEM143, TMEM141, FOXL1, ITGA7, C6orf168,
TMEM149, ATXN2L, CST6, LRRC32, LRRC34, OR7A5, SLC39A5, PPAT, SH3PXD2B, ZSWIM3,
TUB, KIAA1191, SVIL, TATDN2, SAPS2, LYSMD2, DCXR, PRDX1, C19orf20, C19orf21,
C19orf26, ZNF470, C19orf24, SMOC2, SMOC1, LRP2BP, ITGB1BP3, POMZP3, ZNF7, FAM90A1,
ZNF2, AXIN1, TIPIN, MMRN2, SDCBP2, ZNF8, C11orf17, C11orf16, TOR1A, TRPM6,
ARSG, PURG, CCT6B, ST3GAL1, RAB1B, NINJ2, RUFY2, GALNS, ZNF451, NLE1, LNPEP,
TRPM7, GIP, PBX3, FAM111A, SYT14, DPH2, DPH5, SLC16A1, SLC16A3, SLC16A4, SLC16A6,
TUBG1, TUBG2, ABRA, BCKDHA, PTCH2, C9orf30, C9orf37, RAD9B, RAD9A, CD33,
CD34, CD36, CD37, TXNDC8, FXYD5, POLR3A, OR51B5, OR51B4, B3GAT1, OR51B6, TXNDC5,
POLR3K, POLR3H, OR51B2, GPS1, GPAM, CALM3, TTC30B, CALM1, LIX1, DCC,
PLK1, TAF4B, PERP, DLGAP5, EIF4ENIF1, CUL7, WDR66, FBXL14, PRMT8, HOXD8, HOXD9,
PRDM7, PRMT3, PRMT1, CDH24, HOXD1, CREB1, SLC25A4, FLRT1, PER2, BRD8, BRD7,
BRD1, SLC15A4, BRD3, KIAA0427, SETD1A, SIPA1L1, ORMDL2, PTPN12, PTPN11, PTPN14,
ZNF787, GALR1, TTC16, GDF11, SMARCA4, TTC18, C8orf30A, C16orf75, C16orf72,
ZNF221, GNAO1, GAB4, RRAS2, NTSR2, GAPDH, C4orf26, DMRTB1, ARHGAP9, NPTX1,
ZFP91, ZSCAN4, RPL18, ZSCAN1, ARHGAP1, PPM1E, PPM1D, SOLH, HOXA6, USP45, HOXA5,
RNF130, DNAJB12, PRLH, PPP6C, RNF135, MADCAM1, TMEM71, TTC9B, TMEM74,
SLC39A12, CLNS1A, PRKAB1, TSHZ3, SLA, SGSH, LASP1, ZNF581, ZNF580, ZNF583, ZNF582,
MRPL2, RPUSD1, ZNF587, MRPL1, SCRN2, RG9MTD2, RG9MTD3, GINS2, ZNF610,
ZNF613, ZNF615, ZNF322B, ZNF616, NANOS1, ACAD9, CYP2E1, STUB1, HOXC12, NPBWR2,
RBCK1, LRCH3, C10orf47, MBD3L1, FSTL4, BAG2, PTDSS2, MYO1E, ADH1A, ADAMTS10,
PDCD1LG2, ADAMTS12, LRRC37A2, LRRC37A3, ADAMTS16, VDAC3, VDAC1, LRRC56,
CHST3, CSDC2, OAS1, CNTD2, ANAPC2, PGBD3, NUFIP2, TNK2, HOXA13, SLC34A3,
HOXA11, HOXA10, PPBP, PSMA1, SF3B4, C3, SLC6A12, PSMA8, HIST2H2AA3, SLC6A17,
TSSK6, ZNF324, TSSK4, ZNF326, GALNTL1, GALNTL2, GAL3ST3, ZNF329, SH3BP5L,
EIF2C2, SNRPB2, CS, KCNH1, CP, RMND5B, KCNJ3, KCNJ2, C14orf93, TSTA3, RPS6KC1,
ADRB1, ADRB2, C9orf135, AGPAT2, WAPAL, TRNT1, BLOC1S3, MCM3AP, PLAUR, LDHAL6B,
LRRC27, LRRC25, LACRT, KIAA1033, PEX12, BBC3, ALDH1A2, ALDH1A3, CDC37L1,
RAB3IL 1, SORBS2, GCNT1, DNAJB6, GCNT2, NANS, CALCOCO1, CALCOCO2, TAC3,
KIR2DL1, CATSPER3, SLC16A14, GLT25D1, PLAG1, CCR10, LRRC45, SMARCB1, FLOT2,
PIGG, PIGH, COG7, DKKL1, AADAC, ILKAP, KIAA0494, C19orf33, PIGX, SERTAD4,
PIGZ, C19orf39, DMBX1, WFDC11, WFDC12, SERPINB8, C1orf59, MPPED2, ABHD8, C11orf24,
FOXC2, SERPINB2, RDM16, RDM12, RDM13, COL6A1, WBP2, COL6A2, DEDD2, SEC61A1,
ALPL, FXYD7, DDHD2, KLK12, KLK13, C3orf37, OGFOD1, KLK15, ZFAND5, CREBL2, ABHD3,
TARSL2, C14orf105, ENOSF1, MAFG, MMP11, ZNF460, SLC39A10, PI3, HSPD1, SERPINB5,
GHRL, C3orf31, RSBN1, HSP90AB1, ARHGAP22, RWDD4A, ARHGAP20, ARHGAP27,
SAP18, ARHGAP24, PPP1R16A, PLLP, ZSCAN22, DNAJC13, CD28, MICALCL, SLCO4C1,
CD22, TDRD1, ARHGDIA, CD27, MRPS2, C9orf21, TSEN54, RBP3, RBP5, NANP, ABH
D2, UBR2, NUCB1, PA2G4, BMP6, GPR1, BMP4, BMP3, ORC2L, PPP2CA, ACSL3, EEF1D,
ACSL1, SERHL2, ACSL5, GABRG1, PSG9, PSG6, AATF, PSG4, PSG5, PSG2, CCNI, C20orf165,
HOXC9, PRKCI, TRIM38, PTOV1, RUNDC2A, OLFML3, TRIM37, RASSF4, RASSF7, FEN1,
HCST, LUC7L, RSAD2, NCKAP1, KLRC4, CHD1, CYGB, CHD4, MRP63, PLEKHJ1, WISP1,
ABHD12, HINT1, ZNF585A, NGRN, ERMAP, C3orf59, C3orf58, RCN3, IL4R, RCN1, CDC25C,
ATP10D, OR52A1, RNF43, CAPS, POLR2E, WFDC8, POLR2G, POLR2B, RHOC, POLR2L,
PTGES, ACO2, RHOG, C20orf160, SUV420H2, POLR2J, CES1, PLSCR4, LRIG3, LRIG2,
TMEM61, TMEM60, MPO, USP54, PELI2, ARL5B, TMEM68, PRODH, SNCG, SNCB, BATF2,
RNF126, IL17RE, PSG1, RNF122, MCPH1, GRPEL1, GRPEL2, SOST, CCDC109A, CXCR4,
ZNF627, CDC34, FAM120A, DDIT4L, FFAR2, MAPK10, MAPK12, OPN4, UCP2, FZD2,
TEK, BTG3, FZD6, FZD7, NET1, ZNF625, CACNB1, TEC, CYP2B6, ZNF621, ZNF623, C4orf36,
UGT2B15, C4orf34, C4orf35, FUT11, OLFML1, CTNNA3, EBF3, RAP2B, MAMDC2, HOXC4,
LYZL4, C10orf99, LYZL6, C15orf48, C15orf44, C10orf91, C10orf92, C10orf93, PROX1,
C10orf96, C15orf43, ZNF488, FHOD3, ITFG3, ITFG2, ADH4, ZNF480, C4orf7, TACC2, TACC3,
ZNF484, ZNF485, PIAS2, CTGF, AKR1A1, PRM1, ZNF511, PIAS4, PSMB5, ZNF133, PSMB3,
FZD4, ZNF136, C20orf79, MKI67, RASL12, ZNF317, ZNF318, C20orf72, OVOL2, OVOL1,
P2RX2, P2RX4, CORO6, BCL2L14, TCEB3C, TCEB3B, BCL2L13, TMIGD2, HIGD1A, CRY1,
SFRS1, ZNF556, ZNF554, ZNF555, C22orf15, C9orf142, ZNF551, ACOT11, MSX2, VPS13A,
ZNF558, HSD11B1, ONECUT2, TRAF4, TRAF5, KLB, CDK2AP2, NUP160, ASCC3, ALS2,
ELTD1, TMEM163, CHD2, TMEM165, CACNG1, ALDH1B1, KBTBD3, EVI2B, ABCC12, ABCC10,
LRRK1, PRRT2, GRIN2B, TARBP2, GNA14, GRIN2A, PRLHR, GRIN2D, GNA11, ATF5,
TBC1D10B, PPCS, SH2B3, ZCCHC11, MOV10, PPAP2A, ZCCHC14, C19orf18, PSPC1, ADI1,
IL6ST, SBF1, MOCS2, CAP2, PPWD1, DBN1, UBE2J1, DLG1, ZBTB39, SMG6, DLG5, ATXN7L3,
WDR65, COMMD2, MIB1, COMMD5, FAM114A1, GRWD1, SEMG2, OLIG1, PCBP3,
KPNA2, CTNNAL1, ZMYM5, TAS2R14, PRRG4, CAMK2G, TAS2R10, BCAT2, PTGR2, CRMP1,
OSBPL9, STK4, OCA2, CXCL11, OSBPL3, CXCL13, GRAMD3, OSBPL7, KIAA0776, OSBPL5,
OR13C4, AKAP5, AKAP7, GTF2F1, AKAP3, CD3EAP, AKAP8, MYL4, DNAH10, ATXN1,
ARHGAP15, ARHGAP12, SLC30A9, STARD6, HMGN1, IL7R, TTC5, UGT2A3, NUAK1,
NOVA1, C9orf50, POLR1A, MRM1, POLR1D, CCDC110, RAB3GAP2, CHKB, TMEM132B, DUS1L,
ATP2C1, RASL11A, TNFRSF13C, WDR49, STRN4, ARPC3, STK32B, DIO1, ZIC1, CCL20,
GRM6, GRM7, CCL24, NR1H3, POLR1E, TBC1D2B, HOXB8, HOXB9, CXXC5, HOXB2,
FIBCD1, DST, HOXB1, HOXB6, HOXB7, HOXB4, PPARG, SNPH, PPARA, BRF2, RNF40,

TABLE 5-continued

Dually stable genes common to both the Hicks/Turashvilli AND Chin/Naderi datasets C21orf58, C21orf59, ING2, DCDC2, ZNF354C, C5orf15, GLYATL2, SPDEF, DCUN1D2, INS,
CCDC94, WDFY3, C9orf163, GOSR2, SLC18A2, C14orf37, GOSR1, ECHDC3, PRPF31, TICAM1,
MAP3K1, CACNG6, ACP2, NRN1, KIAA0892, SDCCAG3, RAP1A, RORB, ANKRD32,
LHFPL4, LHFPL5, CUEDC1, TRIM45, NCOA6, NCOA4, NCOA5, WFDC5, TMEM18, IPO13,
NR2F1, ATOH1, DDB2, CD200R1, RHOD, RIMS2, ATOH8, FAM57B, GRID1, ZNF83, GSG1,
ZNF80, ZNF85, ADCK4, SS18, FRMPD1, TRPV4, ST7L, SLC27A4, SLC27A6, SLC27A1, GP6,
IL2RA, ZNF639, ZFYVE20, SCARF1, TAS2R9, SLC17A4, PRRC1, SLC17A6, ZFYVE28, GEMIN7,
SPAG16, SLC17A3, IGLL1, C16orf58, C3orf43, HSPE1, TMEFF1, UGT2B28, PNKP,
ABTB1, C10orf68, PRKD2, C16orf55, NCKAP1L, KRTAP1_1, SLC7A7, CHMP4A, NARG2, BAX,
ZNF497, FAM109B, ERG, ZNF493, SH2D3A, ZNF491, C10orf82, GIPR, ERH, ERAL1, HERPUD1,
LPIN2, MYOD1, PMPCA, RNPEPL1, KLF7, ST5, GPR124, GRIN3B, GPR123, IDH2,
PSMC2, FCGRT, PIP5KL1, KLF9, TMEM40, HEATR4, HEATR3, CYP2R1, INPP5A, SLC24A6,
EVX1, C6orf1, ZNF304, BFSP2, FBN3, REST, ZNF300, TPH1, KLHDC7B, MMP26, SEC61B,
ASCC1, HOXB13, TEAD2, KLRK1, ENDOD1, NUP35, CERK, ZNF544, ZNF547, ZNF546,
SCN1B, C9orf152, ZNF543, HDAC11, CYP11B1, ZNF549, ATP13A3, SLC1A3, FRYL, IDI1, IDI2,
IPMK, DHTKD1, LRRC43, LRRC42, SCRT1, FCGR1B, LRRC46, FOXI1, TMEM175, INHBE,
B3GNT4, DNTTIP1, TMEM100, ZNF214, DYM, TSFM, DHRS7, FNBP4, B3GNT8, ORC6L,
WDR37, MKKS, SLC7A1, ELSPBP1, CDKN2C, CLDN19, BARD1, TPO, DAAM1, GNLY, PCYT2,
SMARCAL1, EDEM2, LEAP2, NMT1, YIF1A, SNAI3, NDUFA4L2, HRC, SYT9, LRRC4B,
SLC2A9, SLC2A8, SLC2A6, RSPO4, SYT4, SLC2A2, SYT6, CNFN, PLAGL2, CLRN1, FAM24A,
FAM24B, TASP1, CD2BP2, RPL37A, NFATC4, CCL4, FUBP3, TIMM10, FUBP1, COLQ,
SPZ1, EXOSC2, VANGL1, IBSP, EXOSC5, ADAMTSL2, SLC1A6, MADD, C1orf115, TULP2,
TULP3, TCP11L2, TULP1, FOXA3, ENG, CEACAM1, CEACAM5, ANGPT2, CEACAM8, RRBP1,
PLEK2, INCENP, FARP2, PALM2, C9orf40, C9orf41, BST2, TCTE3, GTF2IRD1, C9orf46,
MYO5C, MANSC1, F12, KIAA1826, F10, F11, ZNF37A, HDGFL1, KCNV2, SARDH, ATP6V0A1,
ATP6V0A2, CACNB2, VPS53, ALKBH4, SLC1A1, GUCA1A, EEF1E1, GUCA1B, RAPGEF6,
KRT76, PAOX, NODAL, KRT78, STXBP1, RCOR2, STXBP3, RFPL2, TIGD5, ZMYND17,
TIGD6, PDE11A, FLT3, C10orf72, UBTF, PVR, OR4D1, OR4D2, OXSM, CFLAR, FANCE, FGF18,
FANCA, ENY2, UGT2B17, TTC22, CA5A, UBE3C, RCL1, MRPS18C, ELMOD2, C6orf81,
TAOK3, SLC22A17, SKIV2L2, ACOX1, SLC22A12, SLC22A11, HOXA7, TRAPPC6A, TRAPPC6B,
HOXA4, HOXA3, THAP9, RNF141, CDK9, HOXA9, PTK2, LCN1, PDZK1IP1, PTK7, RABGAP1,
ANKRD43, NENF, MGLL, SERGEF, SF3B2, FOXN4, OR7C1, PFDN5, SEMA6D, GAL3ST2,
SEMA6B, ODC1, HDC, PPP3CB, ELAC1, RGL3, ADCK5, RASGRF1, EOMES, ARHGDIG,
DNAJC14, NARFL, MTX2, DNAJC10, C3orf34, MGAT4A, C3orf39, DNAJC19, EDF1, LIAS,
ATP10A, MLN, STIL, PRKCG, HIST1H3B, HIST1H3F, HIST1H3E, UCP1, MLX, FFAR1,
NAT8L, SCML4, BDH1, IFI44, ZNF154, ZNF155, GLDN, NRIP2, RAPSN, GPR135, GPR137,
ZNF91, GPR133, ZNF93, ATP6V1C2, ZNF696, SAC3D1, FBXO18, ZNF614, ACTG1, AAAS,
KRTAP4_4, C10orf90, TPI1, PPIL3, LTBR, MAP3K8, MAP3K9, PPP1R3B, CYP4F12, TRUB1,
CNGB3, CYP4F11, DEAF1, MAP3K7, CCDC92, MAP3K5, ZNF570, ZNF571, TPSG1, ZNF573,
ZNF575, ZNF576, ZNF577, ZNF579, CCBP2, PRTN3, CTSH, SURF6, LYN, KRTAP1_5,
PEX26, FMO5, FPR1, IDH1, CTSC, CTSD, SEMA3C, CCDC78, CTSG, TOMM34, TMEM108,
RPL13, TMEM101, AGXT2, FGFR2, UNC50, TMEM105, CTSW, NME4, NME5, GHITM, GRINL1A,
CXCL5, INPP5F, MOCOS, RAI14, C4orf6, FKBP1A, PRRX2, VPS4B, EMB, DUOX1, KRT1,
VENTX, MATR3, RPH3A, TIMM8B, TRAF3IP3, AP2S1, CYP4F3, CDC16, GDA, KRTAP4_3,
VPS37D, KRTAP4_5, PRKACG, AFF1, PNPLA2, CARD9, CARD8, PNPLA7, ADH6, ERP29,
GUCA2A, GUCA2B, OR5L2, KIAA0195, GFOD1, FRZB, UNC5C, KATNAL1, UNC5D, RASL11B,
MAP1S, KATNAL2, IMMP1L, PWP1, FRMD1, RAD18, C6orf154, GNAQ, UBE2O, ARPC4,
ZNF134, UBE2C, ST8SIA4, ST8SIA3, ST8SIA2, GNAZ, SIX5, WDR70, STX1A, SLC6A11,
PTGFR, LIPT1, PF4V1, RPRML, NIPA1, CHSY1, ALS2CR12, UPF1, C16orf54, CRYGB,
CRYGC, CRYGD, MAGI2, WDR69, PHTF1, LSM3, CPXM2, PDE3B, GPR88, RABEP2, GPR81,
LFNG, MORF4L1, CLEC1A, CCDC134, EPB41L2, NDUFA3, ACSS2, RABEPK, NDUFA9,
MAST2, FLT3LG, ADAM20, ADAM23, FAIM, CD180, LILRB2, WNT3, IL11, GSTM3, CNTNAP3,
LRRN1, PPP1R15A, IL4, C9orf71, BLMH, STX17, C9orf72, STX18, C9orf78, IL8, IL9,
OLFM1, SLURP1, IL23A, CRISPLD2, GPRIN2, GPRIN3, BIRC5, GPRIN1, TTF2, INSR, NOXA1,
TXNL4A, SPTBN4, DAD1, RCHY1, GDF9, KLF16, STK31, TFAP2A, GDF2, TLN2, BCLAF1, GDF5,
P2RX7, CENPF, DEFB129, DPP3, PH6, SUOX, MEA1, ANXA2, ZBTB7A, C11orf68, ZBTB7C,
CEP63, MSI2, MSI1, COQ10B, MNS1, GLTSCR2, COQ10A, MCM6, MCM4, CYP2A7,
PCNT, DKK1, DUSP15, THAP4, KRTAP4_12, FAM53B, FAM53C, DUSP13, FAM53A, SFRS9,
PCP4, RPA1, TENC1, NDUFS1, NDUFS4, WNT9B, NDUFS7, COQ5, A4GALT, COQ6, COQ3,
M6PR, HBM, TIMP3, PEX11G, EPX, PARS2, ELOF1, SFRS3, SIGLEC11, MFHAS1, SFRS2,
CHMP2A, KCNK2, HBZ, ZFYVE1, BOC, ZNF141, DENND2C, ZNF143, DENND2D, ZNF146,
WWC1, SYCE1, THEG, ZNF781, PHC1, COX8A, ZNF784, GPR108, ZNF552, SLC26A10,
SLC26A11, MAGOH, KIAA0355, WSB1, RNASE3, RNASE2, ZNF550, RNASE7, SOD1, FCGBP,
C14orf50, TF, BAMBI, KCNN4, SLC35E1, SEC23IP, ZNF415, OLFM3, BRSK2, CCDC82,
PKIG, CCDC87, H2AFY, H2AFZ, FBXL6, DDX4, TLR3, CTR9, TLR6, ZNF569, ZNF567, ZNF566,
ZNF565, SLC19A3, ZNF215, CCDC64, NCAPG2, ZNF211, SLC7A8, NFKBIB, TRAK2, TRAK1,
NFKBIA, ZNF219, CCDC68, NRXN2, TMEM119, CLTC, PGS1, ARID4A, C10orf128, CEND1,
TMEM116, KCNJ16, CHIA, C7orf31, UBE3B, DACT1, ASB16, SLC35A5, SLC35A1, PRSS35,
ZNF140, NXF1, SDAD1, APH1B, FAF1, PGM5, BZRAP1, HIST1H2BE, HIST1H2BF,
HIST1H2BG, HIST1H2BA, TMEM44, SART3, FGF6, FGF5, FGF4, HIST1H2BI, SEC23A, OLFML2A,
BCAM, VAV1, PHC2, TNFAIP6, CDC23, HOXD13, TNFAIP3, HOXD11, NUP153, PRKRIR,
IPO7, IPO4, NRBP2, PDZD8, KIAA0182, SILV, DEFB1, WBSCR28, ADRBK1, TMEM169,
LRRC15, FYTTD1, LMBR1, RAB8B, GBX2, RAB8A, NANOG, B4GALNT1, NAALADL1, KIAA1598,
SGCB, KIAA1586, SYVN1, MAPK3, DUSP8, MAPK4, PPP1R12C, FOSL1, SPACA3,
DUSP1, DUSP3, NKD1, JMJD5, ICOS, LRRC8A, PYGO1, LRRC8C, LRRC8B, STYXL1, PAQR3,
ATP8A1, OR51E2, EIF4G2, KHDRBS3, NMNAT3, C1orf74, FADS2, SIL1, GPBP1L1, WWTR1,
MSLN, WDR90, METTL4, SYNGR4, STAT5A, PITPNM1, ZIM2, TBC1D13, RFPL3, PRPF38B,
TBC1D14, FBL, KCTD3, OR10A3, C1orf103, PLA2G1B, C16orf3, C21orf63, C21orf62,

TABLE 5-continued

Dually stable genes common to both the Hicks/Turashvilli AND Chin/Naderi datasets ADAM10, ADAM11, LY6D, IKBKAP, PF4, FAM83C, ZBED4, ACAD11, TMEM146, DGKZ,
CPNE9, CPNE8, CREB3L3, CPNE3, NEUROD4, NRAS, CPNE6, CPNE5, C5orf25, GNA15,
C9orf66, ALS2CR8, CNP, TMEM106A, G3BP2, PTGIR, USP12, USP13, U2AF1L4, SNRPN,
USP15, NEK2, SSBP3, SHANK1, USPL1, RHCG, PSME3, UNC45A, RGS9BP, TXNDC12, ZBTB43,
ZBTB45, WDR53, ABLIM1, CAMSAP1, SYNPO, PPP3R2, SMC2, PCSK1, SCG3, MEN1,
PCSK5, P4HA2, JPH3, P4HA1, SLC39A13, HIPK4, SEMA4C, LEMD2, OTUD7B, C10orf116,
NTNG2, HBQ1, C10orf118, ZFYVE16, ATRNL1, PPAPDC3, VN1R1, C3orf19, POFUT2, SP110,
C10orf58, YAF2, ZNF688, TMCO3, VN1R4, ARHGEF17, ARHGEF18, PRKG2, ZNF684,
CCDC90A, DHX29, IQCD, GALNT12, EFCAB4B, SHCBP1, DDX49, CSDE1, STRBP, ISOC1,
DDX41, ZNF175, DDX47, LMLN, ANGPTL4, NPY, ANGPTL2, ZYG11B, ZNF776, KLC2, NLN,
KLC4, MMP14, MMP17, ZNF256, EMCN, AFM, CDKN1C, CDKN1B, CDKN1A, MMP19, UBE2D1,
C14orf43, GTSE1, FAM119B, SETBP1, MLL5, BTBD16, SAP130, COX7B2, IL6, APOE,
CHCHD7, MTHFSD, CHCHD8, LCTL, RFK, OR7A10, ZNF519, RSBN1L, NKIRAS1, NF1,
CMTM5, KIAA0319, HNMT, ZNF514, OR7A17, PUS7L, FOXJ1, FOXJ2, ZNF223, ZNF224, CCDC55,
ZNF227, ZNF189, ACMSD, KCNK15, KCNQ3, NCAPD2, HOXC11, HOXC10, HOXC13,
MMACHC, VEGFA, HCK, SLC39A2, SLC39A3, SLC39A4, BNIP1, SLC39A6, BNIP3, C7orf27,
GZMA, GZMB, CCDC3, GZMM, CABP5, CABP4, GZMH, CABP1, GZMK, FBXO34, C11orf35,
FBXO36, SLC35B2, ZNF350, FBXO31, ZNF420, KIR2DL4, C20orf3, HBE1, ATXN2, ZNF428,
NAB2, MYH11, STIM1, SCMH1, AP3M1, AP3M2, C11orf30, ANKRD13D, MBOAT1, BLVRB,
GPRC5D, HTRA1, TSC1, SPI1, P2RY14, HIP1, DTX3, NEDD4, P2RY13, IFI44L, OR2A4,
BRWD1, KIAA0513, WBSCR16, C17orf82, C17orf80, PPEF2, TIMM9, KIAA0226, IRAK2, FGF23,
ALG10, RIOK2, RIOK1, ORC5L, APBA2, C6orf114, BANF1, SI, GPNMB, SH3TC2, GLS2,
RBM4, DFNB59, B4GALNT3, OCEL1, KIAA0649, ANKRD17, NDE1, SLC38A1, GYG1, HOXC5,
BTD, ATP13A1, C20orf112, VPS28, VPS29, ATP13A5, ATP13A4, ESYT3, TAS2R50, DEFA6,
DEFA5, FTSJ2, SLC45A4, OGG1, PRKRA, FOLH1, C21orf91, WIPI1, APPBP2, CBWD1,
RAB24, LGALS3BP, WFDC10A, TTBK1, NRP1, NRP2, DMXL2, C12orf61, NKPD1, E2F3, EXOC7,
C6orf89, ARSI, CA4, FUT6, FUT5, PPP4C, FUT3, FUT2, MGAT4B, C9orf96, C9orf95,
NXPH4, TUSC5, BRI3BP, SF4, GMIP, TMC6, MIF, GATA6, VTCN1, SLC10A1, TNNC2, TRPM3,
ZDHHC23, USP20, ADAMTS6, ADAMTS2, ARHGEF4, ANKRD13A, GNG13, C1orf84, KIAA1467,
C1orf83, CDH2, C1orf88, CDH7, CENPK, LIPG, SNAP25, FOXE1, RAMP1, EIF2B3,
PEX11A, AMACR, CLCF1, SSH2, PROM2, SEC24C, SSH1, RNASE11, LAG3, KIFC2, PAFAH1B3,
PYY, C10orf125, PYCRL, MBP, SCARB1, AZU1, MRPL47, FANK1, HGFAC, PLEKHA3,
MRPL49, WNT7B, ANXA1, CTPS, LITAF, RFESD, RILP, EMR1, ZNF692, SEC63, OR1I1, C16orf7,
CNTN6, TRIB2, TRIB3, DHX32, DHX34, DHX36, DHX37, MPHOSPH9, METT5D1, ZNF169,
MT1X, RUVBL2, DDX52, U2AF2, B3GNTL1, NEK8, DDX55, VN1R2, MT1M, CDC42BPG,
MT1H, ZNF768, SF3A2, GPR162, MT1E, MT1F, MT1G, KLB1, ZNF180, QPRT, LACTB,
UBE2E1, ZNF25, CNGA1, SHB, MLF2, CCDC7, SHF, ZNF22, COX7A1, CCDC8, CCDC9, ZNF28,
EPOR, EGLN2, NASP, PLA2G10, DNAH7, DNAH5, TBP, SH3TC1, LYNX1, C11orf46, RPL7L1,
CCDC96, ZNF503, OR1J4, OR1J2, PROSC, ZNF506, NUDCD1, CPNE4, ZNF239, CCDC48,
UBL4B, ZNF235, ZNF233, ZNF230, GPBP1, EID2B, SAMD4B, C3orf32, COASY, DUSP16,
CRELD1, ACVR1C, MRGPRX4, ZDHHC24, CDKL2, USF2, RANBP9, ZNF346, ZNF345,
ZNF432, ZNF34 7, ZNF439, ZNF438, VGLL4, ZNF430, PUS1, KIAA0430, RALGDS, FGD3,
PUS7, GNB5, GNB4, AIM1, NUDT12, DLL1, DLL3, SATB2, TM6SF2, PIP5K1C, SLC35C2, STX3,
STX5, STX4, C22orf36, PARD3B, GDPD5, CPN2, GPR77, SLC35C1, CRHR1, TGFB1, TGFB2,
PHF12, DYSFIP1, EZH1, C12orf34, SLC5A2, CLEC2B, CCNB1IP1, PRSS7, F13A1, IQGAP1,
PNLIPRP1, C3orf20, DRG1, SPINLW1, SCGB1D1, C6orf106, C6orf105, SCGB1D2,
EVC2, YWHAH, MC4R, AURKC, YWHAB, RUFY3, TCP10L, YWHAG, YWHAE, ZBTB3, TNNT1,
ZBTB1, CARD11, C3orf27, PANK3, CHRM1, CARD14, HRASLS5, HRASLS2, GLRX, GPRC6A,
PXMP2, HTR1F, PSG3, VAMP1, CCNB2, CCNB1, CHST12, WFIKKN2, WFIKKN1, C5orf24,
ABI2, TBC1D22A, ROCK1, CSTF3, TESC, MOSC2, MOSC1, NKTR, TRAPPC2L, KCNE2,
SLC6A1, RAB4B, C1orf123, SLC6A5, SLC6A4, PCCB, SLC6A9, SYMPK, NDUFB3, FCHO1,
KCNE1, IL25, IL29, ZRANB1, PLDN, GPR32, CAV3, AXL, C12orf57, C12orf52, USH2A, LTC4S,
IL12RB1, BTNL8, FMNL1, PZP, C12orf59, IRF2BP1, CLN3, NEXN, C8orf31, C9orf85,
UQCRQ, C9orf82, JAK3, BRCA1, ANKRD44, ANKRD40, VRK3, CRYL1, WNK1, CNNM3, WNK4,
AQP9, NR2C2, SLCO6A1, ACOT8, ACOT6, RFNG, USP32, HBB, SHMT2, ADCY4, OR51I1,
OR51I2, ADCY7, PLD1, MORN3, MPV17L, RNF185, RNF180, IFNK, LRRC31, ZBTB20, FAM126A,
ZBTB25, DOCK8, DDI1, PCYOX1L, DOCK2, ADORA3, GRIA1, MED25, C12orf5, GRIA4,
ENAM, CC2D1B, XRCC1, XRCC2, XRCC5, XRCC6, KRTAP9_8, ZNF71, CLEC7A, LIM2,
KRTAP9_4, SLC9A9, TRIAP1, SCNN1G, TFRC, SCNN1B, SCNN1A, HOXB3, PARD6G,
NARF, C16orf78, TM4SF20, PLCB1, RIC8A, POM121, CYP4Z1, NHLRC2, RALGPS1, PARP2,
ESPNL, BTNL9, F2RL3, C8orf41, TP53INP2, LAMC3, PRLR, GPHN, SCUBE3, ESR2, GSTT1,
ZNF135, CD274, MRPS25, MRPS22, CDC14B, CDC14A, ITSN1, CTSL2, PPP2R5D, PPP2R5E,
IL13, FGF22, PPP2R5A, PPP2R5B, INSIG1, KIAA0652, ZNF32, CTNND2, TBX4, KCNA6,
KCNA7, KCNA5, KCNA2, KLRF1, TMEM38A, GNB2L1, ZNF536, HACE1, ZNF530, THOP1,
SLC10A4, PAN3, CSNK1D, SPHK2, OTOR, FTH1, KDR, RPS24, QSER1, ACACA, ZNF785,
C3orf36, NDN, FOXD4, GPR107, SLFN11, SLFN12, SLFN13, ALDH7A1, GAS8, RAD51C,
DBR1, SLC5A1, ZDHHC6, HSD11B1L, CAPN12, PRRT3, PYGM, LILRA3, SLC5A3, SP140,
ZNF408, PPIF, SURF1, CCDC85B, SARS2, RNMTL1, GLYATL1, CYFIP1, GFI1B, CORO1B,
CORO1C, DCLRE1B, NR1D2, YES1, DCLRE1A, THUMPD3, CHORDC1, ECT2, OTUB1,
MLLT6, MLLT1, NPAS1, NUP188, PDRG1, SYNJ1, KCNS1, ZCCHC3, CYP4A22, ANPEP, ZNHIT3,
ZNHIT2, C17orf62, STAC2, C17orf65, KIAA0240, SLCO2A1, ENPP3, GTPBP4, GTPBP3,
SYNPO2L, MIDN, TSEN34, CASP5, CASP1, SLC22A8, DRD4, DRD5, DRD3, CASP8, DRD1,
C14orf149, BCL9, MMRN1, BCL2, MAN2B2, ADPRHL1, RNF44, OR5I1, CDX1, CDX2, LRFN3,
OAT, LYRM7, CCK, LRFN4, UPB1, TTC9C, NKX2_5, C19orf40, C19orf41, HTR1E, AHCYL1,
C19orf46, C19orf48, A4GNT, GRK4, GRK5, FSTL3, ANAPC13, KIAA0391, CAPN7, OAS2,
CTDSP2, SERPINB12, ENTPD2, ZNF222, NBPF3, ALOX5, OASL, GRTP1, CSNK1G2,
MICAL2, KLHL3, SNAPC4, C12orf40, C12orf43, GPR21, C12orf45, SERPINB7, ZNF441, KCNMB3,
PCGF2, KCTD15, LTB4R, GSK3A, C6orf62, ATP8B4, SLC4A1, STC2, KDELR1, HIRIP3,

TABLE 5-continued

Dually stable genes common to both the Hicks/Turashvilli AND Chin/Naderi datasets ASPHD1, CLEC12A, ANKRD55, ZFP14, RBPMS2, SPRYD3, MOBKL2B, MANEA, PNMA1,
MOBKL2A, HTR1A, KLHDC3, FAM40A, LRP5L, NIPSNAP3A, KBTBD4, CDV3, RAB11FIP1,
SOHLH1, LANCL2, PCTP, PCBP2, EML3, TMEM9B, NEUROG1, POLH, MYST4, HSD17B3,
SIRT3, RAB7A, SPATA17, SPATA16, SIRT5, SIRT4, SERPINB10, SPATA19, EFEMP2,
SGTB, PAK1IP1, CDC42EP5, TRIM48, TRIM49, TRIM47, KCNF1, MTNR1A, BSCL2, FSD1,
CPLX2, FAM57A, PEX5, PEX6, POMGNT1, CCL23, NRD1, RBM25, RBM22, RBM23, SPOCK2,
PPP2R1A, CLDN11, C11orf49, EPHA7, CASC4, NDUFA11, TLR10, ME1, ME2, ATP5B, ZNF229,
NEURL2, HFE, C14orf45, ZNF747, GPR146, PGM2L1, CCDC63, TM9SF4, TBC1D2,
AFMID, TBC1D7, HSPA12A, ZWINT, TJAP1, SUCNR1, CITED4, SLC20A2, SLC7A5, POMP,
PHF21A, TFPI, RNF152, UNC13D, PRTG, KIAA2018, NRSN1, SPINK2, SYNE2, C9orf140,
PRB4, GOPC, KIR2DL3, C18orf54, YTHDC1, C18orf56, ZCRB1, ZNF526, ZNF528, RIN1, KCNMB2,
PDE4DIP, EMP2, C9orf3, RIMS3, C10orf10, ZNF253, ZNF254, FIBP, CNTNAP1, LGALS14,
RIPK3, ROCK2, EIF2S1, CEP135, COL23A1, TXN, PAPSS2, TXK, CRABP1, CDKN3,
UBQLN3, DPEP1, C17orf57, BMP5, TH, ZNF418, ZNF417, ZNF416, KCTD20, ZNF414, DAPK2,
NR3C2, ULK1, TFAM, PIM3, KCNJ14, ZFPL1, C17orf56, SSSCA1, ORC4L, TAPBPL, MYNN,
DENND3, TIAF1, DAZAP1, CYP4A11, ADM, KCNT1, SFRS16, PTPRE, SFRS14, G3BP1,
SFRS12, PLAC8, MYOZ3, PTPRJ, TAS2R7, DTWD1, C17orf70, LASS4, SLC6A2, LTB4R2,
PPAPDC2, STK10, IFNAR2, FKBP5, MFAP5, FKBP7, USP31, JSRP1, SLC6A7, MED12L, FKBP8,
NDUFAB1, GAPVD1, NAPSA, C6orf120, TYROBP, CDC42SE2, PIK3R4, DMPK, SV2A,
HEBP1, HEBP2, SV2B, IRAK4, DOC2A, OR5J2, WDR5, MUTED, RNASEH1, SMR3B, CAPZA1,
SMR3A, MON2, SULT1E1, ERGIC1, GATA2, C19orf52, C19orf51, TAS2R8, KCNA1, CCND3,
CCND2, PELO, TCF15, PRR13, PRR11, PRR14, TCF12, C11orf40, CCRL1, CDK5RAP3,
ATP6V1D, EGFLAM, TNFSF10, DIRAS1, ZNF619, SH3GL1, RAB6A, CHRNA10, UROS, PARP8,
AGXT2L2, SLC17A2, SFXN1, CHL1, CRYBA1, TAS2R1, C21orf45, SERPINE2, SOX18,
NPIP, TNNT3, CCNT2, SOX11, SOX12, C6orf70, KCNMA1, MRFAP1L1, EFTUD2, KIF2C,
DMAP1, SSTR5, OPCML, MAP1LC3B, PDLIM4, PDLIM5, ZFP28, PDLIM3, CLEC11A, IRGC,
MMD, GDI2, FTL, DCK, HIST1H2BD, ZDHHC7, DSTN, ZC3H3, PSAP, GABRP, NBEAL1, PRDM4,
WDR34, SLC22A6, SLC22A7, GPX4, GPX7, SLC25A42, TRPC4AP, IL15RA, CRIP3,
KRT18, NPDC1, TLE1, LETM1, TLE6, UPK1A, POLG, SLC4A4, TAF11, MYST3, ADCYAP1,
POLN, CYHR1, DCTN4, TRIM52, HIC1, BTBD11, CRYZL1, TFPT, WFDC10B, RAD51AP1, RET,
C2orf15, RBM17, RBM15, GGN, C9orf89, MVP, C10orf11, IL17B, IL17C, C10orf18, FDX1,
PLCL2, RXRA, PLCL1, TUBAL3, MVD, VTI1B, TAF1B, F2, GPR150, F7, SSBP4, ATP6V1E1,
SSTR1, ABCA7, C10orf88, ABCA2, A2ML1, ABCA1, FAM89B, CCBL1, TUBGCP5, KCNC4,
GCH1, MT2A, KLRD1, COX5B, SPARCL1, MYOT, HOXD10, ZNF14, TRIM28, ZNF16, ZNF17,
CPSF3, C10orf81, CPSF1, EPS15, PPFIA3, RTDR1, ZNF10, TMEM41B, LMCD1, HOXD4,
CALN1, ZNF649, ILVBL, SRGAP3, ZNF642, ZNF643, HSD17B6, NOS1, ITGB3, BANP, TTLL3,
TTLL2, PRMT6, FBP2, KPNB1, RTN1, JAG1, RTN3, RRN3, ABR, ATN1, SPATA5L1, PLA2G4C,
ST6GALNAC6, ST6GALNAC4, BEST1, ST6GALNAC1, PMPCB, TNIP2, ATP4A, ATP4B,
DKK4, PRCD, MBD5, MBD4, ZNF468, MBD6, MBD3, MBD2, LILRA6, LILRA4, AASDHPPT,
LILRA2, AICDA, FAM126B, LILRA1, TM4SF1, COL11A1, ZFPM1, TSPAN14, PKP4, PKP3,
C6orf153, PATZ1, NUDT21, GCM2, ROS1, PEBP1, ACAA2, NFE2L1, POPDC3, VAV2, SLC12A5,
EAF1, ZNF267, NDUFA10, FOXF1, SLC12A3, CCDC13, RAX, C17orf46, C17orf47, TEP1,
EXT2, IMP4, CXCL12, ACIN1, RBBP9, LPO, SCGB1C1, HS6ST1, TXNDC6, MAD1L1, NR2F6,
PMAIP1, HPSE, DYNLRB1, ADCY2, ZNF132, CNOT6, KIF25, GNG3, YIPF1, ALDH5A1,
MMAB, OSBP, ELMO2, SNX1, CYB5R4, STAR, NAP1L5, ALG2, SPTAN1, RPL27A, UGT3A1,
FUZ, SECTM1, WDR85, IKZF5, COX6B1, ARL4D, BTF3L4, CCDC126, CCDC124, CCDC123,
ITGB7, YPEL2, CTTNBP2NL, INSL6, TIMELESS, CCL26, MKL2, ITPKC, RAB11B, C11orf52,
CLDN4, UNC93A, RASGEF1C, RASGEF1B, RASGEF1A, SLC24A5, LGALS12,
MRAP, HGS, SMYD4, GALNT8, GALNT9, SMYD2, GALNT5, C12orf24, C12orf23, TUBB2C, IRF3,
IRF7, RNASEH2C, HAT1, COMTD1, IRF8, FAM78A, POLDIP3, CLUL1, MED6, HMX2, SNX21,
DMWD, SNX25, CD74, C6orf162, HDAC5, HDAC4, FXR1, RUNDC1, RFC5, HTN3, ONECUT1,
HTN1, RFC2, APC2, MARS2, AKR1C4, MESP1, CBX5, MXD4, CBX3, CBX1, P2RY1,
FASTKD3, MMP21, BTLA, TNFSF9, CCPG1, FASN, SRP72, RAB15, RAB17, ACVR2A, C4orf22,
GTDC1, PNPLA1, ASCL2, ASCL3, GPHA2, TRIM68, ACADSB, TCF25, OIT3, GPX2, OMG,
OR10H2, OR10H3, OR10H1, ALDH2, SPATC1, ZFP36, RPL10A, CUZD1, C3AR1, CDC20B,
LENG9, LENG8, ATP5F1, ERCC8, IFNGR2, LRRC8D, ACRBP, ELAVL4, LAIR2, ERCC4,
USP5, SOX8, SOX9, RNF34, SPIRE2, VSTM1, OPRL1, RNF31, CILP, GABARAPL1, BIK, CEBPE,
PTGES2, RAD54L, BID, PRR4, RND2, MED10, TNNI2, TNNI3, R3HDM2, VIPR1, C19orf36,
C10orf137, LMAN2L, ZNF540, JUB, INTS7, ZC3H7B, ZC3H7A, LSM4, PSME2, LSM1, PSME1,
KCNA10, CYBA, CEACAM19, AFF4, FAM102A, SLC1A5, HMGA1, CIDEC, DHCR24, FBXL22,
CLEC4D, CLEC4C, CLEC4A, NOTCH3, SSR1, NCBP2, ZNF658, COPS7A, UBE2F,
DEFB127, DEFB126, DEFB125, DEFB124, DEFB123, CACNG5, ZNF653, CACNG7, TM7SF4,
HSF5, CRLF3, CRLF1, SERPINF2, EPB41L4B, FZD9, PPM1J, TPBG, APOC4, MYL5, APOC2,
RLN1, RLN2, MYL1, SLC30A5, SLC30A4, SLC30A7, CLDND2, MTERFD3, RANBP17,
DNAJB13, ZNF384, ZNF354A, ZNF382, C1RL, TSNARE1, MPP3, MPP2, PRODH2, MPP6, RORA,
MAPK8IP1, ZNF479, INHBC, MAGI3, GP9, LYPD3, ZNF471, GP5, ZNF473, UGT2B4, PRPSAP1,
GPI, NARS2, JMJD1C, KRTAP3_2, CEP152, KRTAP3_1, SLC25A22, SLC25A23,
NUPL2, KAAG1, MIPOL1, ELAVL3, SLC3A2, MAN1A2, IKBKB, ATIC, CNN1, CCL16, SNRPD1,
CNN2, SLTM, SFI1, VPS26B, KIT, CCL18, KPNA5, OPTN, ZNF276, NCAPH, COPB1, MYO5B,
MYO5A, TTC30A, KCNV1, SYNGR2, RIC8B, CRX, CRTC1, TNFRSF17, YSK4, PRKAB2,
AP4B1, LY86, MAML1, RTN4IP1, TRPM4, FNDC3B, SURF2, SURF4, B4GALT7, ZFAND2A,
FCN2, FCN1, BECN1, C20orf96, GBP3, GBP2, GBP1, DHRS13, MAN2A2, SGOL2, GBP4, SIGIRR,
HERC2, HERC5, PTPDC1, APOLD1, CR2, SPACA1, TNFRSF1A, PEX5L, CYP19A1, INSM2,
NPHP3, WIZ, C17orf58, NIPSNAP3B, SULT2B1, C11orf67, C17orf53, C11orf63, TFDP1,
ZNF584, IFNAR1, GPR172A, MKNK2, ZNF586, CD4, C12orf10, CD7, ZFP30, RHOT2, RAF1,
CD9, OR10A4, EHMT1, STAT6, KIR3DL3, STAT2, SEC23B, SNX10, CD81, CHRNB3, SNX19,
PTPN6, MRPL14, MARK1, MARK2, SLC8A3, SLC8A2, BCL7A, CCDC11, ZNF611, CD63,
SCP2, SLC12A2, LY6K, CD69, BICC1, PROK1, GABRB3, EBNA1BP2, STATH, BTBD10, LRP3, TABLE 5-continued Dually stable genes common to both the Hicks/Turashvilli AND Chin/Naderi datasets NEUROD1, LRP6, GALNT13, LRP4, LRP5, CDS1, LRP8, ARPC5L, CHURC1, ACTR3B,
C1orf162, C1orf163, SRP68, C1orf161, METTL7B, PDE4C, CALR3, FBXL16, PEG3, MAP4K1,
AOX1, MAP4K2, TRIM73, LIMK2, CCDC74B, S100P, CYCS, MRPS23, BMPR1A, MAP2K1,
MAP7, CRIPAK, C8G, AACS, C17orf42, TEAD1, CAMLG, CNBP, S100B, PTPN22, DYDC1,
MT3, CGGBP1, MT4, SON, ZFP41, MAP3K12, AMBN, GAK, PPY, ATP5G1, MALT1, ATP5G2,
WNT2B, TSC22D2, HSPB3, COL18A1, CYP4V2, HSPB8, MCHR2, GPR171, MEPE, RHOBTB3,
C10orf46, ALDOA, IL21R, BAZ1A, RGS7BP, HRASLS, ZNF710, ZNF713, PSAT1, PLOD2,
ARC, SPG7, TOM1L1, HAO1, ABCC6, ABCC1, BCL2L7, IFI35, TMOD1, HRK, KCNE4,
LAT2, PSMF1, EDEM1, ZNF79, CASP14, SCO2, ZNF70, UTS2R, ZNF76, ZNF77, CYP2F1, RYR1,
NDST1, AVIL, BRPF1, ZFP2, YIF1B, ANKMY1, GOLGA2, TESK2, GOLGA7, EDN1, ZNF662,
ZNF664, ZNF667, KLRB1, MLF1IP, COLEC11, FNTA, ENPP6, HK3, FAM84A, BOLL, TSPAN1,
GIPC2, ATP2B2, NKX6_3, ZNF444, ZNF446, KCTD10, ZNF440, MTCH1, BARHL1,
FZR1, MEGF10, MRPL45, SUPT4H1, ALG10B, PTMS, GFRA3, HIGD2A, ADAMTS14, TRIM6,
SLC2A3, KIAA1407, C9orf7, ADAMTS19, C9orf4, DNM1, DCP1B, SLC25A32, SLC25A39,
C15orf33, C9orf9, GIPC3, TRABD, CPA3, IGSF10, TCP11L1, PVRL2, PIK3R3, PIK3R2, SAMD3,
IFT122, BET1L, SAMD8, NHP2L1, LNX2, SLC14A2, CNTD1, IFT74, C15orf2, GAPDHS,
GYS1, OBFC2B, C18orf22, NPHS1, CNIH, PTCRA, SCGB1A1, OR7C2, ZNF324B, KIAA0467,
ZNF195, TRIP4, ETV7, LRRC17, LRRC14, PCID2, G6PC, TMEM50B, FAM8A1, C14orf101,
GNG8, CXCL10, FAM111B, BTBD2, AGPS, CFL1, EHD1, RAD51L1, RAD51L3, SS18L2, CCNG2,
NOM1, ABL1, LGALS13, FNIP1, CCDC105, TNFAIP8L1, CCDC106, OBP2B, NPVF, OBP2A,
BICD2, CRELD2, POLD4, C6orf108, BCAS2, PDCD7, IL4I1, PDCD5, TCF20, REEP6,
CECR1, SNX8, CECR5, CECR6, ARL6IP6, ARL6IP4, SYDE1, SLC6A13, CHRNA6, CHRNA3,
GHSR, CHRNA9, PSPN, RGS14, PLAC1L, PSPH, ZNF101, PHF20L1, RHBDD1, TIMM22,
SLFNL1, C9orf16, ATPBD4, C9orf11, TXNDC11, CD58, CRYAB, STRA13, CIT, SEC31A, ANKRD5,
RAB35, RAB34, UPK3B, CAND2, TAF6L, FSHB, RAB38, BRPF3, DOK3, C1orf177, GLH,
DAP, DOK7, TTLL13, TTLL12, GMPR2, SIGLEC9, LRP10, PDGFA, LRP12, PDIA2, PLAU,
PLAT, GPC1, RAB3B, RAB3A, LRG1, C1orf190, SIGLEC6, MRPL23, NFIC, PLEKHG3, PLEKHG6,
SLC7A14, CD163, BBS2, SLC7A10, SCD5, KIAA1984, ANKDD1A, SPATA9, SIGLEC,
GDNF, INSL4, PTRF, SIGLEC5, SERPINH1, SIGLEC7, ZNF764, WNT11, EFCAB4A Supporting Information

TABLE S1

Comprehensive List of Biological Pathways Enriched with
Gene Products Having Stable Copy Number and Expression

| Enriched KEGG Pathway | Number of Observed Stable Genes | Number of Expected Stable Genes | P-Value |
| --- | --- | --- | --- |
| Neuroactive ligand-receptor interaction* | 95 | 44.3609 | 7.32e−14 |
| Cytokine-cytokine receptor interaction* | 81 | 37.4054 | 2.54e−12 |
| MAPK signaling pathway* | 74 | 41.115 | 1.76e−7 |
| Regulation of actin cytoskeleton | 64 | 30.4498 | 1.88e−9 |
| Focal adhesion* | 64 | 29.3679 | 3.55e−10 |
| Oxidative phosphorylation | 52 | 17.4662 | 1.46e−14 |
| Wnt signaling pathway | 52 | 22.1032 | 7.30e−10 |
| Purine metabolism | 51 | 22.5669 | 5.20e−9 |
| Insulin signaling pathway | 50 | 20.0938 | 1.57e−10 |
| Jak-STAT signaling pathway* | 48 | 22.1032 | 6.04e−8 |
| Tight junction | 44 | 17.3116 | 8.75e−10 |
| Natural killer cell mediated cytotoxicity | 43 | 18.3936 | 2.58e−8 |
| Leukocyte transendothelial migration | 41 | 17.3116 | 3.53e−8 |
| Ribosome | 39 | 14.8385 | 2.50e−9 |
| Cell cycle* | 39 | 17.157 | 2.64e−7 |
| Axon guidance | 38 | 18.7027 | 8.26e−6 |
| Cell adhesion molecules (CAMs) | 37 | 19.1664 | 3.81e−5 |
| Pyrimidine metabolism | 37 | 13.7565 | 2.98e−9 |
| Calcium signaling pathway | 36 | 25.6582 | 2.03e−2 |
| Chronic myeloid leukemia | 33 | 11.1289 | 1.03e−9 |
| Adherens junction* | 32 | 11.2834 | 7.19e−9 |
| TGF-beta signaling pathway* | 32 | 12.3654 | 1.01e−7 |
| Glycan structures - biosynthesis 1 | 32 | 15.3022 | 2.17e−5 |
| T cell receptor signaling pathway | 31 | 13.9111 | 6.83e−6 |
| Hematopoietic cell lineage | 31 | 12.9837 | 1.29e−6 |
| Colorectal cancer | 30 | 12.3654 | 1.28e−6 |
| Antigen processing and presentation | 30 | 11.1289 | 8.52e−8 |
| Adipocytokine signaling pathway | 29 | 10.6652 | 1.11e−7 |
| Tryptophan metabolism | 28 | 12.3654 | 1.33e−5 |
| GnRH signaling pathway | 26 | 14.5294 | 1.75e−3 |
| Starch and sucrose metabolism | 26 | 10.2015 | 2.19e−6 |
| Cell Communication | 26 | 16.2296 | 8.70e−3 |
| Glycan structures - biosynthesis 2 | 25 | 10.0469 | 5.68e−6 |
| Long-term depression | 25 | 11.7471 | 1.20e−4 |

TABLE S1-continued

Comprehensive List of Biological Pathways Enriched with
Gene Products Having Stable Copy Number and Expression

| Enriched KEGG Pathway | Number of Observed Stable Genes | Number of Expected Stable Genes | P-Value |
| --- | --- | --- | --- |
| Gap junction | 25 | 13.1383 | 8.17e−4 |
| Pancreatic cancer | 24 | 10.9743 | 1.01e−4 |
| Fc epsilon RI signaling pathway | 24 | 11.438 | 2.09e−4 |
| B cell receptor signaling pathway | 24 | 9.4286 | 5.47e−6 |
| Tyrosine metabolism | 24 | 8.1921 | 2.54e−7 |
| PPAR signaling pathway | 23 | 10.356 | 1.07e−4 |
| VEGF signaling pathway | 23 | 10.6652 | 1.77e−4 |
| ECM-receptor interaction | 23 | 12.6746 | 2.57e−3 |
| Apoptosis | 22 | 12.52 | 4.82e−3 |
| Arginine and proline metabolism | 22 | 8.1921 | 4.74e−6 |
| Glioma | 22 | 9.2741 | 4.83e−5 |
| Lysine degradation | 21 | 7.7284 | 6.21e−6 |
| Glycolysis/Gluconeogenesis | 21 | 9.1195 | 1.17e−4 |
| Ubiquitin mediated proteolysis | 20 | 6.6464 | 1.49e−6 |
| Metabolism of xenobiotics by Cytochrome P450 | 20 | 8.8104 | 2.11e−4 |
| Glycerolipid metabolism | 20 | 8.5012 | 1.20e−4 |
| Epithelial cell signaling in *Helicobacter pylori* infection | 20 | 10.2015 | 1.75e−3 |
| Phosphatidylinositol signaling system | 19 | 10.6652 | 7.21e−3 |
| Long-term potentiation | 19 | 10.2015 | 4.27e−3 |
| Androgen and estrogen metabolism | 19 | 6.6464 | 6.98e−6 |
| Arachidonic acid metabolism | 18 | 8.5012 | 1.10e−3 |
| Type II diabetes mellitus | 18 | 6.4918 | 2.03e−5 |
| Fructose and mannose metabolism | 17 | 7.2647 | 4.10e−4 |
| N-Glycan biosynthesis | 17 | 5.719 | 1.12e−5 |
| Hedgehog signaling pathway | 17 | 8.3467 | 2.41e−3 |
| Taste transduction | 17 | 6.6464 | 1.17e−4 |
| Fatty acid metabolism | 16 | 6.9555 | 7.47e−4 |
| Glutathione metabolism | 16 | 6.3373 | 2.20e−4 |
| Notch signaling pathway | 16 | 7.1101 | 9.83e−4 |
| Nicotinate and nicotinamide metabolism | 16 | 6.0281 | 1.10e−4 |
| Neurodegenerative Disorders | 16 | 5.2553 | 1.39e−5 |
| Butanoate metabolism | 16 | 6.801 | 5.61e−4 |
| Glycine, serine and threonine metabolism | 15 | 6.6464 | 1.36e−3 |
| ABC transporters - General | 15 | 5.719 | 2.10e−4 |
| Folate biosynthesis | 15 | 6.0281 | 4.14e−4 |
| Bile acid biosynthesis | 14 | 5.719 | 7.76e−4 |
| Pathogenic *Escherichia coli* infection - EPEC | 14 | 6.6464 | 4.02e−3 |
| Pathogenic *Escherichia coli* infection - EHEC | 14 | 6.6464 | 4.02e−3 |
| Histidine metabolism | 14 | 6.0281 | 1.42e−3 |
| Citrate cycle (TCA cycle) | 13 | 4.1733 | 6.63e−5 |
| Urea cycle and metabolism of amino groups | 13 | 3.7096 | 1.30e−5 |
| Pyruvate metabolism | 13 | 6.1827 | 5.57e−3 |
| RNA polymerase | 13 | 3.5551 | 6.97e−6 |
| Selenoamino acid metabolism | 13 | 4.9462 | 5.37e−4 |
| Alanine and aspartate metabolism | 12 | 4.7916 | 1.45e−3 |
| Phenylalanine metabolism | 12 | 4.1733 | 3.25e−4 |
| Cholera - Infection | 12 | 6.0281 | 1.22e−2 |
| Pantothenate and CoA biosynthesis | 12 | 3.7096 | 7.96e−5 |
| Carbon fixation | 11 | 3.5551 | 2.62e−4 |
| Proteasome | 11 | 4.7916 | 4.98e−3 |
| Porphyrin and chlorophyll metabolism | 11 | 4.3279 | 1.97e−3 |
| Huntington's disease | 10 | 3.8642 | 2.68e−3 |
| DNA polymerase | 10 | 3.8642 | 2.68e−3 |
| beta-Alanine metabolism | 9 | 3.5551 | 5.17e−3 |
| Nitrobenzene degradation | 8 | 2.1639 | 4.04e−4 |
| Riboflavin metabolism | 8 | 2.3185 | 7.48e−4 |
| Glycosphingolipid biosynthesis - neo-lactoseries | 8 | 2.9368 | 4.92e−3 |
| Glycosphingolipid biosynthesis - globoseries | 7 | 2.1639 | 2.63e−3 |
| Glyoxylate and dicarboxylate metabolism | 7 | 1.8548 | 8.08e−4 |
| Amyotrophic lateral sclerosis (ALS) | 7 | 2.6277 | 9.75e−3 |
| Caprolactam degradation | 7 | 2.3185 | 4.28e−3 |
| Sulfur metabolism | 6 | 2.0094 | 8.73e−3 |
| Fatty acid biosynthesis | 5 | 0.9274 | 4.61e−4 |

KEGG pathways are listed in decreasing order by the number of observed stable genes within the pathway. Fisher exact p-values (<0.01) show significance of pathways with more stable genes observed per pathway than expected. Pathways denoted by an asterisk indicate those previously established to be essential in tumor progression. The others have not been previously recognized and may provide further insight into essential cancer pathways.

TABLE S2

PCR Parameters for a Subset of in cis Multi-Copy DNA Targets

| Genes and Associated Genomic Coordinates* | Copy Number (haploid genome) | Forward Primer (5' → 3') | Reverse Primer (5' → 3') |
|---|---|---|---|
| Q-PCR | | | |
| IGFPB4<br>chr17:35853229-35853356 | 1 | AGCGCCCTGGGGTTT CTTGGCCT | CAGAAGGGAAATTAGCCA GACCCTGGAGCA |
| RMND5A<br>chr2:86952093-86952192 | 3 | GCCAGCTTCTGAATTA TGGTCTTC | GAAACTCAATGGAACCTT CTGTTTC |
| C2orf78<br>chr2:73869885-73869987 | 6 | GTCTCTTCTTCCCTTC TATCTGCAGTT | GGCAAAGAAATCTCATGA AAACCT |
| GOLGA6L1<br>chr15:20296359-20296475 | 12 | TGATTGGTCAACAGT AGAGGGCTA | CATTAGGTCATTTCAGCCC TGTG |
| LOC728411<br>chr5:21513474-21513790 | 18 | ACCATTTTGGAGCAT GGTGA | GGAAGTACAGCCCCTAAA AGTG |
| FAM90A14<br>chr8:7098869-7100116 | 22 | AGTCTCTGCCTCAGCT ACTCTTAGGA | CGTGAAGTGGCTTCCGGA T |
| ERBB2<br>chr17:35107192-35107416 | Variable in breast cancer cell lines | GGGCAGCCAAGGGGC TGCAAAGC | GCCACTCCCTCTGCCCCA CAGT |
| FISH | | | |
| DEFA1<br>chr8:6824681-6828923 | 3 | GTTCCAAAGACCTGT GATAGTCTCTCTCTAC | AGGAAGCTATTTCCTTATG GTTTATTGTA |
| PI4KA<br>chr22:18764821-18767520 | 3 | CCTGACACCACACTC AGTTCTAATACT | GGGTTGGACTCCTTAGAA GAAAGTTAAG |

*NCBI 36/hg18 assembly

Primers were designed for amplification of varying copies of a sequence (associated gene and genomic coordinates are noted in column 1). The amplicons ranged in length from 100-224 bp for quantitative PCR (Q-PCR); and were 2700 bp (PI4KA) and 4242 bp (DEFA1) for fluorescence in situ hybridization (FISH). The multi-copy sequences were associated with the following genes: IGFBP4, insulin-like growth factor binding protein 4; RMND54, required for meiotic nuclear division 5 homolog A (*S. Cerevisiae*); C2orf78, hypothetical protein LOC388960; GOLGA6L1, golgin A6 family-like 1; LOC728411, similar to *H. Sapiens* WD repeat domain 70 (WDR70); FAM90A14, family with sequence similarity 90, member A14; ERBB2, V-erb-b2 erythroblastic leukemia viral oncogene; DEFA1, defensin alpha 1; and, PI4KA, phosphatidylinositol 4-kinase, alpha.

TABLE S3

Characterizing Stable Intervals and Frequency Distribution of Recurrent Abnormalities Reported in Breast Cancer Cases

| | Stable Regions | | Mitelman | |
|---|---|---|---|---|
| Chromosome | Number of Stable Intervals | Total Length (in bp) of Stable Regions (Percentage %) | Number of Breast Cancer Cases (Number of Abnormalities) | Frequency of Abnormality (%) |
| 1 | 1,805 | 2,896,018 (4.87) | 558 (73) | 10.7 |
| 2 | 3,581 | 5,457,167 (9.17) | 161 (25) | 3.1 |
| 3 | 1,200 | 1,810,796 (3.04) | 348 (60) | 6.6 |
| 4 | 1,652 | 3,414,672 (5.74) | 178 (24) | 3.4 |
| 5 | 2,021 | 3,048,671 (5.12) | 194 (29) | 3.7 |
| 6 | 1,352 | 2,321,519 (3.90) | 302 (56) | 5.8 |
| 7 | 2,145 | 3,305,336 (5.55) | 288 (37) | 5.5 |
| 8 | 1,006 | 1,676,541 (2.82) | 241 (25) | 4.6 |
| 9 | 3,758 | 5,916,329 (9.94) | 173 (24) | 3.3 |
| 10 | 3,154 | 4,754,357 (7.99) | 182 (20) | 3.5 |
| 11 | 1,874 | 2,860,601 (4.81) | 272 (40) | 5.2 |
| 12 | 1,108 | 1,646,963 (2.77) | 199 (28) | 3.8 |
| 13 | 521 | 763,974 (1.28) | 207 (21) | 4.0 |
| 14 | 827 | 1,415,016 (2.38) | 175 (20) | 3.3 |
| 15 | 2,925 | 4,475,378 (7.52) | 171 (17) | 3.3 |
| 16 | 2,418 | 3,931,980 (6.61) | 293 (29) | 5.6 |
| 17 | 2,371 | 3,750,052 (6.30) | 239 (24) | 4.6 |

TABLE S3-continued

Characterizing Stable Intervals and Frequency Distribution
of Recurrent Abnormalities Reported in Breast Cancer Cases

| | Stable Regions | | Mitelman | |
| --- | --- | --- | --- | --- |
| Chromosome | Number of Stable Intervals | Total Length (in bp) of Stable Regions (Percentage %) | Number of Breast Cancer Cases (Number of Abnormalities) | Frequency of Abnormality (%) |
| 18 | 211 | 330,498 (0.56) | 241 (20) | 4.6 |
| 19 | 1,158 | 1,854,062 (3.11) | 203 (17) | 3.9 |
| 20 | 500 | 783,049 (1.32) | 202 (18) | 3.9 |
| 21 | 590 | 899,626 (1.51) | 189 (17) | 3.6 |
| 22 | 1,296 | 2,211,375 (3.72) | 222 (25) | 4.2 |
| TOTAL | 37,473 | 59,523,980 | 5238 (649) | 100 |

(Mitelman F, Johanson B, Mertens F. Mitelman Database of Chromosome Aberrations and Gene Fusions in Cancer. 2011.)

This table displays the number of repeat-masked stable intervals that includes segmentally duplicated sequences and total base pair (bp) lengths for each chromosome. Recurrent (structural and numerical) abnormalities from the Mitelman database were assessed in relation to the proportion of stable intervals on each chromosome. There is an inverse relationship between the frequency of cytogenetic abnormality and amount of coverage of stable intervals; larger stable regions are associated with lower frequencies of abnormality. For example, chromosomes 2, 9, 10, and 15 are associated with larger proportions of stable regions and the lowest frequencies of abnormalities; chromosomes 8, 13, 18, and 20 have relatively lower lengths of stable regions and higher frequency of abnormalities.

TABLE S4

Genome-Wide Distribution of Stable Multi-Copy Sequences that Occur in cis and in trans

| Copy number per Haploid Genome | Chromosome |
|---|---|

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|
| 2 | 4/0 | 193/1 | 1/0 | 88/3 | 76/5 | 82/3 | 45/3 | 207/11 | 10/10 | 115/0 | 48/6 | 84/6 | 44/1 | 33/4 | 87/4 | 138/117 | 151/1 | 25/6 | 23/14 | 31/4 | 43/65 | 43/38 |
| 3* | 0/12 | 16/2 | 0/0 | 12/3 | 7/3 | 9/3 | 0/0 | 28/4 | 26/6 | 0/0 | 10/2 | 6/1 | 0/0 | 3/0 | 17/5 | 117/0 | 52/0 | 0/0 | 3/8 | 6/1 | 42/0 | 58/0 |
| 4 | 4/0 | 14/1 | 0/0 | 0/2 | 1/2 | 0/0 | 0/0 | 20/3 | 0/3 | 0/0 | 2/0 | 0/0 | 0/0 | 0/0 | 12/4 | 46/0 | 7/0 | 0/0 | 0/1 | 0/0 | 6/20 | 6/7 |
| 5 | 15/0 | 8/0 | 0/0 | 0/1 | 4/1 | 0/2 | 0/0 | 0/7 | 9/11 | 0/1 | 1/1 | 0/1 | 7/0 | 0/1 | 9/1 | 11/1 | 0/0 | 0/0 | 2/6 | 0/0 | 0/1 | 0/0 |
| 6* | 1/0 | 7/1 | 0/0 | 1/0 | 1/1 | 0/1 | 0/0 | 0/1 | 3/1 | 0/0 | 0/1 | 0/0 | 0/1 | 0/0 | 0/0 | 8/1 | 0/1 | 0/0 | 12/0 | 0/0 | 1/0 | 0/0 |
| 7 | 6/0 | 5/0 | 0/0 | 0/0 | 0/0 | 0/0 | 0/0 | 0/4 | 0/4 | 0/0 | 0/0 | 0/0 | 0/0 | 0/0 | 0/0 | 6/2 | 0/2 | 0/0 | 1/0 | 0/0 | 15/0 | 0/0 |
| 8 | 6/0 | 0/1 | 0/0 | 0/0 | 0/3 | 0/4 | 0/0 | 0/3 | 0/0 | 0/0 | 0/2 | 0/0 | 0/0 | 0/0 | 0/0 | 4/1 | 0/0 | 0/0 | 0/3 | 0/0 | 28/0 | 0/0 |
| 9 | 8/0 | 1/0 | 0/0 | 18/1 | 3/0 | 0/7 | 0/0 | 0/6 | 0/0 | 0/0 | 0/8 | 0/0 | 0/0 | 0/0 | 0/0 | 9/0 | 0/0 | 0/0 | 0/9 | 0/0 | 14/0 | 0/0 |
| 10 | 2/0 | 0/0 | 0/0 | 0/0 | 0/0 | 0/0 | 0/0 | 0/1 | 0/0 | 0/0 | 0/1 | 0/0 | 0/0 | 0/0 | 0/0 | 6/0 | 0/0 | 0/0 | 0/0 | 0/0 | 0/0 | 0/0 |
| 11 | 5/0 | 0/0 | 0/0 | 0/0 | 0/0 | 0/0 | 0/0 | 0/2 | 0/0 | 0/0 | 0/0 | 0/0 | 0/0 | 0/0 | 0/0 | 0/1 | 0/0 | 0/0 | 0/1 | 0/1 | 0/0 | 0/0 |
| 12* | 1/0 | 1/0 | 0/0 | 0/0 | 0/0 | 0/1 | 0/0 | 0/0 | 0/1 | 0/0 | 0/1 | 0/0 | 0/0 | 0/0 | 0/0 | 5/0 | 0/1 | 0/0 | 0/1 | 0/0 | 0/0 | 0/0 |
| 13 | 2/0 | 0/0 | 0/0 | 0/0 | 0/0 | 0/0 | 0/0 | 0/0 | 0/0 | 0/0 | 0/1 | 0/0 | 0/0 | 0/0 | 0/0 | 0/1 | 0/0 | 0/0 | 0/1 | 0/2 | 0/0 | 0/0 |
| 15 | 0/0 | 0/0 | 0/0 | 0/0 | 0/0 | 0/0 | 0/0 | 1/0 | 0/0 | 0/0 | 0/0 | 0/0 | 0/0 | 0/0 | 0/0 | 0/5 | 0/0 | 0/0 | 0/0 | 0/0 | 0/0 | 0/0 |
| 16 | 0/0 | 0/0 | 0/0 | 0/0 | 0/0 | 0/0 | 0/0 | 0/0 | 0/0 | 0/0 | 0/1 | 0/0 | 0/0 | 0/0 | 0/0 | 5/0 | 0/1 | 0/0 | 0/1 | 0/0 | 0/0 | 0/0 |
| 17 | 3/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/1 | 0/0 | 0/0 | 0/0 |
| 18* | 0/0 | 0/0 | 0/0 | 0/0 | 0/0 | 0/0 | 0/0 | 0/0 | 0/0 | 0/0 | 0/1 | 0/0 | 0/0 | 0/0 | 0/0 | 0/0 | 0/0 | 0/0 | 0/1 | 0/0 | 0/0 | 0/0 |
| 20 | 0/0 | 0/0 | 0/0 | 0/0 | 0/1 | 0/0 | 0/0 | 0/0 | 0/0 | 0/0 | 0/0 | 0/0 | 0/0 | 0/0 | 0/0 | 0/0 | 0/0 | 0/0 | 0/0 | 0/2 | 0/0 | 0/0 |
| 21 | 0/0 | 0/0 | 0/0 | 0/0 | 20/1 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 |
| 22* | 0/0 | 0/0 | 0/0 | 0/0 | 0/0 | 0/0 | 0/0 | 23/1 | 0/0 | 0/0 | 0/0 | 0/0 | 0/0 | 0/0 | 0/0 | 0/1 | 0/1 | 0/0 | 0/1 | 0/0 | 0/0 | 0/0 |
| 23 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 | 0/0 |
| 26 | 0/0 | 0/0 | 0/0 | 0/0 | 0/0 | 0/0 | 0/0 | 0/1 | 0/0 | 0/0 | 0/0 | 0/0 | 0/0 | 0/0 | 0/0 | 0/0 | 0/0 | 0/0 | 0/0 | 0/0 | 0/0 | 0/0 |

*refers to the copy-number per haploid genome that has been tested by Q-PCR

Subfamilies of multi-copy sequences were genomically distributed within the same chromosome (in cis; upper half of cell) or across different chromosomes (in trans; lower half of cell). Most multi-copy sequences range from two to nine copies across most chromosomes, with the exception of the presence of many multi-copy sequences of 20 and 22 copies on chromosomes 5 and 8, respectively. Each repeat-masked stable interval was used in an mpiBLAST analysis to determine stable sequences occurring in multiple copies with sequence similarity parameters of 70% for at least 200 bp and 80% for at least 100 bp of a stable sequence.

TABLE S5

FISH Results on Breast Cancer Cell Lines

| Breast Cancer Cell Line | Modal Number (range) | Number of Chromosomes with Hybridization/Cell | | | | |
|---|---|---|---|---|---|---|
| | | CSF1R | FLT4 | GMPR2 | PI4KA | DEFA1 |
| SKBR3 | 78 (72-79) | 3 | — | 2 or 3 | 2 | 2 |
| MCF7 | 71 (60-69) | 3 | 3 | 3 | 2 | 1 |
| HS578T | 52 (50-56) | 3 | 2 | 3 | 2 | 2 |
| T47D | 52 (52-62) | 3 | 3 | 2 | 2 | 2 |
| MDA-MB-231 | 86 (84-94) | 3 | 3 | 2 | 2 | 2 |

Fluorescence in situ hybridization (FISH) was performed on metaphase cells of 5 breast cancer cell lines using BAC probes for three stable drug target genes (CSF1R, FLT4, GMPR2) and amplicon genomic probes for two stable multi-copy sequences (PI4KA, DEFA1). For all cell lines (ranging in modal numbers), copy number remained relatively stable; '—' refers to not determined.

TABLE S6

Comprehensive Table of Biological Pathways Enriched for Stable Genes ($n_1$ vs. $n_2$)

| KEGG Pathway | Number of Stable Genes ($n_1$) | Number of Stable Genes ($n_2$) |
|---|---|---|
| Neuroactive ligand-receptor interaction | 95 | 56 |
| Cytokine-cytokine receptor interaction | 81 | 71 |
| MAPK signaling pathway | 74 | 67 |
| Regulation of actin cytoskeleton | 64 | 50 |
| Focal adhesion | 64 | 51 |
| Oxidative phosphorylation | 52 | 33 |
| Wnt signaling pathway | 52 | 40 |
| Purine metabolism | 51 | 38 |
| Insulin signaling pathway | 50 | 37 |
| Jak-STAT signaling pathway | 48 | 34 |
| Tight junction | 44 | 21 |
| Natural killer cell mediated cytotoxicity | 43 | 29 |
| Leukocyte transendothelial migration | 41 | 22 |
| Ribosome | 39 | 35 |
| Cell cycle | 39 | 31 |
| Axon guidance | 38 | 29 |
| Cell adhesion molecules (CAMs) | 37 | 23 |
| Pyrimidine metabolism | 37 | 14 |
| Calcium signaling pathway | 36 | 42 |
| Chronic myeloid leukemia | 33 | 20 |
| Adherens junction | 32 | 13 |
| TGF-beta signaling pathway | 32 | 23 |
| T cell receptor signaling pathway | 31 | 33 |
| Hematopoietic cell lineage | 31 | 22 |
| Colorectal cancer | 30 | 23 |
| Antigen processing and presentation | 30 | 17 |
| Adipocytokine signaling pathway | 29 | 25 |
| Tryptophan metabolism | 28 | 14 |
| GnRH signaling pathway | 26 | 18 |
| Starch and sucrose metabolism | 26 | 13 |
| Long-term depression | 25 | 14 |
| Gap junction | 25 | 19 |
| Pancreatic cancer | 24 | 21 |
| B cell receptor signaling pathway | 24 | 24 |
| Tyrosine metabolism | 24 | 10 |
| PPAR signaling pathway | 23 | 19 |
| VEGF signaling pathway | 23 | 14 |
| ECM-receptor interaction | 23 | 24 |
| Toll-like receptor signaling pathway | 22 | 25 |
| Apoptosis | 22 | 22 |
| Arginine and proline metabolism | 22 | 17 |
| Glioma | 22 | 15 |
| Lysine degradation | 21 | 10 |
| Glycolysis/Gluconeogenesis | 21 | 23 |
| Ubiquitin mediated proteolysis | 20 | 35 |
| Metabolism of xenobiotics by Cytochrome P450 | 20 | 21 |
| Glycerolipid metabolism | 20 | 12 |
| Epithelial cell signaling in *Helicobacter pylori* infection | 20 | 15 |
| Phosphatidylinositol signaling system | 19 | 22 |
| Long-term potentiation | 19 | 20 |
| Arachidonic acid metabolism | 18 | 14 |
| Type II diabetes mellitus | 18 | 12 |
| Fructose and mannose metabolism | 17 | 12 |
| N-Glycan biosynthesis | 17 | 9 |
| Hedgehog signaling pathway | 17 | 19 |
| Taste transduction | 17 | 10 |
| Fatty acid metabolism | 16 | 14 |
| Glutathione metabolism | 16 | 17 |
| Glycerophospholipid metabolism | 16 | 12 |
| Notch signaling pathway | 16 | 10 |
| Butanoate metabolism | 16 | 10 |
| Folate biosynthesis | 15 | 4 |
| Histidine metabolism | 14 | 6 |
| Citrate cycle (TCA cycle) | 13 | 9 |
| Valine, leucine and isoleucine degradation | 13 | 15 |
| Complement and coagulation cascades | 13 | 20 |
| Inositol phosphate metabolism | 13 | 14 |
| Pyruvate metabolism | 13 | 10 |
| Phenylalanine metabolism | 12 | 5 |
| mTOR signaling pathway | 12 | 12 |
| Proteasome | 11 | 15 |
| Porphyrin and chlorophyll metabolism | 11 | 8 |
| Sphingolipid metabolism | 10 | 9 |
| Propanoate metabolism | 10 | 10 |
| Huntington's disease | 10 | 43 |
| Type I diabetes mellitus | 10 | 9 |

TABLE S6-continued

Comprehensive Table of Biological Pathways
Enriched for Stable Genes ($n_1$ vs. $n_2$)

| KEGG Pathway | Number of Stable Genes ($n_1$) | Number of Stable Genes ($n_2$) |
|---|---|---|
| beta-Alanine metabolism | 9 | 8 |
| Olfactory transduction | 9 | 109 |
| Pentose phosphate pathway | 8 | 12 |
| Linoleic acid metabolism | 8 | 7 |
| Aminoacyl-tRNA biosynthesis | 8 | 8 |
| Galactose metabolism | 7 | 12 |
| Glyoxylate and dicarboxylate metabolism | 7 | 4 |
| Amyotrophic lateral sclerosis (ALS) | 7 | 14 |
| Basal transcription factors | 7 | 9 |
| Limonene and pinene degradation | 7 | 4 |
| Dorso-ventral axis formation | 6 | 6 |
| Alzheimer's disease | 6 | 47 |
| One carbon pool by Mate | 6 | 4 |
| O-Glycan biosynthesis | 5 | 9 |
| Nitrogen metabolism | 5 | 7 |
| Parkinson's disease | 3 | 33 |
| Vitamin B6 metabolism | 2 | 4 |
| Retinol metabolism | 2 | 20 |
| D-Glutamine and D-glutamate metabolism | 1 | 4 |

This table lists KEGG pathways enriched in stable genes by both the Hicks et al ($n_1$) and Chin et al ($n_2$) datasets. These pathways were all significant based on Fisher exact p-values (<0.01), with more stable genes observed per pathway than expected.

TABLE S7

Comprehensive Table of Gene Ontologies Enriched for Stable Genes ($n_1$ vs. $n_2$)

| Accession Number | Gene Ontology | Number of Stable Genes ($n_1$) | Number of Stable Genes ($n_2$) |
|---|---|---|---|
| GO:0007166 | cell surface receptor linked signal transduction | 160 | 427 |
| GO:0019220 | regulation of phosphate metabolic process | 70 | 128 |
| GO:0051174 | regulation of phosphorus metabolic process | 70 | 128 |
| GO:0044093 | positive regulation of molecular function | 76 | 161 |
| GO:0042325 | regulation of phosphorylation | 68 | 125 |
| GO:0043085 | positive regulation of catalytic activity | 70 | 143 |
| GO:0007610 | behavior | 62 | 119 |
| GO:0010941 | regulation of cell death | 79 | 193 |
| GO:0042981 | regulation of apoptosis | 78 | 190 |
| GO:0010647 | positive regulation of cell communication | 50 | 83 |
| GO:0043067 | regulation of programmed cell death | 78 | 192 |
| GO:0031399 | regulation of protein modification process | 46 | 91 |
| GO:0043549 | regulation of kinase activity | 50 | 105 |
| GO:0006468 | protein amino acid phosphorylation | 68 | 167 |
| GO:0045859 | regulation of protein kinase activity | 49 | 101 |
| GO:0007243 | protein kinase cascade | 50 | 99 |
| GO:0051338 | regulation of transferase activity | 50 | 107 |
| GO:0032268 | regulation of cellular protein metabolic process | 55 | 138 |
| GO:0006796 | phosphate metabolic process | 79 | 258 |
| GO:0006793 | phosphorus metabolic process | 79 | 258 |
| GO:0032270 | positive regulation of cellular protein metabolic process | 38 | 78 |
| GO:0051247 | positive regulation of protein metabolic process | 38 | 79 |
| GO:0016310 | phosphorylation | 68 | 205 |
| GO:0033674 | positive regulation of kinase activity | 35 | 62 |
| GO:0007167 | enzyme linked receptor protein signaling pathway | 42 | 94 |
| GO:0010033 | response to organic substance | 62 | 190 |
| GO:0045860 | positive regulation of protein kinase activity | 34 | 59 |
| GO:0051347 | positive regulation of transferase activity | 35 | 63 |
| GO:0031401 | positive regulation of protein modification process | 31 | 60 |
| GO:0042330 | taxis | 28 | 49 |
| GO:0006935 | chemotaxis | 28 | 49 |
| GO:0010604 | positive regulation of macromolecule metabolic process | 66 | 237 |
| GO:0010942 | positive regulation of cell death | 45 | 107 |
| GO:0044092 | negative regulation of molecular function | 39 | 95 |
| GO:0007626 | locomotory behavior | 35 | 70 |
| GO:0042592 | homeostatic process | 60 | 189 |
| GO:0043068 | positive regulation of programmed cell death | 44 | 106 |
| GO:0009611 | response to wounding | 49 | 137 |
| GO:0051726 | regulation of cell cycle | 37 | 85 |
| GO:0030278 | regulation of ossification | 19 | 24 |
| GO:0043405 | regulation of MAP kinase activity | 23 | 41 |
| GO:0043086 | negative regulation of catalytic activity | 31 | 82 |
| GO:0006873 | cellular ion homeostasis | 36 | 98 |
| GO:0008283 | cell proliferation | 39 | 126 |
| GO:0055082 | cellular chemical homeostasis | 36 | 100 |
| GO:0012501 | programmed cell death | 47 | 147 |
| GO:0050801 | ion homeostasis | 37 | 105 |
| GO:0006928 | cell motion | 40 | 124 |
| GO:0006917 | induction of apoptosis | 32 | 80 |
| GO:0048878 | chemical homeostasis | 41 | 135 |

TABLE S7-continued

Comprehensive Table of Gene Ontologies Enriched for Stable Genes ($n_1$ vs. $n_2$)

| Accession Number | Gene Ontology | Number of Stable Genes ($n_1$) | Number of Stable Genes ($n_2$) |
|---|---|---|---|
| GO:0007178 | transmembrane receptor protein serine/threonine kinase signaling pathway | 18 | 34 |
| GO:0060341 | regulation of cellular localization | 27 | 64 |
| GO:0001775 | cell activation | 29 | 74 |
| GO:0009719 | response to endogenous stimulus | 35 | 111 |
| GO:0045669 | positive regulation of osteoblast differentiation | 10 | 10 |
| GO:0019725 | cellular homeostasis | 37 | 116 |
| GO:0007179 | transforming growth factor beta receptor signaling pathway | 13 | 21 |
| GO:0009725 | response to hormone stimulus | 31 | 99 |
| GO:0016477 | cell migration | 26 | 73 |
| GO:0031589 | cell-substrate adhesion | 15 | 33 |
| GO:0051130 | positive regulation of cellular component organization | 20 | 54 |
| GO:0031328 | positive regulation of cellular biosynthetic process | 43 | 183 |
| GO:0048534 | hemopoietic or lymphoid organ development | 24 | 73 |
| GO:0007160 | cell-matrix adhesion | 14 | 30 |
| GO:0003006 | reproductive developmental process | 24 | 70 |
| GO:0030500 | regulation of bone mineralization | 9 | 12 |
| GO:0009891 | positive regulation of biosynthetic process | 43 | 184 |
| GO:0034097 | response to cytokine stimulus | 13 | 24 |
| GO:0070167 | regulation of biomineral formation | 9 | 12 |
| GO:0010605 | negative regulation of macromolecule metabolic process | 44 | 186 |
| GO:0002520 | immune system development | 24 | 78 |
| GO:0008406 | gonad development | 15 | 37 |
| GO:0019221 | cytokine-mediated signaling pathway | 12 | 24 |
| GO:0007049 | cell cycle | 45 | 189 |
| GO:0048871 | multicellular organismal homeostasis | 13 | 25 |
| GO:0007548 | sex differentiation | 17 | 45 |
| GO:0042391 | regulation of membrane potential | 16 | 42 |
| GO:0031400 | negative regulation of protein modification process | 15 | 45 |
| GO:0048545 | response to steroid hormone stimulus | 19 | 55 |
| GO:0060249 | anatomical structure homeostasis | 14 | 31 |
| GO:0051173 | positive regulation of nitrogen compound metabolic process | 39 | 176 |
| GO:0001894 | tissue homeostasis | 11 | 20 |
| GO:0048608 | reproductive structure development | 15 | 40 |
| GO:0045137 | development of primary sexual characteristics | 15 | 40 |
| GO:0009991 | response to extracellular stimulus | 20 | 64 |
| GO:0051341 | regulation of oxidoreductase activity | 9 | 17 |
| GO:0046883 | regulation of hormone secretion | 11 | 21 |
| GO:0051248 | negative regulation of protein metabolic process | 18 | 63 |
| GO:0048872 | homeostasis of number of cells | 13 | 30 |
| GO:0030509 | BMP signaling pathway | 9 | 15 |
| GO:0043627 | response to estrogen stimulus | 13 | 30 |
| GO:0031667 | response to nutrient levels | 18 | 56 |
| GO:0032269 | negative regulation of cellular protein metabolic process | 17 | 60 |
| GO:0007565 | female pregnancy | 13 | 38 |
| GO:0010638 | positive regulation of organelle organization | 11 | 28 |
| GO:0045596 | negative regulation of cell differentiation | 18 | 58 |
| GO:0045935 | positive regulation of nucleobase, nucleoside, nucleotide and nucleic acid metabolic process | 35 | 172 |
| GO:0000079 | regulation of Cyclin-dependent protein kinase activity | 9 | 22 |
| GO:0001541 | ovarian follicle development | 8 | 14 |
| GO:0010557 | positive regulation of macromolecule biosynthetic process | 36 | 176 |
| GO:0010522 | regulation of calcium ion transport into cytosol | 7 | 11 |
| GO:0046661 | male sex differentiation | 10 | 26 |
| GO:0022402 | cell cycle process | 32 | 148 |
| GO:0031397 | negative regulation of protein ubiquitination | 10 | 31 |
| GO:0000278 | mitotic cell cycle | 24 | 101 |
| GO:0051438 | regulation of ubiquitin-protein ligase activity | 10 | 33 |
| GO:0051052 | regulation of DNA metabolic process | 12 | 33 |
| GO:0010628 | positive regulation of gene expression | 32 | 158 |
| GO:0051340 | regulation of ligase activity | 10 | 34 |
| GO:0046887 | positive regulation of hormone secretion | 7 | 14 |
| GO:0031396 | regulation of protein ubiquitination | 11 | 37 |
| GO:0051352 | negative regulation of ligase activity | 9 | 29 |
| GO:0051444 | negative regulation of ubiquitin-protein ligase activity | 9 | 29 |
| GO:0051101 | regulation of DNA binding | 12 | 36 |
| GO:0001501 | skeletal system development | 21 | 88 |
| GO:0007229 | integrin-mediated signaling pathway | 9 | 22 |
| GO:0051439 | regulation of ubiquitin-protein ligase activity during mitotic cell cycle | 9 | 31 |
| GO:0002521 | leukocyte differentiation | 12 | 39 |
| GO:0006470 | protein amino acid dephosphorylation | 12 | 40 |
| GO:0032583 | regulation of gene-specific transcription | 12 | 40 |
| GO:0018108 | peptidyl-tyrosine phosphorylation | 7 | 18 |

TABLE S7-continued

Comprehensive Table of Gene Ontologies Enriched for Stable Genes ($n_1$ vs. $n_2$)

| Accession Number | Gene Ontology | Number of Stable Genes ($n_1$) | Number of Stable Genes ($n_2$) |
|---|---|---|---|
| GO:0018212 | peptidyl-tyrosine modification | 7 | 18 |
| GO:0051436 | negative regulation of ubiquitin-protein ligase activity during mitotic cell cycle | 8 | 29 |
| GO:0048754 | branching morphogenesis of a tube | 8 | 21 |
| GO:0031398 | positive regulation of protein ubiquitination | 9 | 32 |
| GO:0030097 | hemopoiesis | 16 | 64 |
| GO:0002237 | response to molecule of bacterial origin | 9 | 28 |
| GO:0051437 | positive regulation of ubiquitin-protein ligase activity during mitotic cell cycle | 8 | 29 |
| GO:0033043 | regulation of organelle organization | 15 | 57 |
| GO:0043407 | negative regulation of MAP kinase activity | 6 | 14 |
| GO:0008584 | male gonad development | 7 | 21 |
| GO:0010038 | response to metal ion | 11 | 37 |
| GO:0045637 | regulation of myeloid cell differentiation | 8 | 22 |
| GO:0051443 | positive regulation of ubiquitin-protein ligase activity | 8 | 30 |
| GO:0051301 | cell division | 18 | 75 |
| GO:0045926 | negative regulation of growth | 10 | 32 |
| GO:0016311 | dephosphorylation | 12 | 49 |
| GO:0032870 | cellular response to hormone stimulus | 11 | 39 |
| GO:0051351 | positive regulation of ligase activity | 8 | 31 |
| GO:0032504 | multicellular organism reproduction | 25 | 120 |
| GO:0048609 | reproductive process in a multicellular organism | 25 | 120 |
| GO:0051054 | positive regulation of DNA metabolic process | 7 | 21 |
| GO:0050796 | regulation of insulin secretion | 6 | 16 |
| GO:0040007 | growth | 13 | 49 |
| GO:0032496 | response to lipopolysaccharide | 8 | 26 |
| GO:0007584 | response to nutrient | 11 | 38 |
| GO:0051353 | positive regulation of oxidoreductase activity | 5 | 10 |
| GO:0050878 | regulation of body fluid levels | 11 | 42 |
| GO:0045941 | positive regulation of transcription | 27 | 153 |
| GO:0051960 | regulation of nervous system development | 13 | 51 |
| GO:0002791 | regulation of peptide secretion | 6 | 16 |
| GO:0031145 | anaphase-promoting complex-dependent proteasomal ubiquitin-dependent protein catabolic process | 7 | 30 |
| GO:0046546 | development of primary male sexual characteristics | 7 | 24 |
| GO:0001944 | vasculature development | 15 | 68 |
| GO:0043193 | positive regulation of gene-specific transcription | 8 | 28 |
| GO:0010035 | response to inorganic substance | 13 | 56 |
| GO:0043388 | positive regulation of DNA binding | 7 | 22 |
| GO:0048514 | blood vessel morphogenesis | 13 | 59 |
| GO:0045944 | positive regulation of transcription from RNA polymerase II promoter | 19 | 104 |
| GO:0031334 | positive regulation of protein complex assembly | 5 | 13 |
| GO:0006357 | regulation of transcription from RNA polymerase II promoter | 31 | 177 |
| GO:0001568 | blood vessel development | 14 | 66 |
| GO:0010552 | positive regulation of specific transcription from RNA polymerase II promoter | 6 | 20 |
| GO:0001525 | angiogenesis | 10 | 43 |
| GO:0045893 | positive regulation of transcription, DNA-dependent | 22 | 125 |
| GO:0030098 | lymphocyte differentiation | 8 | 32 |
| GO:0051254 | positive regulation of RNA metabolic process | 22 | 128 |
| GO:0007249 | I-kappaB kinase/NF-kappaB cascade | 6 | 20 |
| GO:0042060 | wound healing | 11 | 60 |
| GO:0001508 | regulation of action potential | 6 | 21 |
| GO:0051302 | regulation of cell division | 5 | 16 |
| GO:0030183 | B cell differentiation | 5 | 19 |
| GO:0010551 | regulation of specific transcription from RNA polymerase II promoter | 7 | 29 |
| GO:0030168 | platelet activation | 4 | 12 |
| GO:0019228 | regulation of action potential in neuron | 5 | 19 |
| GO:0043161 | proteasomal ubiquitin-dependent protein catabolic process | 7 | 39 |
| GO:0010498 | proteasomal protein catabolic process | 7 | 39 |
| GO:0006511 | ubiquitin-dependent protein catabolic process | 12 | 67 |
| GO:0052548 | regulation of endopeptidase activity | 6 | 25 |
| GO:0009743 | response to carbohydrate stimulus | 5 | 22 |
| GO:0032024 | positive regulation of insulin secretion | 3 | 9 |
| GO:0052547 | regulation of peptidase activity | 6 | 25 |
| GO:0043254 | regulation of protein complex assembly | 6 | 26 |

This table lists gene ontologies enriched in stable genes by both the Hicks et al ($n_1$) and Chin et al ($n_2$) datasets.

We claim:

1. A method for determining genes having stable copy number and stable gene expression in the genomes of a preponderance of breast tumor specimens, each obtained from different cancer patients, comprising the steps of:

(a) isolating genomic DNA from a set of tumors;

(b) isolating RNA from the same set of tumors;

(c) determining copy number of a set of genes in the isolated genomic DNA;

(d) determining gene expression levels by synthesizing cDNA from RNA transcripts from the set of genes in which copy number is determined;

(e) determining a first set of genes having euploid (or stable) copy number in a set of isolated DNA samples, each genome containing distinct changes in chromosomal copy number by:

(i) determining the copy numbers of each of the genome-coordinate defined sequences by genomic hybridization, (ii) grouping all adjacent-genomic intervals that exhibit the same copy number in a tumor to form a larger contiguous genomic interval, (iii) defining contiguous genomic intervals of aneuploidy (unstable) copy number in the set of tumors as those which are segmentally aneuploidy in the tumor genomes of at least 10% of the patients, wherein segmental aneuploidy is a consistent increase or decrease of at least one copy of a target locus in all cells;

(iv) determining the set of unstable genes as the set of genes contained within contiguous genomic intervals of segmentally aneuploid copy number and the genes which occur in partially aneuploid (unstable) copy number regions, wherein partial aneuploidy indicates a mosaic increase or decrease of complete chromosomes in a fraction of the cells;

(v) determining the coordinates of the genome sequence regions between segmentally aneuploid genomic intervals as having stable copy number regions by complementing the genomic coordinates of contiguous chromosomal intervals of aneuploid copy number to produce a set of genomic intervals with stable copy number, and (vi) convolving the genomic coordinates of each of the known protein coding genes in the genome with the coordinates of the stable copy number regions, and (f) determining a second gene set comprising genes having stable expression levels in the set of isolated RNA samples by (i) determining which genes in each breast tumor genome are differentially expressed at relative to their corresponding expression levels in adjacent ductal and lobular tissues derived from normal breast of the same tumors, which is computed from the p-values of the ratios of $\log_2$ hybridization intensities (corresponding to fold changes in expression between normal and tumor tissues), which are themselves adjusted using the Benjamini-Hochberg correction for multiple testing (for genes with fold changes having p-values <0.05), and (ii) selecting the genes that are not differentially expressed in >90% of tumors as a set of stably expressed genes in all of the tumor genomes, wherein steps (e) and (f) can be performed in either order and, (g) combining the first gene set with the second gene set using a joining operation that forms a set of dually stable genes, defined as having both stable copy number and stable expression in a set of tumors, wherein the genes that are dually stable can be independently confirmed as stable based on repeating the same copy number, expression, and nucleic acid sequence analysis in an independent set of different tumors and matched normal tissues originating from the same type of tumor, and selecting the genes as dually stable gene sets that are determined to be dually stable in both the initial set and confirming tumor gene analyses.

2. The method of claim 1, where a dually stable gene encodes a protein required for metabolism of a chemotherapeutic agent approved for treatment of cancer.

3. The method of claim 2, where the required protein is bound by the chemotherapeutic agent approved for treatment of cancer.

4. The method of claim 2, where the required protein is inhibited by the chemotherapeutic agent approved for treatment of cancer.

5. The method of claim 1, where the dually stable gene encodes a protein that is epistatic, wherein an epistatic protein is a protein whose function is equivalent to another distinct protein and required for metabolism of a chemotherapeutic agent approved for treatment of cancer, and wherein the epistatic protein is identified from the metabolic pathway containing the stable drug target, and the protein required for metabolism resides in the same pathway as the dually stable gene product.

6. The method of claim 5, where the protein required for metabolism is bound by metabolism of the chemotherapeutic agent approved for treatment of cancer.

7. The method of claim 5, where the protein required for metabolism is inhibited by metabolism of the chemotherapeutic agent approved for treatment of cancer.

8. The method of claim 2, where the chemotherapeutic agent which targets a dually stable gene product is selected for treatment of a patient.

9. The method of claim 5, where the chemotherapeutic agent which targets the protein that is epistatic to a dually stable gene product is selected for treatment of a patient.

10. The method of claim 2, where the nucleic acid sequence of a dually stable gene is determined in an individual tumor sample and demonstrated to be normal, and the chemotherapeutic agent which targets the protein encoded by this gene is selected for treatment of a patient from whom the tumor was obtained.

11. The method of claim 5, where the nucleic acid sequence of a dually stable gene that is epistatic to one or more distinct proteins required for metabolism of the chemotherapeutic agent is determined in an individual tumor sample and demonstrated to be normal, and the chemotherapeutic agent which targets the epistatic protein is selected for treatment of a patient from whom the tumor was obtained.

12. The method of claim 2, where the nucleic acid sequence of a dually stable gene is determined in an individual tumor sample and is demonstrated to contain a mutation that reduces or abolishes the activity of the protein it encodes, and the chemotherapeutic agent which targets the protein encoded by this gene is not selected for treatment of a patient from whom the tumor was obtained.

13. The method of claim 5, where the nucleic acid sequence of a dually stable gene that is epistatic to one or more distinct proteins required for metabolism of the chemotherapeutic agent is determined in an individual tumor sample and demonstrated to contain a mutation that reduces or abolishes the activity of the protein it encodes, and the chemotherapeutic agent which targets the epistatic protein is not selected for treatment of a patient from whom the tumor was obtained.

14. The method of claim 1, where a dually stable gene encodes a protein required for metabolism of a chemotherapeutic agent approved for treatment of diseases other than cancer.

15. The method of claim 1, where the dually stable gene encodes a protein that is epistatic to one or more distinct proteins required for metabolism of a chemotherapeutic agent approved for treatment of diseases other than cancer, wherein the epistatic protein is identified from the metabolic pathway containing the stable drug target, and the protein required for metabolism resides in the same pathway as the dually stable gene product.

16. The method of claim 14, where the chemotherapeutic agent which targets a dually stable gene product is selected for treatment of a patient.

17. The method of claim 15, where the chemotherapeutic agent which targets protein that is epistatic to a dually stable gene product is selected for treatment of a patient.

18. The method of claim 14, where the nucleic acid sequence of a dually stable gene is determined in an individual tumor sample and demonstrated to be normal, and the chemotherapeutic agent which targets the protein encoded by this gene is selected for treatment of a patient from whom the tumor was obtained.

19. The method of claim 15, where the nucleic acid sequence of a dually stable gene that is epistatic to one or more distinct proteins required for metabolism of the chemotherapeutic agent is determined in an individual tumor sample and demonstrated to be normal, and the chemotherapeutic agent which targets the epistatic protein is selected for treatment of a patient from whom the tumor was obtained.

20. The method of claim 14, where the nucleic acid sequence of a dually stable gene is determined in an individual tumor sample and is demonstrated to contain a mutation that reduces or abolishes the activity of the protein it encodes, and the chemotherapeutic agent which targets the protein encoded by this gene is not selected for treatment of a patient from whom the tumor was obtained.

21. The method of claim 15, where the nucleic acid sequence of a dually stable gene that is epistatic to one or more distinct proteins required for metabolism of the chemotherapeutic agent is determined in an individual tumor sample and demonstrated to contain a mutation that reduces or abolishes the activity of the protein it encodes, and the chemotherapeutic agent which targets the epistatic protein is not selected for treatment of a patient from whom the tumor was obtained.

22. A method for determining genes having stable copy number and stable gene expression in the genomes of a preponderance of breast tumor specimens, each obtained from different cancer patients, comprising the steps of:
   (a) isolating genomic DNA from a set of tumors;
   (b) isolating RNA from the same set of tumors;
   (c) determining copy number of a set of genes in the isolated genomic DNA;
   (d) determining gene expression levels using cDNA synthesized from RNA transcripts from the set of genes in which copy number is determined;
   (e) determining a first set of genes having euploid (or stable) copy number in a set of isolated DNA samples, each genome containing distinct changes in chromosomal copy number by:
      (i) determining the copy numbers of each of the genome-coordinate defined sequences by genomic hybridization,
      (ii) grouping all adjacent-genomic intervals that exhibit the same copy number in a tumor to form a larger contiguous genomic interval,
      (iii) defining contiguous genomic intervals of aneuploidy (unstable) copy number in the set of tumors as those which are segmentally aneuploidy in the tumor genomes of at least 10% of the patients, wherein segmental aneuploidy is a consistent increase or decrease of at least one copy of a target locus in all cells;
      (iv) determining the set of unstable genes as the set of genes contained within contiguous genomic intervals of segmentally aneuploid copy number and the genes which occur in partially aneuploid (unstable) copy number regions, wherein partial aneuploidy indicates a mosaic increase or decrease of complete chromosomes in a fraction of the cells;
      (v) determining the coordinates of the genome sequence regions between segmentally aneuploid genomic intervals as having stable copy number regions by complementing the genomic coordinates of contiguous chromosomal intervals of aneuploid copy number to produce a set of genomic intervals with stable copy number, and
      (vi) convolving the genomic coordinates of each of the known protein coding genes in the genome with the coordinates of the stable copy number regions, and
   (f) determining a second gene set comprising genes having stable expression levels in the set of isolated RNA samples by
      (i) determining which genes in each breast tumor genome are differentially expressed at relative to their corresponding expression levels in adjacent ductal and lobular tissues derived from normal breast of the same tumors, which is computed from the p-values of the ratios of $\log_2$ hybridization intensities (corresponding to fold changes in expression between normal and tumor tissues), which are themselves adjusted using the Benjamini-Hochberg correction for multiple testing (for genes with fold changes having p-values <0.05), and
      (ii) selecting the genes that are not differentially expressed in >90% of tumors as a set of stably expressed genes in all of the tumor genomes,
   wherein steps (e) and (f) can be performed in either order and,
   (g) combining the first gene set with the second gene set using a joining operation that forms a set of dually stable genes, defined as having both stable copy number and stable expression in a set of tumors, wherein the genes that are dually stable can be independently confirmed as stable based on repeating the same copy number, expression, and nucleic acid sequence analysis in an independent set of different tumors and matched normal tissues originating from the same type of tumor, and selecting the genes as dually stable gene sets that are determined to be dually stable in both the initial set and confirming tumor gene analyses, where at least one dually stable gene encodes a protein.

23. The method for determining genes having stable copy number in the genomes of a preponderance of breast tumor specimens of claim 22 where the nucleic acid sequence of a dually stable gene that is epistatic, wherein an epistatic protein is a protein whose function is equivalent to another distinct protein and required for metabolism of a chemotherapeutic agent, and is determined in an individual tumor sample and demonstrated to contain a mutation that reduces or abolishes the activity of the protein it encodes, and the chemotherapeutic agent which targets the epistatic protein is not selected for treatment of a patient from whom the tumor was obtained.

24. The method for determining genes having stable copy number in the genomes of a preponderance of breast tumor specimens of claim 22 where a dually stable gene encodes a protein required for metabolism of a chemotherapeutic agent approved for treatment of diseases other than cancer.

25. The method for determining genes having stable copy number in the genomes of a preponderance of breast tumor specimens of claim 22 where the dually stable gene encodes a protein that is epistatic to one or more distinct proteins required for metabolism of a chemotherapeutic agent approved for treatment of diseases other than cancer, wherein the epistatic protein is identified from the metabolic pathway containing the stable drug target, and the protein required for metabolism resides in the same pathway as the dually stable gene product.

* * * * *

SEQUENCE LISTING

<160> NUMBER OF SEQ ID NOS: 18

<210> SEQ ID NO 1
<211> LENGTH: 23
<212> TYPE: DNA
<213> ORGANISM: Artificial Sequence
<220> FEATURE:
<223> OTHER INFORMATION: IGFPB4 - Forward Primer

<400> SEQUENCE: 1
agcgccctgg ggtttcttgg cct                                           23

<210> SEQ ID NO 2
<211> LENGTH: 30
<212> TYPE: DNA
<213> ORGANISM: Artificial Sequence
<220> FEATURE:
<223> OTHER INFORMATION: IGFPB4 - Reverse Primer

<400> SEQUENCE: 2
cagaagggaa attagccaga ccctggagca                                    30

<210> SEQ ID NO 3
<211> LENGTH: 24
<212> TYPE: DNA
<213> ORGANISM: Artificial Sequence
<220> FEATURE:
<223> OTHER INFORMATION: RMND5A - Forward Primer

<400> SEQUENCE: 3
gccagcttct gaattatggt cttc                                          24

<210> SEQ ID NO 4
<211> LENGTH: 25
<212> TYPE: DNA
<213> ORGANISM: Artificial Sequence
<220> FEATURE:
<223> OTHER INFORMATION: RMND5A - Reverse Primer

<400> SEQUENCE: 4
gaaactcaat ggaaccttct gtttc                                         25

<210> SEQ ID NO 5
<211> LENGTH: 27
<212> TYPE: DNA
<213> ORGANISM: Artificial Sequence
<220> FEATURE:
<223> OTHER INFORMATION: C2orf78 - Forward Primer

<400> SEQUENCE: 5
gtctcttctt cccttctatc tgcagtt                                       27

<210> SEQ ID NO 6
<211> LENGTH: 24
<212> TYPE: DNA
<213> ORGANISM: Artificial Sequence
<220> FEATURE:
<223> OTHER INFORMATION: C2orf78 - Reverse Primer

<400> SEQUENCE: 6
ggcaaagaaa tctcatgaaa acct                                          24

<210> SEQ ID NO 7
<211> LENGTH: 24
<212> TYPE: DNA
<213> ORGANISM: Artificial Sequence

```
<220> FEATURE:
<223> OTHER INFORMATION: GOLGA6L1 - Forward Primer

<400> SEQUENCE: 7
tgattggtca acagtagagg gcta                                        24

<210> SEQ ID NO 8
<211> LENGTH: 23
<212> TYPE: DNA
<213> ORGANISM: Artificial Sequence
<220> FEATURE:
<223> OTHER INFORMATION: GOLGA6L1 - Reverse Primer

<400> SEQUENCE: 8
cattaggtca tttcagccct gtg                                         23

<210> SEQ ID NO 9
<211> LENGTH: 20
<212> TYPE: DNA
<213> ORGANISM: Artificial Sequence
<220> FEATURE:
<223> OTHER INFORMATION: LOC728411 - Forward Primer

<400> SEQUENCE: 9
accattttgg agcatggtga                                             20

<210> SEQ ID NO 10
<211> LENGTH: 22
<212> TYPE: DNA
<213> ORGANISM: Artificial Sequence
<220> FEATURE:
<223> OTHER INFORMATION: LOC728411 - Reverse Primer

<400> SEQUENCE: 10
ggaagtacag cccctaaaag tg                                          22

<210> SEQ ID NO 11
<211> LENGTH: 26
<212> TYPE: DNA
<213> ORGANISM: Artificial Sequence
<220> FEATURE:
<223> OTHER INFORMATION: FAM90A14 - Forward Primer

<400> SEQUENCE: 11
agtctctgcc tcagctactc ttagga                                      26

<210> SEQ ID NO 12
<211> LENGTH: 19
<212> TYPE: DNA
<213> ORGANISM: Artificial Sequence
<220> FEATURE:
<223> OTHER INFORMATION: FAM90A14 - Reverse Primer

<400> SEQUENCE: 12
cgtgaagtgg cttccggat                                              19

<210> SEQ ID NO 13
<211> LENGTH: 23
<212> TYPE: DNA
<213> ORGANISM: Artificial Sequence
<220> FEATURE:
<223> OTHER INFORMATION: ERBB2 - Forward Primer

<400> SEQUENCE: 13
gggcagccaa gggggctgcaa agc                                        23
```

```
<210> SEQ ID NO 14
<211> LENGTH: 23
<212> TYPE: DNA
<213> ORGANISM: Artificial Sequence
<220> FEATURE:
<223> OTHER INFORMATION: ERBB2 - Reverse Primer

<400> SEQUENCE: 14
gccactccct ctgcccccac agt                                              23

<210> SEQ ID NO 15
<211> LENGTH: 31
<212> TYPE: DNA
<213> ORGANISM: Artificial Sequence
<220> FEATURE:
<223> OTHER INFORMATION: DEFA1 - Forward Primer

<400> SEQUENCE: 15
gttccaaaga cctgtgatag tctctctcta c                                     31

<210> SEQ ID NO 16
<211> LENGTH: 29
<212> TYPE: DNA
<213> ORGANISM: Artificial Sequence
<220> FEATURE:
<223> OTHER INFORMATION: DEFA1 - Reverse Primer

<400> SEQUENCE: 16
aggaagctat ttccttatgg tttattgta                                        29

<210> SEQ ID NO 17
<211> LENGTH: 27
<212> TYPE: DNA
<213> ORGANISM: Artificial Sequence
<220> FEATURE:
<223> OTHER INFORMATION: PI4KA - Forward Primer

<400> SEQUENCE: 17
cctgacacca cactcagttc taatact                                          27

<210> SEQ ID NO 18
<211> LENGTH: 28
<212> TYPE: DNA
<213> ORGANISM: Artificial Sequence
<220> FEATURE:
<223> OTHER INFORMATION: PI4KA - Reverse Primer

<400> SEQUENCE: 18
gggttggact ccttagaaga aagttaag                                         28
```